(12) United States Patent
Koch et al.

(10) Patent No.: US 10,512,212 B2
(45) Date of Patent: Dec. 24, 2019

(54) SYSTEMS, METHODS, AND APPARATUS FOR SOIL AND SEED MONITORING

(71) Applicant: THE CLIMATE CORPORATION, San Francisco, CA (US)

(72) Inventors: Dale Koch, Tremont, IL (US); Michael Strnad, Delevan, IL (US); Matthew Morgan, Tremont, IL (US); Brian McMahon, Tremont, IL (US)

(73) Assignee: THE CLIMATE CORPORATION, San Francisco, CA (US)

( * ) Notice: Subject to any disclaimer, the term of this patent is extended or adjusted under 35 U.S.C. 154(b) by 0 days.

(21) Appl. No.: 15/844,394

(22) Filed: Dec. 15, 2017

(65) Prior Publication Data

US 2018/0168094 A1    Jun. 21, 2018

Related U.S. Application Data

(60) Provisional application No. 62/436,342, filed on Dec. 19, 2016, provisional application No. 62/446,254, (Continued)

(51) Int. Cl.
*A01C 21/00* (2006.01)
*G01J 5/04* (2006.01)
(Continued)

(52) U.S. Cl.
CPC .......... *A01C 21/005* (2013.01); *A01C 5/064* (2013.01); *A01C 7/102* (2013.01); *A01C 7/203* (2013.01);
(Continued)

(58) Field of Classification Search
USPC .......................................................... 701/50
See application file for complete search history.

(56) References Cited

U.S. PATENT DOCUMENTS 2,366,389 A    1/1945    Davenport
3,749,035 A    7/1973    Cayton et al.
(Continued)

FOREIGN PATENT DOCUMENTS

CA    2 948 354        11/2015
DE    4121218 A1        3/1992
(Continued)

OTHER PUBLICATIONS

Stoller, U.S. Appl. No. 15/672,024, filed Aug. 8, 2017, Office Action, dated Jun. 11, 2018.
(Continued)

*Primary Examiner* — Tyler D Paige
(74) *Attorney, Agent, or Firm* — Hickman Palermo Becker Bingham LLP; Christine E. Orich

(57) ABSTRACT

Systems, methods and apparatus are provided for monitoring soil properties including soil moisture, soil electrical conductivity and soil temperature during an agricultural input application. Embodiments include a soil reflectivity sensor and/or a soil temperature sensor mounted to a seed firmer for measuring moisture and temperature in a planting trench. A thermopile for measuring temperature via infrared radiation is described herein. In one example, the thermopile is disposed in a body and senses infrared radiation through an infrared transparent window. Aspects of any of the disclosed embodiments may be implemented in or communicate with an agricultural intelligence computer system as described herein.

82 Claims, 58 Drawing Sheets

Related U.S. Application Data filed on Jan. 13, 2017, provisional application No. 62/482,116, filed on Apr. 5, 2017, provisional application No. 62/516,553, filed on Jun. 7, 2017.

(51) Int. Cl.

| | |
|---|---|
| *G01N 21/47* | (2006.01) |
| *B60K 35/00* | (2006.01) |
| *A01C 7/10* | (2006.01) |
| *B60W 10/30* | (2006.01) |
| *G01N 33/24* | (2006.01) |
| *G01N 27/04* | (2006.01) |
| *G01N 27/22* | (2006.01) |
| *G01V 8/10* | (2006.01) |
| *G01K 1/16* | (2006.01) |
| *A01C 5/06* | (2006.01) |
| *G01N 21/3563* | (2014.01) |
| *A01C 7/20* | (2006.01) |
| *G01N 21/55* | (2014.01) |
| *A01B 63/16* | (2006.01) |
| *G01N 21/3554* | (2014.01) |
| *A01B 63/111* | (2006.01) |

(52) U.S. Cl.

CPC ............ *B60K 35/00* (2013.01); *B60W 10/30* (2013.01); *G01J 5/04* (2013.01); *G01K 1/16* (2013.01); *G01N 21/3563* (2013.01); *G01N 21/474* (2013.01); *G01N 27/043* (2013.01); *G01N 27/223* (2013.01); *G01N 33/24* (2013.01); *G01N 33/246* (2013.01); *G01V 8/10* (2013.01); *A01B 63/111* (2013.01); *A01B 63/16* (2013.01); *A01C 5/068* (2013.01); *B60K 2370/11* (2019.05); *B60W 2550/00* (2013.01); *B60W 2710/30* (2013.01); *G01N 21/3554* (2013.01); *G01N 21/55* (2013.01); *G01N 2021/4742* (2013.01); *G01N 2033/243* (2013.01); *G01N 2033/245* (2013.01)

(56) References Cited

U.S. PATENT DOCUMENTS

| | | |
|---|---|---|
| 4,103,177 A | 1/1978 | Sanford et al. |
| 4,116,140 A | 9/1978 | Anderson et al. |
| 4,374,500 A | 2/1983 | Westerfield |
| 4,413,685 A | 11/1983 | Gremelspacher et al. |
| 5,038,040 A | 8/1991 | Funk et al. |
| 5,044,756 A | 9/1991 | Gaultney et al. |
| 5,296,702 A | 3/1994 | Beck et al. |
| 5,355,815 A | 10/1994 | Monson |
| 5,387,977 A | 2/1995 | Berg et al. |
| 5,398,771 A | 3/1995 | Hornung |
| 5,461,229 A | 10/1995 | Sauter et al. |
| 5,563,340 A | 10/1996 | Clowater et al. |
| 5,621,666 A | 4/1997 | O'Neall et al. |
| 5,673,637 A | 10/1997 | Colburn, Jr. et al. |
| 5,841,282 A | 11/1998 | Christy et al. |
| 5,852,982 A | 12/1998 | Peter |
| 5,887,491 A | 3/1999 | Monson et al. |
| 5,931,882 A | 8/1999 | Fick et al. |
| 6,016,714 A | 1/2000 | Smith et al. |
| 6,148,747 A | 11/2000 | Decker et al. |
| 6,216,794 B1 | 4/2001 | Buchl |
| 6,389,999 B1 | 5/2002 | Duello |
| 6,484,652 B1 | 11/2002 | Colburn, Jr. |
| 6,510,367 B1 | 1/2003 | Masten et al. |
| 6,596,996 B1 | 7/2003 | Stone et al. |
| 6,608,672 B1 | 8/2003 | Shibusawa et al. |
| 6,827,029 B1 | 12/2004 | Wendte |
| 7,216,555 B2 | 5/2007 | Drummond et al. |
| 7,408,145 B2 | 8/2008 | Holland |
| 7,723,660 B2 | 5/2010 | Holland |
| 7,726,251 B1 | 6/2010 | Peterson et al. |
| 7,849,955 B2 | 12/2010 | Crabill et al. |
| 8,204,689 B2 | 6/2012 | Christy et al. |
| 8,319,165 B2 | 11/2012 | Holland |
| 8,451,449 B2 | 5/2013 | Holland |
| 8,558,157 B2 | 10/2013 | Holland |
| 8,755,049 B2 | 6/2014 | Holland |
| 8,814,626 B2 | 8/2014 | Smith |
| 8,816,262 B2 | 8/2014 | Holland |
| 8,849,523 B1 | 9/2014 | Chan et al. |
| 8,924,092 B2 | 12/2014 | Achen et al. |
| 9,026,316 B2 | 5/2015 | Holland |
| 9,075,008 B2 | 7/2015 | Holland |
| 9,285,501 B2 | 3/2016 | Christy et al. |
| 9,585,301 B1 | 3/2017 | Lund et al. |
| 9,585,307 B2 | 3/2017 | Holland |
| 9,629,304 B2 | 4/2017 | Zielke |
| 9,651,536 B1 | 5/2017 | Lund et al. |
| 9,675,004 B2 | 6/2017 | Landphair et al. |
| 9,743,574 B1 | 8/2017 | Maxton et al. |
| 9,943,027 B2 | 4/2018 | Sauder et al. |
| 2002/0131046 A1 | 9/2002 | Christy et al. |
| 2002/0171842 A1 | 11/2002 | Dicarlo et al. |
| 2003/0048449 A1 | 3/2003 | Vander Jagt et al. |
| 2004/0145379 A1 | 7/2004 | Buss |
| 2004/0255834 A1 | 12/2004 | Schaffert |
| 2005/0172733 A1* | 8/2005 | Drummond .......... A01B 79/005 73/864.41 |
| 2006/0074560 A1* | 4/2006 | Dyer .................... A01B 79/005 702/5 |
| 2006/0158652 A1 | 7/2006 | Rooney et al. |
| 2007/0272134 A1 | 11/2007 | Baker et al. |
| 2008/0291455 A1 | 11/2008 | Holland |
| 2009/0112475 A1 | 4/2009 | Christy et al. |
| 2010/0023430 A1 | 1/2010 | Hunter et al. |
| 2010/0180695 A1 | 7/2010 | Sauder et al. |
| 2011/0106451 A1* | 5/2011 | Christy ................ G01N 21/359 702/5 |
| 2012/0042813 A1 | 2/2012 | Liu et al. |
| 2013/0104785 A1 | 5/2013 | Achen |
| 2013/0112122 A1 | 5/2013 | Blomme |
| 2013/0125800 A1 | 5/2013 | Landphair |
| 2013/0138289 A1 | 5/2013 | Sauder |
| 2013/0180742 A1 | 7/2013 | Wendte et al. |
| 2013/0250280 A1 | 9/2013 | Holland |
| 2014/0303854 A1* | 10/2014 | Zielke .................... A01C 21/00 701/50 |
| 2014/0343802 A1 | 11/2014 | Pichlmaier |
| 2015/0094917 A1 | 4/2015 | Blomme |
| 2015/0105984 A1 | 4/2015 | Birrell |
| 2015/0107503 A1 | 4/2015 | Masten et al. |
| 2015/0163992 A1* | 6/2015 | Anderson ............ A01C 21/005 701/50 |
| 2015/0334914 A1* | 11/2015 | Zielke .................... A01C 21/00 701/50 |
| 2015/0347647 A1* | 12/2015 | Osborne ................ B09C 1/002 703/6 |
| 2016/0037709 A1* | 2/2016 | Sauder .................... A01C 7/203 700/275 |
| 2016/0302351 A1* | 10/2016 | Schildroth ........... A01B 79/005 |
| 2017/0045489 A1 | 2/2017 | Sauder |
| 2017/0061052 A1 | 3/2017 | Gates |
| 2017/0067869 A1 | 3/2017 | Lund et al. |
| 2017/0086359 A1 | 3/2017 | Landphair et al. |
| 2017/0090068 A1 | 3/2017 | Xiang |
| 2017/0172058 A1 | 6/2017 | Lund et al. |
| 2017/0213083 A1 | 7/2017 | Shriver |
| 2018/0168094 A1* | 6/2018 | Koch ...................... G01J 5/04 |
| 2019/0191623 A1 | 6/2019 | Stoller |

FOREIGN PATENT DOCUMENTS

| | | |
|---|---|---|
| GB | 2126062 A | 3/1986 |
| WO | WO9636889 A1 | 11/1996 |
| WO | WO 01/76352 A1 | 10/2001 |
| WO | WO2015/171908 A1 | 7/2004 |

(56) References Cited

FOREIGN PATENT DOCUMENTS

| WO | WO2012129442 | 9/2012 |
|---|---|---|
| WO | WO2012149398 | 11/2012 |
| WO | WO2012149415 | 11/2012 |

OTHER PUBLICATIONS

International Searching Authority, "Search Report" in application No. PCT/US17/66861, dated Mar. 14, 2018, 15 pages.
Current Claims in application No. PCT/US17/66861, dated Mar. 2018, 17 pages.
Sudduth et al., Soil Organic Matters CEC, and Moisture Sensing with a Portable NIR Spectrophotometer, Power and Machinery Division of ASAE, vol. 36(6): 1571-1582, Nov.-Dec. 1993, 12 pages.
Sudduth et al., "Portable, Near-Infrared Spectrophotometer for Rapid Soil Analysis", vol. 36(1): Jan.-Feb. 1993, Information and Electrical Technologies Systems Div. of ASAE, 10 pages.
Schirrmann et al, Soil pH Mapping with an On-The-Go-Sensor, Sensors 2011, 11, 573-598; doi:10.3390/s110100573, 26 pages.
Morgan et al., "Precision Farming: Sensors vs. Map-Based", Agricultural and Biological Engineering Department, Apr. 1995. 2 pages.
Maleki et al., "Optimisation of Soil VIS-NIR Sensor-based Variable Rate Application System of Soil Phosphorus", Soil & Tillage Research 94 (2007), pp. 239-250.
Lagacherie et al., "Visible-NIR Hyperspecttal Imagery for Discrimination Soil Types in the La Peyne Watershed", France, Developments in Soil Science vol. 31, Chapter 17, , dated 2007 16 pages.
Hummel et al., "Soil Property Sensing for Site-Specific Crop Management", Computers and Electronics in Agriculture 14 (1996), pp. 121-136.
Hummel et al., "Soil Moisture and Organic Matter Prediction of Surface and Subsurface Soils Using an NIR Soil Sensor", Computers and Electronics in Agriculture 32 (2001) pp. 149-165.
Grisso et al., "Precision Farming Tools: Variable Rate Application", Publication 442-505 Virginia Cooperative Extension, dated 2011, 16 pages.
Gaultney et al., "Soil Moisture Sensor for Predicting Seed Planting Depth", vol. 36(6) dated Nov.-Dec. 1993, pp. 1703-1711.
Ess et al., "Implementing Site-Specific Management: Map- Versus Sensor-Based Variable Rate Application", Purdue University SSM-2-W, Jan. 2001, 9 pages.
Adamchuk et al., "On-the-Go Vehicle Based Soil Sensors", University of Nebraska Cooperative Extension EC 02-178, undated, 4 pages.
Adamchuk et al., "On-the-go Soil Sensors for Precision Agriculture", Computers and Electronics in Agriculture 44 (2004), pp. 71-91.
Adamchuk et al., "On-the-Go Capacitance Sensing of Soil Water Content", ASABE Meeting Presentation, Paper No. MC09-201, Apr. 4-5, 2009, 8 pages.
Adamchuk et al., "Characterizing Soil Variability Using On-the-Go Sensing Technology", Site-Specific Management Guidelines, SSMG-44, May 2006, 4 pages.
Stoller, U.S. Appl. No. 15/672,024, filed Aug. 8, 2017, Notice of Allowance, dated Oct. 18, 2018.
Canadian Intellectual Property Office, "Search Report" in application No. 2,948,354 dated Mar. 14, 2019, 4 pages.
Canadian Claims in application No. 2,948,354, dated Mar. 2019, 2 pages.
The International Bureau of WIPO, "International Preliminary on Patentability" in Application No. PCT/US2017/066861, dated Jun. 25, 2019, 13 pages.
Current Claims in application No. PCT/US2017/066861, dated Jun. 2019, 16 pages.
Canadian Intellectual Property Office, "Notice of Allowance", in application No. 2,948,354, dated Aug. 6, 2019, 1 page.
Canada Claims in application No. PCT/US2015/029710, dated Aug. 2019, 2 pages.

\* cited by examiner

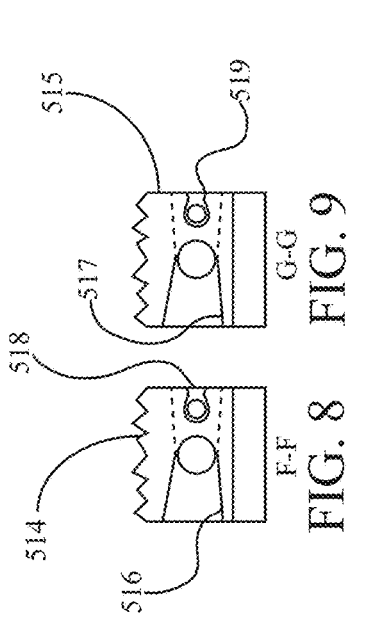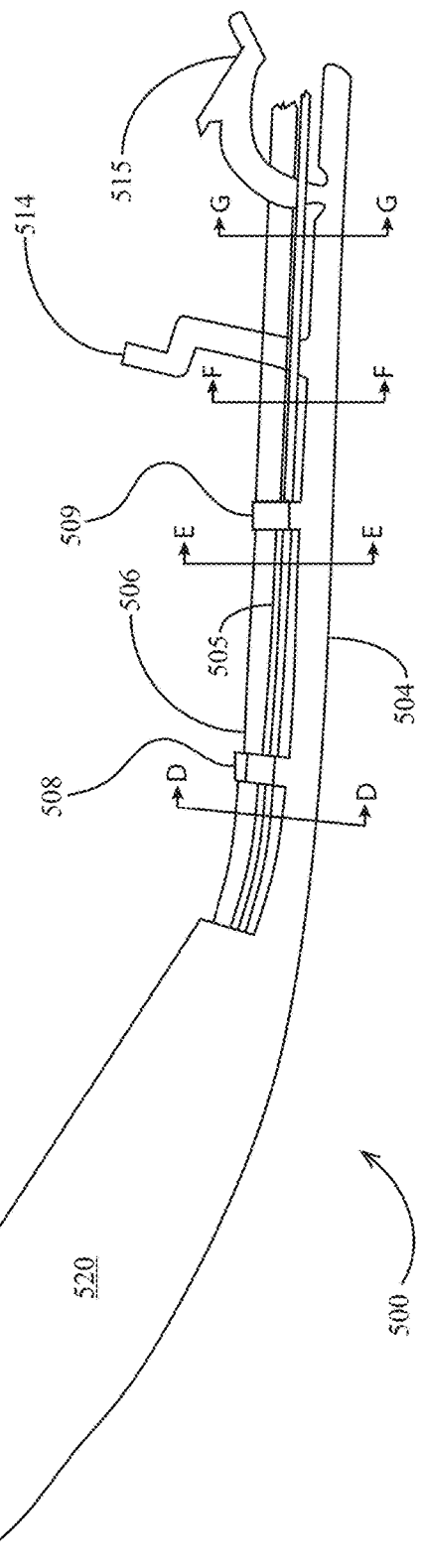

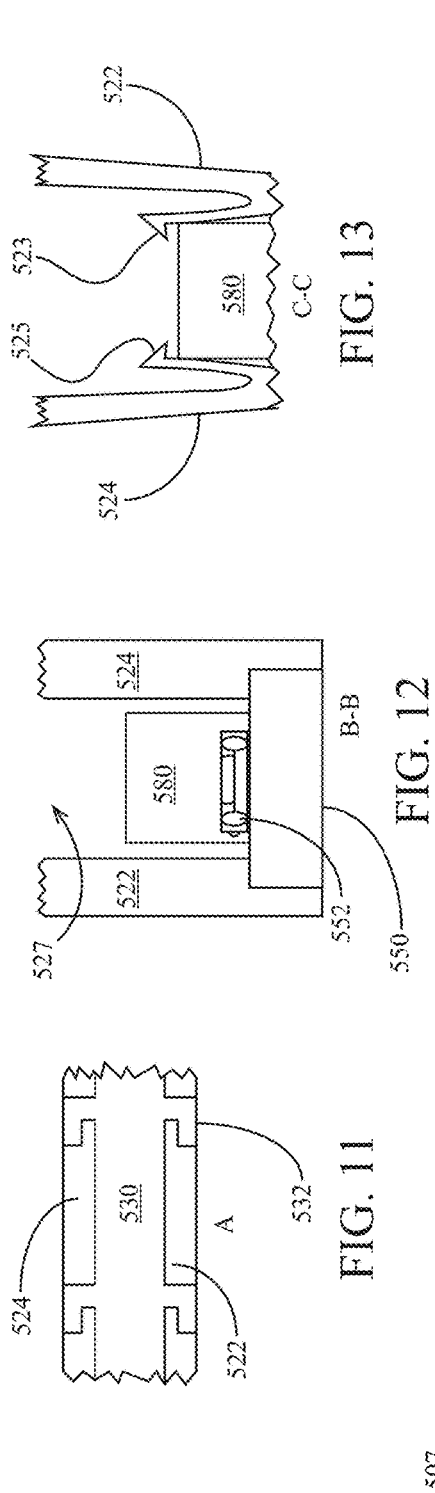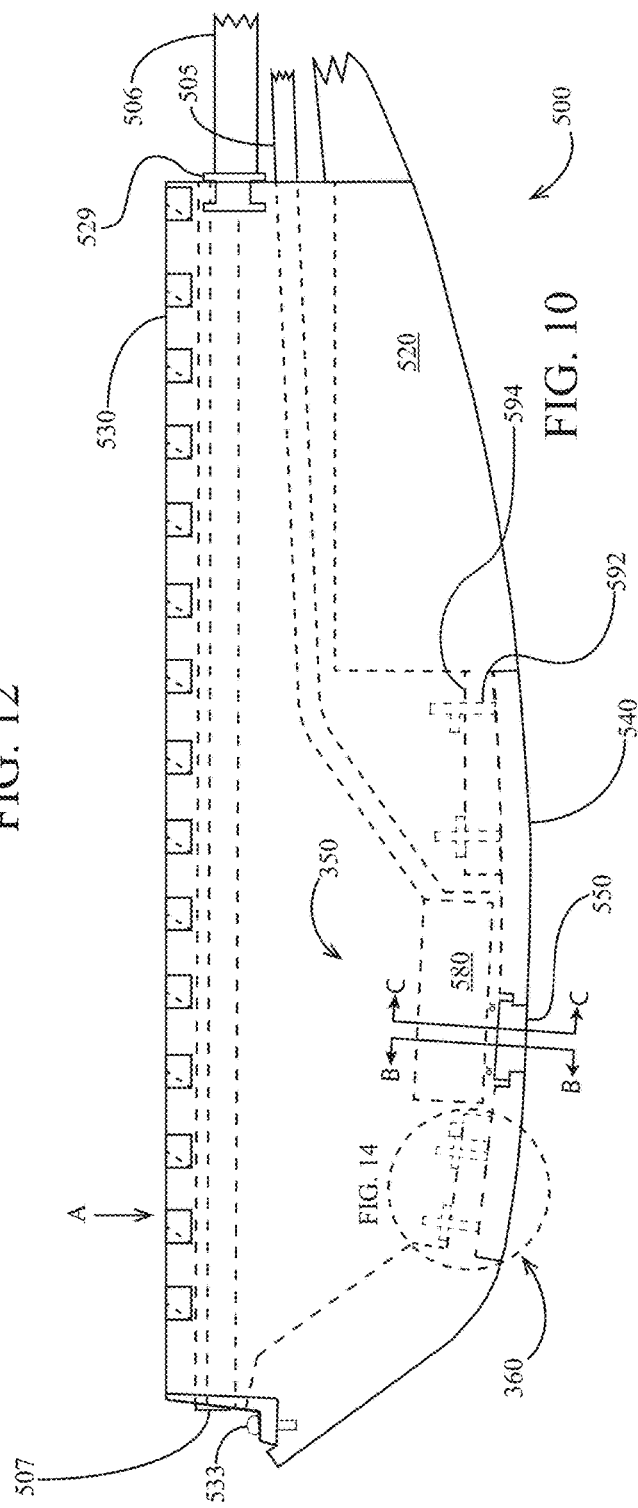

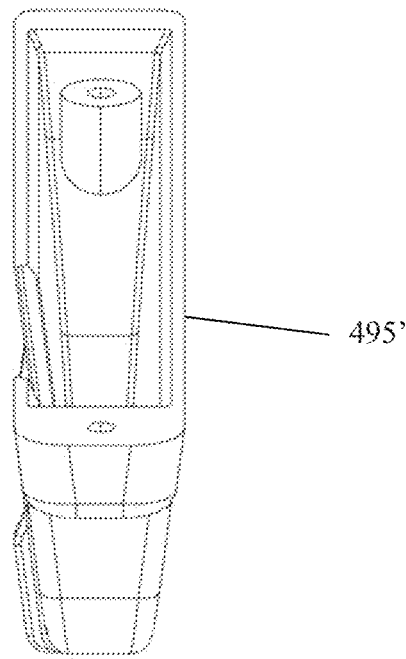
Figure 29A
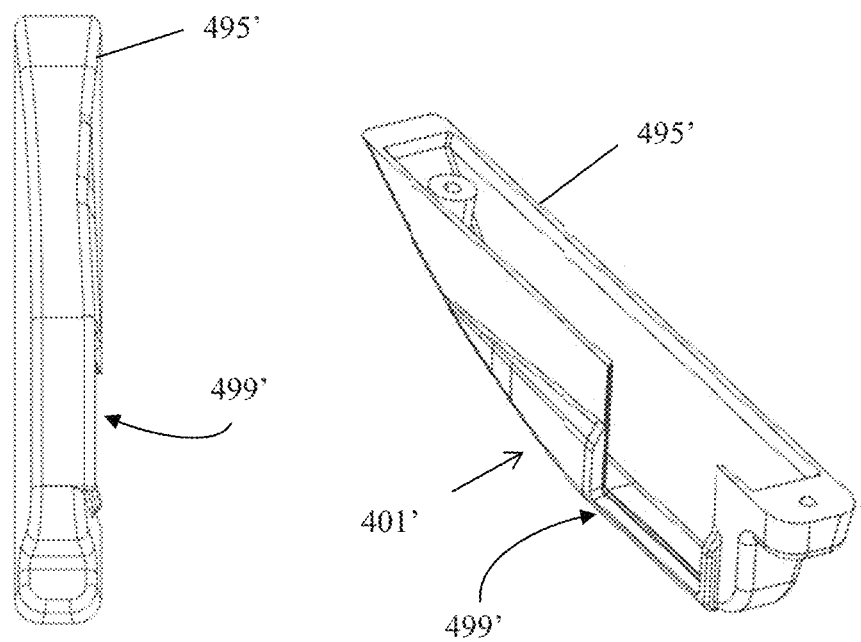
Figure 29C
Figure 29B

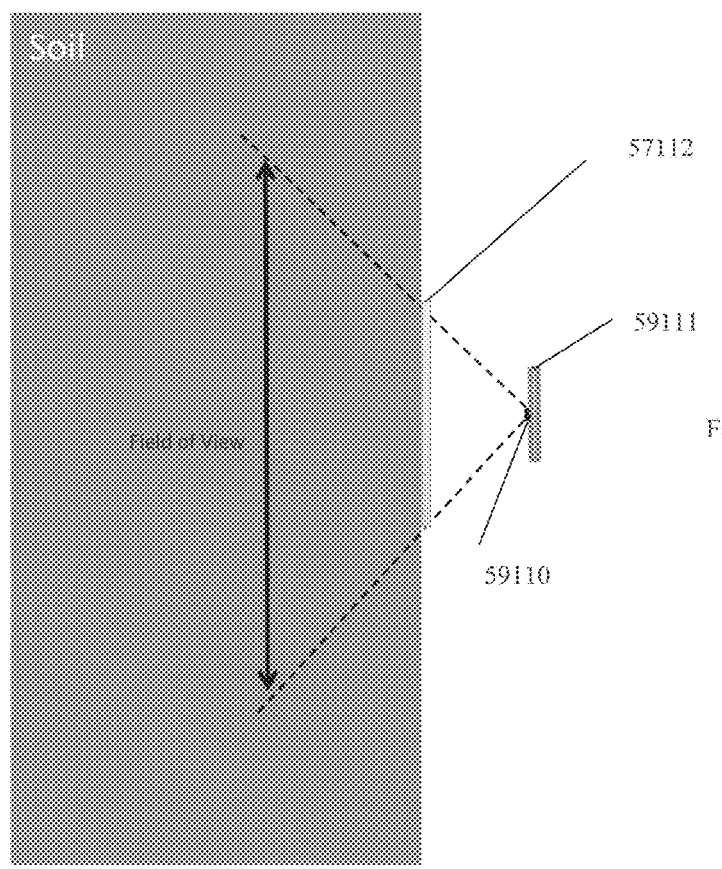
Figure 59
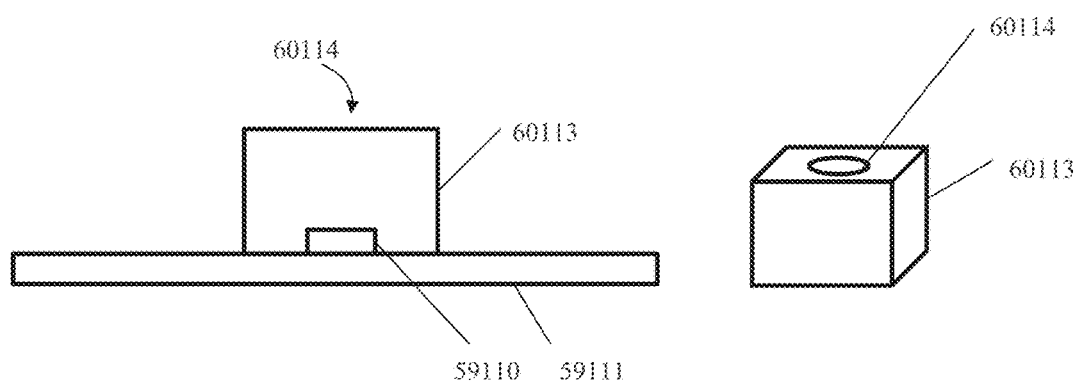
Figure 60A
Figure 60B

| | | | | | | | |
|---|---|---|---|---|---|---|---|
| Data Manager | | | | | | | |
| | Nitrogen | Planting | Practices | Soil | | | |
| Planting 1(4 Fields)<br>Crop Corn Product<br>Plant Date: 2016-04-12<br>ILU 112 \| Pop: 34000<br>[Edit] [Apply] | Planting 2(0 Fields)<br>Crop Corn Product<br>Plant Date: 2016-04-15<br>ILU 83 \| Pop: 34000<br>[Edit] [Apply] | Planting 3(0 Fields)<br>Crop Corn Product<br>Plant Date: 2016-04-13<br>ILU 83 \| Pop: 34000<br>[Edit] [Apply] | Planting 4(1 Fields)<br>Crop Corn Product<br>Plant Date: 2016-04-13<br>ILU 112 \| Pop: 34000<br>[Edit] [Apply] | | + <br>Add New<br>Planting Plan | | |
| | CROP | PLANTED ACRES | PRODUCT | RELATIVE MATURITY | TARGET YIELD | POPULATION(AVG) | PLA |
| ☐ Select All | | | | | | | |
| ☐ Ames, IA 1<br>Corn \| 100 \| Boone, IA | Corn | — | DMC82-M | 112 | 160 | 34000 | Apr |
| ☐ Austin, MN 1<br>Corn \| 100 \| Fredricks, MN | Corn | — | DMC82-M | 114 | 160 | 36000 | Apr |
| ☐ Boone, IN 1<br>Corn \| 100 \| Boone, IA | Corn | — | DMC82-M | 112 | 150 | 34000 | Apr |
| ☐ Champaign 1<br>Corn \| 100 \| Champaign, IL | Corn | — | — | 112 | 200 | 34000 | Apr |
| ☐ E Nebraska 1<br>Corn \| 100 \| Burt, NE | Corn | — | — | 112 | 160 | 34000 | Apr |

Figure 71

SYSTEMS, METHODS, AND APPARATUS FOR SOIL AND SEED MONITORING

CROSS-REFERENCE TO RELATED APPLICATIONS; BENEFIT CLAIM

This application claims the benefit under 35 U.S.C. § 119(e) of provisional application 62/436,342, filed Dec. 19, 2016, provisional application 62/446,254, filed Jan. 13, 2017, provisional application 62/482,116, filed Apr. 5, 2017 and provisional application 62/516,553, filed Jun. 7, 2017, the entire contents of which are hereby incorporated by reference as if fully set forth herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. ©2016-2017 The Climate Corporation.

FIELD OF THE DISCLOSURE

The present disclosure relates to systems, methods, and apparatus for agricultural soil and seed monitoring and control. The present disclosure additionally relates to a temperature sensor.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

In recent years, the availability of advanced location-specific agricultural application and measurement systems (used in so-called "precision farming" practices) has increased grower interest in determining spatial variations in soil properties and in varying input application variables (e.g., planting depth) in light of such variations. However, the available mechanisms for measuring properties such as temperature are either not effectively locally made throughout the field or are not made at the same time as an input (e.g. planting) operation.

Temperature sensors for measuring soil temperature while traversing a field are known from PCT Patent Application No. PCT/US2015/029710 (Publication No. WO2015171908), filed Jul. 5, 2015 and U.S. Application No. 62/482,116, filed Apr. 5, 2017, both of which are incorporated herein by reference in their entireties.

SUMMARY

The appended claims may serve as a summary of the present disclosure.

BRIEF DESCRIPTION OF THE DRAWINGS

In the drawings:

FIG. 5 is a side elevation view of another embodiment of a seed firmer having a plurality of firmer-mounted sensors.

FIG. 6 is a sectional view along section D-D of FIG. 5.

FIG. 7 is a sectional view along section E-E of FIG. 5.

FIG. 8 is a sectional view along section F-F of FIG. 5.

FIG. 9 is a sectional view along section G-G of FIG. 5.

FIG. 10 is a partially cutaway partial side view of the seed firmer of FIG. 5.

FIG. 11 is a view along direction A of FIG. 10.

FIG. 12 is a view along section B-B of FIG. 10.

FIG. 13 is a view along section C-C of FIG. 10.

FIG. 29A is a perspective view of a firmer base according to one embodiment.

FIG. 29B is a side perspective view of the firmer base of FIG. 29A.

FIG. 29C is a bottom view of the firmer base of FIG. 29A.

FIG. 59 illustrates an arrangement of a thermopile and window for a selected field of view according to one embodiment.

FIG. 60A illustrates a shroud disposed over the thermopile to constrain the field of view according to one embodiment.

FIG. 60B is a perspective view of the shroud of FIG. 60A.

FIG. 71 depicts an example embodiment of a spreadsheet view for data entry.

DETAILED DESCRIPTION

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure.

A soil sensing device is described herein. In certain embodiments, the soil sensing device is disposed in a seed firmer.

A thermopile for measuring temperature via infrared radiation is described herein. In one example, the thermopile is disposed in a body and senses infrared radiation through an infrared transparent window.

Depth Control and Soil Monitoring Systems

Figure 1:
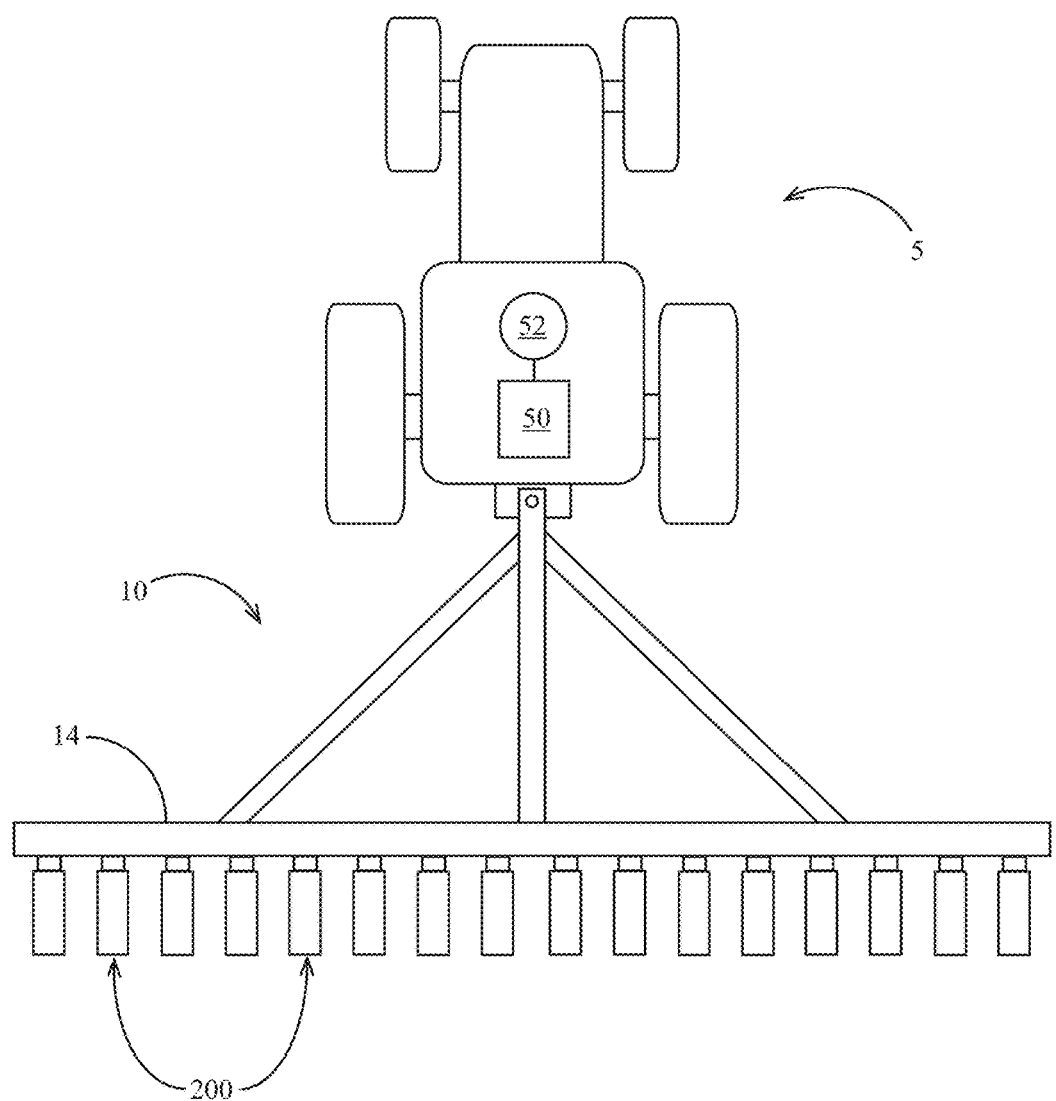
FIG. 1 is a top view of an embodiment of an agricultural planter.

Referring now to the drawings, wherein like reference numerals designate identical or corresponding parts throughout the several views, FIG. 1 illustrates a tractor 5 drawing an agricultural implement, e.g., a planter 10, comprising a toolbar 14 operatively supporting multiple row units 200. An implement monitor 50 preferably including a central processing unit ("CPU"), memory and graphical user interface ("GUI") (e.g., a touch-screen interface) is preferably located in the cab of the tractor 5. A global positioning system ("GPS") receiver 52 is preferably mounted to the tractor 5.

Figure 2:
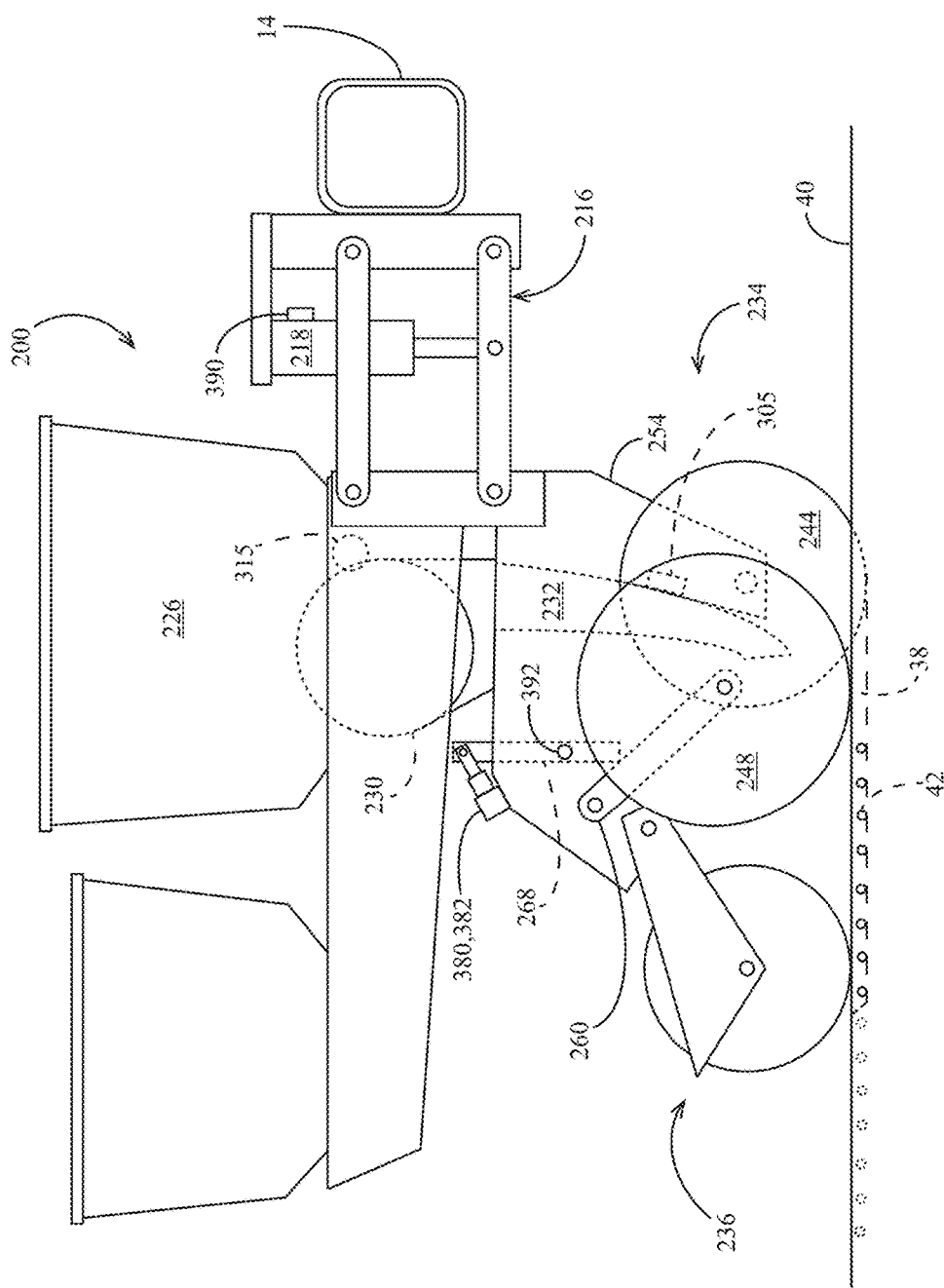
FIG. 2 is a side elevation view of an embodiment of a planter row unit.

Turing to FIG. 2, an embodiment is illustrated in which the row unit 200 is a planter row unit. The row unit 200 is preferably pivotally connected to the toolbar 14 by a parallel linkage 216. An actuator 218 is preferably disposed to apply lift and/or downforce on the row unit 200. A solenoid valve 390 is preferably in fluid communication with the actuator 218 for modifying the lift and/or downforce applied by the actuator. An opening system 234 preferably includes two opening discs 244 rollingly mounted to a downwardly-extending shank 254 and disposed to open a v-shaped trench 38 in the soil 40. A pair of gauge wheels 248 is pivotally supported by a pair of corresponding gauge wheel arms 260; the height of the gauge wheels 248 relative to the opener discs 244 sets the depth of the trench 38. A depth adjustment rocker 268 limits the upward travel of the gauge wheel arms 260 and thus the upward travel of the gauge wheels 248. A depth adjustment actuator 380 is preferably configured to modify a position of the depth adjustment rocker 268 and thus the height of the gauge wheels 248. The actuator 380 is preferably a linear actuator mounted to the row unit 200 and pivotally coupled to an upper end of the rocker 268. In some embodiments the depth adjustment actuator 380 comprises a device such as that disclosed in International Patent Application No. PCT/US2012/035585 ("the '585 application"), the disclosure of which is hereby incorporated herein by reference. An encoder 382 is preferably configured to generate a signal related to the linear extension of the actuator 380; it should be appreciated that the linear extension of the actuator 380 is related to the depth of the trench 38 when the gauge wheel arms 260 are in contact with the rocker 268. A downforce sensor 392 is preferably configured to generate a signal related to the amount of force imposed by the gauge wheels 248 on the soil 40; in some embodiments the downforce sensor 392 comprises an instrumented pin about which the rocker 268 is pivotally coupled to the row unit 200, such as those instrumented pins disclosed in Applicant's U.S. patent application Ser. No. 12/522,253 (Pub. No. US 2010/0180695), the disclosure of which is hereby incorporated herein by reference.

Continuing to refer to FIG. 2, a seed meter 230 such as that disclosed in Applicant's International Patent Application No. PCT/US2012/030192, the disclosure of which is hereby incorporated herein by reference, is preferably disposed to deposit seeds 42 from a hopper 226 into the trench 38, e.g., through a seed tube 232 disposed to guide the seeds toward the trench. In some embodiments, instead of a seed tube 232, a seed conveyor is implemented to convey seeds from the seed meter to the trench at a controlled rate of speed as disclosed in U.S. patent application Ser. No. 14/347,902 and/or U.S. Pat. No. 8,789,482, both of which are incorporated by reference herein. In such embodiments, a bracket such as that shown in FIG. 30 is preferably configured to mount the seed firmer to the shank via sidewalls extending laterally around the seed conveyor, such that the seed firmer is disposed behind the seed conveyor to firm seeds into the soil after they are deposited by the seed conveyor. In some embodiments, the meter is powered by an electric drive 315 configured to drive a seed disc within the seed meter. In other embodiments, the drive 315 may comprise a hydraulic drive configured to drive the seed disc. A seed sensor 305 (e.g., an optical or electromagnetic seed sensor configured to generate a signal indicating passage of a seed) is preferably mounted to the seed tube 232 and disposed to send light or electromagnetic waves across the path of seeds 42. A closing system 236 including one or more closing wheels is pivotally coupled to the row unit 200 and configured to close the trench 38.

Figure 3:
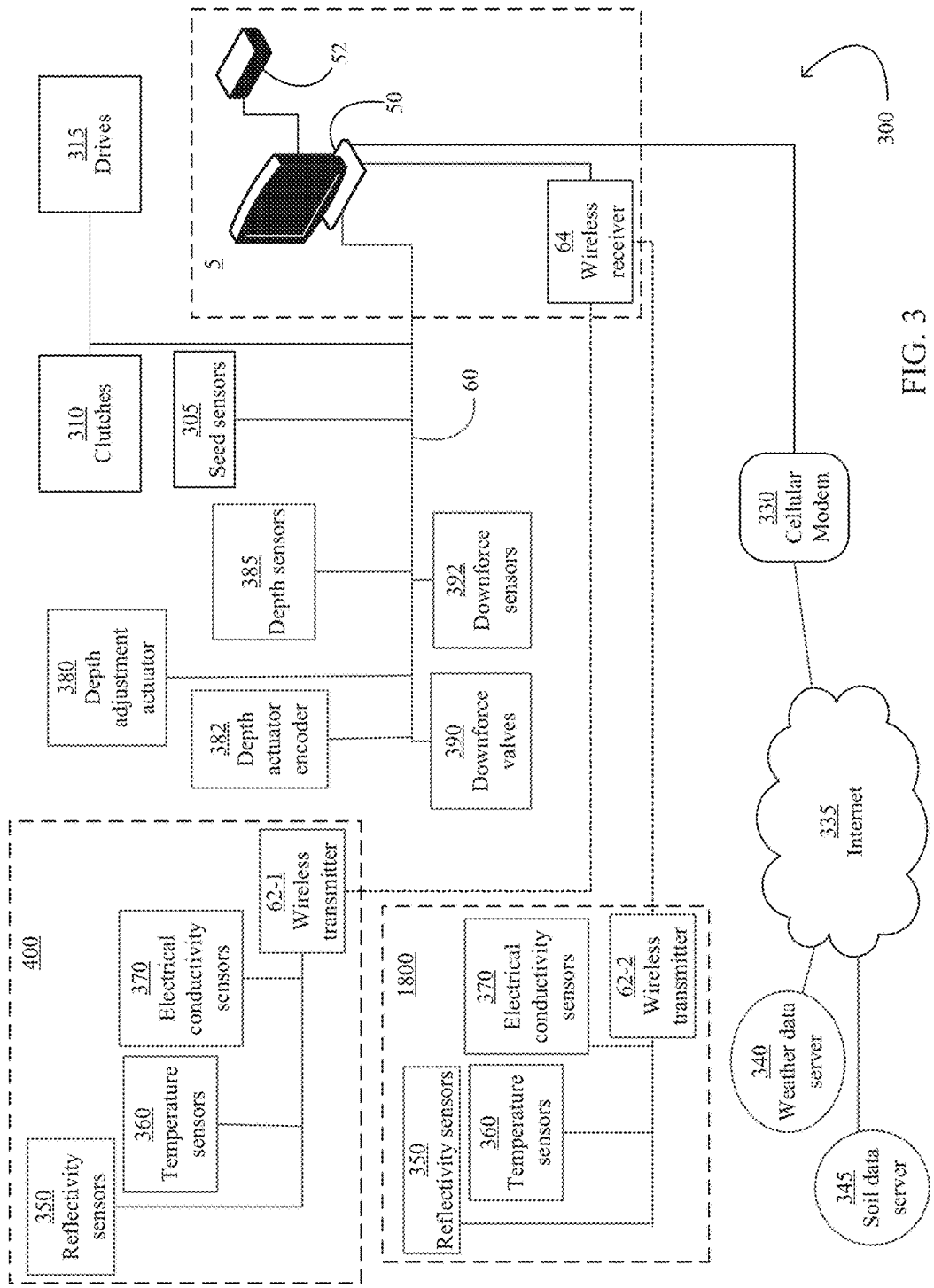
FIG. 3 schematically illustrates an embodiment of a soil monitoring system.

Turning to FIG. 3, a depth control and soil monitoring system 300 is schematically illustrated. The monitor 50 is preferably in data communication with components associated with each row unit 200 including the drives 315, the seed sensors 305, the GPS receiver 52, the downforce sensors 392, the valves 390, the depth adjustment actuator 380, and the depth actuator encoders 382. In some embodiments, particularly those in which each seed meter 230 is not driven by an individual drive 315, the monitor 50 is also preferably in data communication with clutches 310 configured to selectively operably couple the seed meter 230 to the drive 315.

Continuing to refer to FIG. 3, the monitor 50 is preferably in data communication with a cellular modem 330 or other component configured to place the monitor 50 in data communication with the Internet, indicated by reference numeral 335. The internet connection may comprise a wireless connection or a cellular connection. Via the Internet connection, the monitor 50 preferably receives data from a weather data server 340 and a soil data server 345. Via the Internet connection, the monitor 50 preferably transmits measurement data (e.g., measurements described herein) to a recommendation server (which may be the same server as the weather data server 340 and/or the soil data server 345) for storage and receives agronomic recommendations (e.g., planting recommendations such as planting depth, whether to plant, which fields to plant, which seed to plant, or which crop to plant) from a recommendation system stored on the server; in some embodiments, the recommendation system updates the planting recommendations based on the measurement data provided by the monitor 50.

Continuing to refer to FIG. 3, the monitor 50 is also preferably in data communication with one or more temperature sensors 360 mounted to the planter 10 and configured to generate a signal related to the temperature of soil being worked by the planter row units 200. The monitor 50 is preferably in data communication with one or more reflectivity sensors 350 mounted to the planter 10 and configured to generate a signal related to the reflectivity of soil being worked by the planter row units 200.

Referring to FIG. 3, the monitor 50 is preferably in data communication with one or more electrical conductivity sensors 365 mounted to the planter 10 and configured to generate a signal related to the temperature of soil being worked by the planter row units 200.

In some embodiments, a first set of reflectivity sensors 350, temperature sensors 360, and electrical conductivity sensors are mounted to a seed firmer 400 and disposed to measure reflectivity, temperature and electrical conductivity, respectively, of soil in the trench 38. In some embodiments, a second set of reflectivity sensors 350, temperature sensors 360, and electrical conductivity sensors 370 are mounted to a reference sensor assembly 1800 and disposed to measure reflectivity, temperature and electrical conductivity, respectively, of the soil, preferably at a depth different than the sensors on the seed firmer 400.

In some embodiments, a subset of the sensors are in data communication with the monitor 50 via a bus 60 (e.g., a CAN bus). In some embodiments, the sensors mounted to the seed firmer 400 and the reference sensor assembly 1800 are likewise in data communication with the monitor 50 via the bus 60. However, in the embodiment illustrated in FIG. 3, the sensors mounted to the seed firmer the sensors mounted to the seed firmer 400 and the reference sensor assembly 1800 are in data communication with the monitor 50 via a first wireless transmitter 62-1 and a second wireless transmitter 62-2, respectively. The wireless transmitters 62 at each row unit are preferably in data communication with a single wireless receiver 64 which is in turn in data communication with the monitor 50. The wireless receiver may be mounted to the toolbar 14 or in the cab of the tractor 5.

Soil Monitoring, Seed Monitoring and Seed Firming Apparatus

Figure 4A:
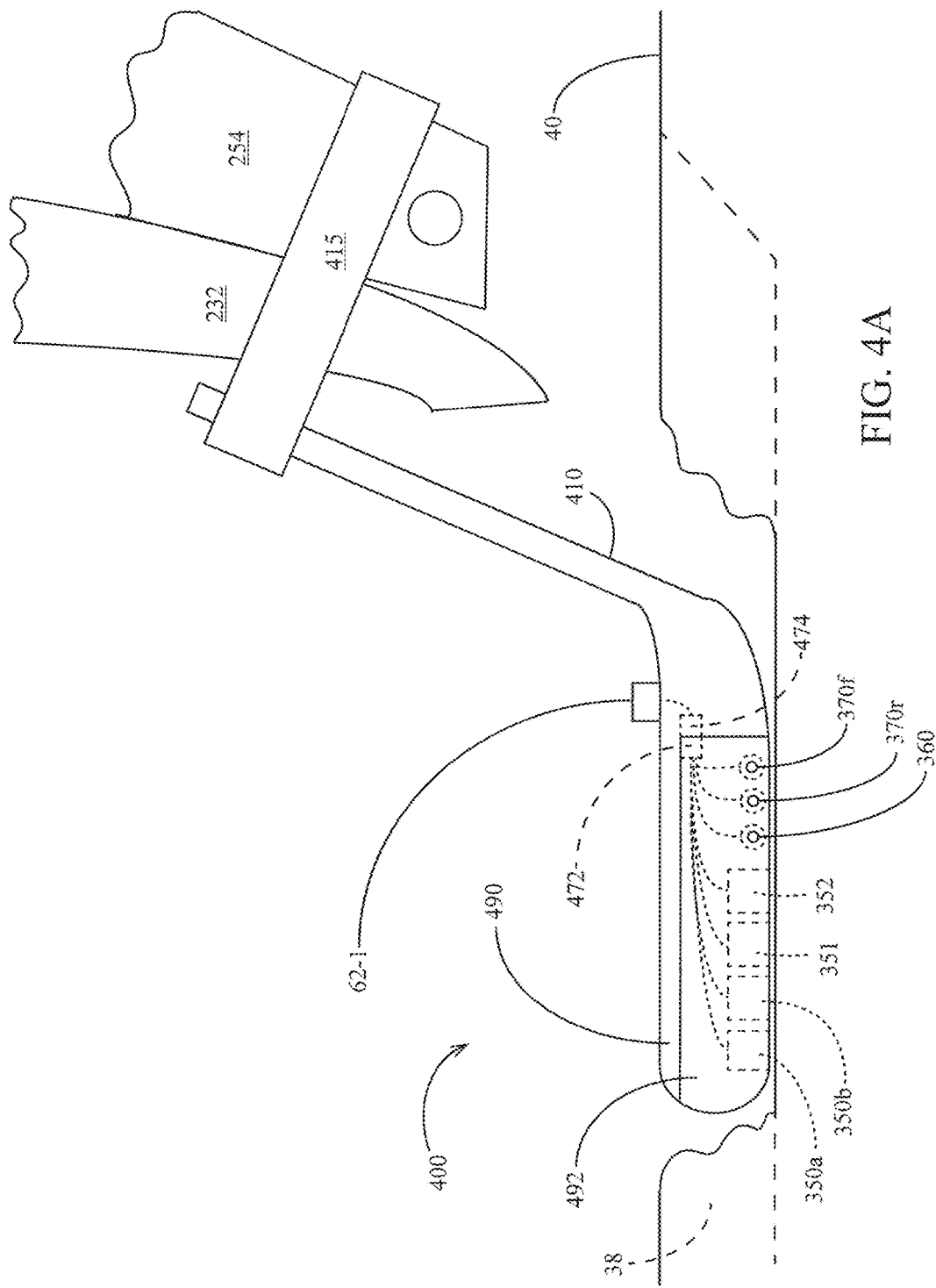
FIG. 4A is a side elevation view of an embodiment of a seed firmer having a plurality of firmer-mounted sensors.
Figure 4B:
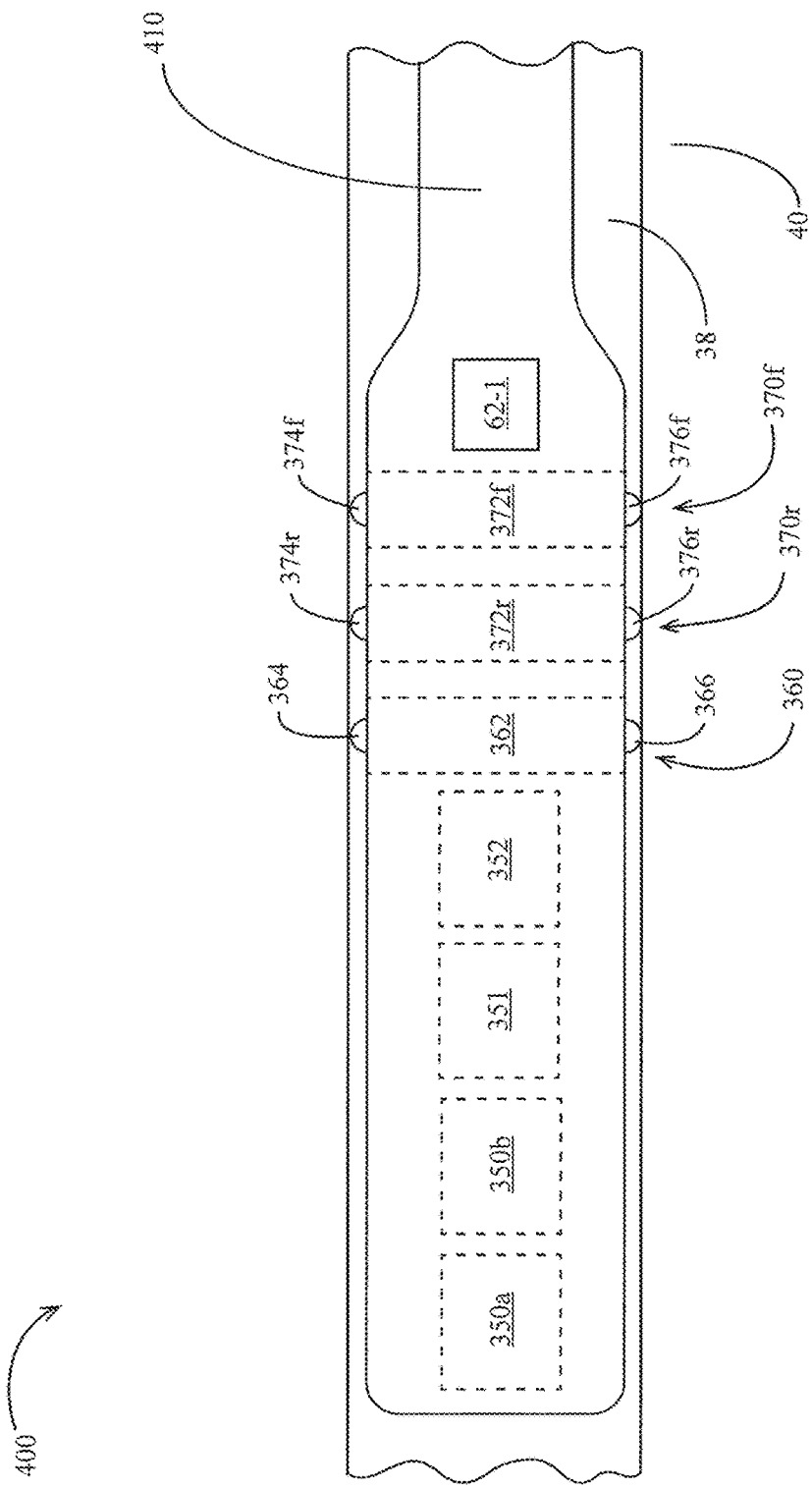
FIG. 4B is a plan view of the seed firmer of FIG. 4A.
Figure 4C:
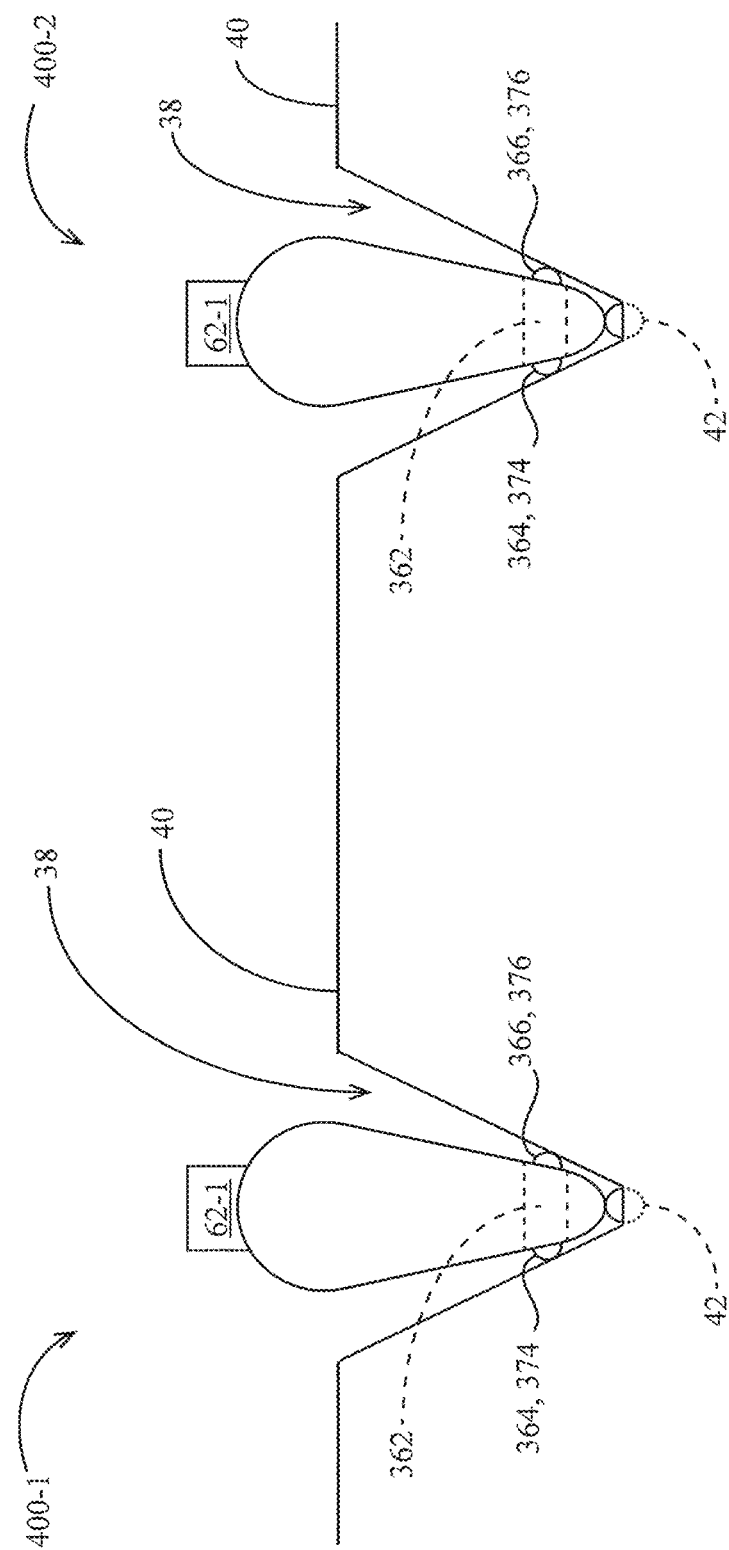
FIG. 4C is a rear elevation view of the seed firmer of FIG. 4A.
Figure 14:
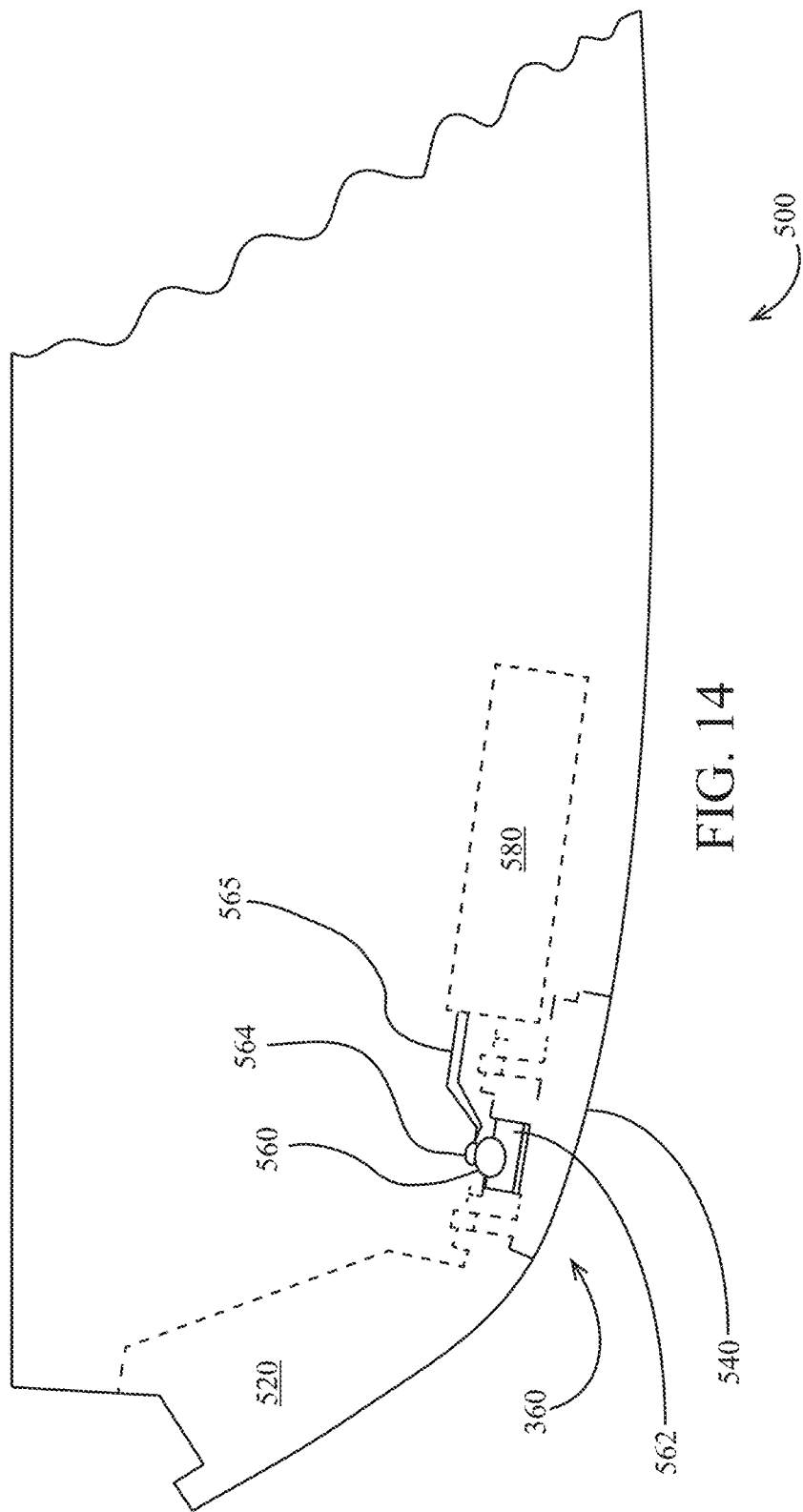
FIG. 14 is an enlarged partial cutaway view of the seed firmer of FIG. 5.

Turning to FIGS. 4A-4C, an embodiment of a seed firmer 400 is illustrated having a plurality of sensors for sensing soil characteristics. The seed firmer 400 preferably includes a flexible portion 410 mounted to the shank 254 and/or the seed tube 232 by a bracket 415. In some embodiments, the bracket 415 is similar to one of the bracket embodiments disclosed in U.S. Pat. No. 6,918,342, incorporated by reference herein. The seed firmer preferably includes a firmer body 490 disposed and configured to be received at least partially within v-shaped trench 38 and firm seeds 42 into the bottom of the trench. When the seed firmer 400 is lowered into the trench 38, the flexible portion 410 preferably urges the firmer body 490 into resilient engagement with the trench. In some embodiments the flexible portion 410 preferably includes an external or internal reinforcement as disclosed in PCT/US2013/066652, incorporated by reference herein. In some embodiments the firmer body 490 includes a removable portion 492; the removable portion 492 preferably slides into locking engagement with the remainder of the firmer body. The firmer body 490 (preferably including the portion of the firmer body engaging the soil, which in some embodiments comprises the removable portion 492) is preferably made of a material (or has an outer surface or coating) having hydrophobic and/or anti-stick properties, e.g. having a Teflon graphite coating and/or comprising a polymer having a hydrophobic material (e.g., silicone oil or polyether-ether-ketone) impregnated therein. Alternatively, the sensors can be disposed on the side of seed firmer 400 (not shown).

Returning to FIGS. 4A through 4C, the seed firmer 400 preferably includes a plurality of reflectivity sensors 350a, 350b. Each reflectivity sensor 350 is preferably disposed and configured to measure reflectivity of soil; in a preferred embodiment, the reflectivity sensor 350 is disposed to measure soil in the trench 38, and preferably at the bottom of the trench. The reflectivity sensor 350 preferably includes a lens disposed in the bottom of the firmer body 490 and disposed to engage the soil at the bottom of the trench 38. In some embodiments the reflectivity sensor 350 comprises one of the embodiments disclosed in U.S. Pat. No. 8,204,689 and/or U.S. Provisional Patent Application 61/824,975 ("the '975 application"), both of which are incorporated by reference herein. In various embodiments, the reflectivity sensor 350 is configured to measure reflectivity in the visible range (e.g., 400 and/or 600 nanometers), in the near-infrared range (e.g., 940 nanometers) and/or elsewhere the infrared range.

The seed firmer 400 may also include a capacitive moisture sensor 351 disposed and configured to measure capacitance moisture of the soil in the seed trench 38, and preferably at the bottom of trench 38.

The seed firmer 400 may also include an electronic tensiometer sensor 352 disposed and configured to measure soil moisture tension of the soil in the seed trench 38, and preferably at the bottom of trench 38.

Alternatively, soil moisture tension can be extrapolated from capacitive moisture measurements or from reflectivity measurements (such as at 1450 nm). This can be done using a soil water characteristic curve based on the soil type.

The seed firmer 400 may also include a temperature sensor 360. The temperature sensor 360 is preferably disposed and configured to measure temperature of soil; in a preferred embodiment, the temperature sensor is disposed to measure soil in the trench 38, preferably at or adjacent the bottom of the trench 38. The temperature sensor 360 preferably includes soil-engaging ears 364, 366 disposed to slidingly engage each side of the trench 38 as the planter traverses the field. The ears 364, 366 preferably engage the trench 38 at or adjacent to the bottom of the trench. The ears 364, 366 are preferably made of a thermally conductive material such as copper. The ears 364 are preferably fixed to and in thermal communication with a central portion 362 housed within the firmer body 490. The central portion 362 preferably comprises a thermally conductive material such as copper; in some embodiments the central portion 362 comprises a hollow copper rod. The central portion 362 is preferably in thermal communication with a thermocouple fixed to the central portion. In other embodiments, the temperature sensor 360 may comprise a non-contact temperature sensor such as an infrared thermometer. In some embodiments, other measurements made by the system 300 (e.g., reflectivity measurements, electrical conductivity measurements, and/or measurements derived from those measurements) are temperature-compensated using the temperature measurement made by the temperature sensor 360. The adjustment of the temperature-compensated measurement based on temperature is preferably carried out by consulting an empirical look-up table relating the temperature-compensated measurement to soil temperature. For example, the reflectivity measurement at a near-infrared wavelength may be increased (or in some examples, reduced) by 1% for every 1 degree Celsius in soil temperature above 10 degrees Celsius.

The seed firmer preferably includes a plurality of electrical conductivity sensors $370r$, $370f$. Each electrical conductivity sensor 370 is preferably disposed and configured to measure electrical conductivity of soil; in a preferred embodiment, the electrical conductivity sensor is disposed to measure electrical conductivity of soil in the trench 38, preferably at or adjacent the bottom of the trench 38. The electrical conductivity sensor 370 preferably includes soil-engaging ears 374, 376 disposed to slidingly engage each side of the trench 38 as the planter traverses the field. The ears 374, 376 preferably engage the trench 38 at or adjacent to the bottom of the trench. The ears 374, 376 are preferably made of an electrically conductive material such as copper. The ears 374 are preferably fixed to and in electrical communication with a central portion 372 housed within the firmer body 490. The central portion 372 preferably comprises an electrically conductive material such as copper; in some embodiments the central portion 372 comprises a copper rod. The central portion 372 is preferably in electrical communication with an electrical lead fixed to the central portion. The electrical conductivity sensor can measure the electrical conductivity within a trench by measuring the electrical current between soil-engaging ears 374 and 376.

Referring to FIG. 4B, in some embodiments the system 300 measures electrical conductivity of soil adjacent the trench 38 by measuring an electrical potential between the forward electrical conductivity sensor $370f$ and the rearward electrical conductivity sensor 370f. In other embodiments, the electrical conductivity sensors 370f, 370r may be disposed in longitudinally spaced relation on the bottom of the seed firmer in order to measure electrical conductivity at the bottom of the seed trench.

In other embodiments, the electrical conductivity sensors 370 comprise one or more ground-working or ground-contacting devices (e.g., discs or shanks) that contact the soil and are preferably electrically isolated from one another or from another voltage reference. The voltage potential between the sensors 370 or other voltage reference is preferably measured by the system 300. The voltage potential or another electrical conductivity value derived from the voltage potential is preferably and reported to the operator. The electrical conductivity value may also be associated with the GPS-reported position and used to generate a map of the spatial variation in electrical conductivity throughout the field. In some such embodiments, the electrical conductivity sensors may comprise one or more opening discs of a planter row unit, row cleaner wheels of a planter row unit, ground-contacting shanks of a planter, ground-contacting shoes depending from a planter shank, shanks of a tillage tool, or discs of a tillage tool. In some embodiments a first electrical conductivity sensor may comprise a component (e.g., disc or shank) of a first agricultural row unit while a second electrical conductivity sensor comprises a component (e.g., disc or shank) of a second agricultural row unit, such that electrical conductivity of soil extending transversely between the first and second row units is measured. It should be appreciated that at least one of the electrical conductivity sensors described herein is preferably electrically isolated from the other sensor or voltage reference. In one example, the electrical conductivity sensor is mounted to an implement (e.g., to the planter row unit or tillage tool) by being first mounted to an electrically insulating component (e.g., a component made from an electrically insulating material such as polyethylene, polyvinyl chloride, or a rubber-like polymer) which is in turn mounted to the implement.

Referring to FIG. 4C, in some embodiments the system 300 measures electrical conductivity of soil between two row units 200 having a first seed firmer 400-1 and a second seed firmer 400-2, respectively, by measuring an electrical potential between an electrical conductivity sensor on the first seed firmer 400-1 and an electrical conductivity sensor on the second seed firmer 400-2. In some such embodiments, the electrical conductivity sensor 370 may comprise a larger ground-engaging electrode (e.g., a seed firmer housing) comprised of metal or other conductive material. It should be appreciated that any of the electrical conductivity sensors described herein may measure conductivity by any of the following combinations: (1) between a first probe on a ground-engaging row unit component (e.g., on a seed firmer, a row cleaner wheel, an opening disc, a shoe, a shank, a frog, a coulter, or a closing wheel) and a second probe on the same ground-engaging row unit component of the same row unit; (2) between a first probe on a first ground-engaging row unit component (e.g., on a seed firmer, a row cleaner wheel, an opening disc, a shoe, a shank, a frog, a coulter, or a closing wheel) and a second probe on a second ground-engaging row unit component (e.g., on a seed firmer, a row cleaner wheel, an opening disc, a shoe, a shank, a frog, a coulter, or a closing wheel) of the same row unit; or (3) between a first probe on a first ground-engaging row unit component (e.g., on a seed firmer, a row cleaner wheel, an opening disc, a shoe, a shank, a frog, a coulter, or a closing wheel) on a first row unit and a second probe on a second ground-engaging row unit component (e.g., on a seed firmer, a row cleaner wheel, an opening disc, a shoe, a shank, a frog, a coulter, or a closing wheel) on a second row unit. Either or both of the row units described in combinations 1 through 3 above may comprise a planting row unit or another row unit (e.g., a tillage row unit or a dedicated measurement row unit) which may be mounted forward or rearward of the toolbar.

The reflectivity sensors 350, the temperature sensors 360, 360', 360", and the electrical conductivity sensors 370 (collectively, the "firmer-mounted sensors") are preferably in data communication with the monitor 50. In some embodiments, the firmer-mounted sensors are in data communication with the monitor 50 via a transceiver (e.g., a CAN transceiver) and the bus 60. In other embodiments, the firmer-mounted sensors are in data communication with the monitor 50 via wireless transmitter 62-1 (preferably mounted to the seed firmer) and wireless receiver 64. In some embodiments, the firmer-mounted sensors are in electrical communication with the wireless transmitter 62-1 (or the transceiver) via a multi-pin connector comprising a male coupler 472 and a female coupler 474. In firmer body embodiments having a removable portion 492, the male coupler 472 is preferably mounted to the removable portion and the female coupler 474 is preferably mounted to the remainder of the firmer body 190; the couplers 472, 474 are preferably disposed such that the couplers engage electrically as the removable portion is slidingly mounted to the firmer body.

Figure 19A:
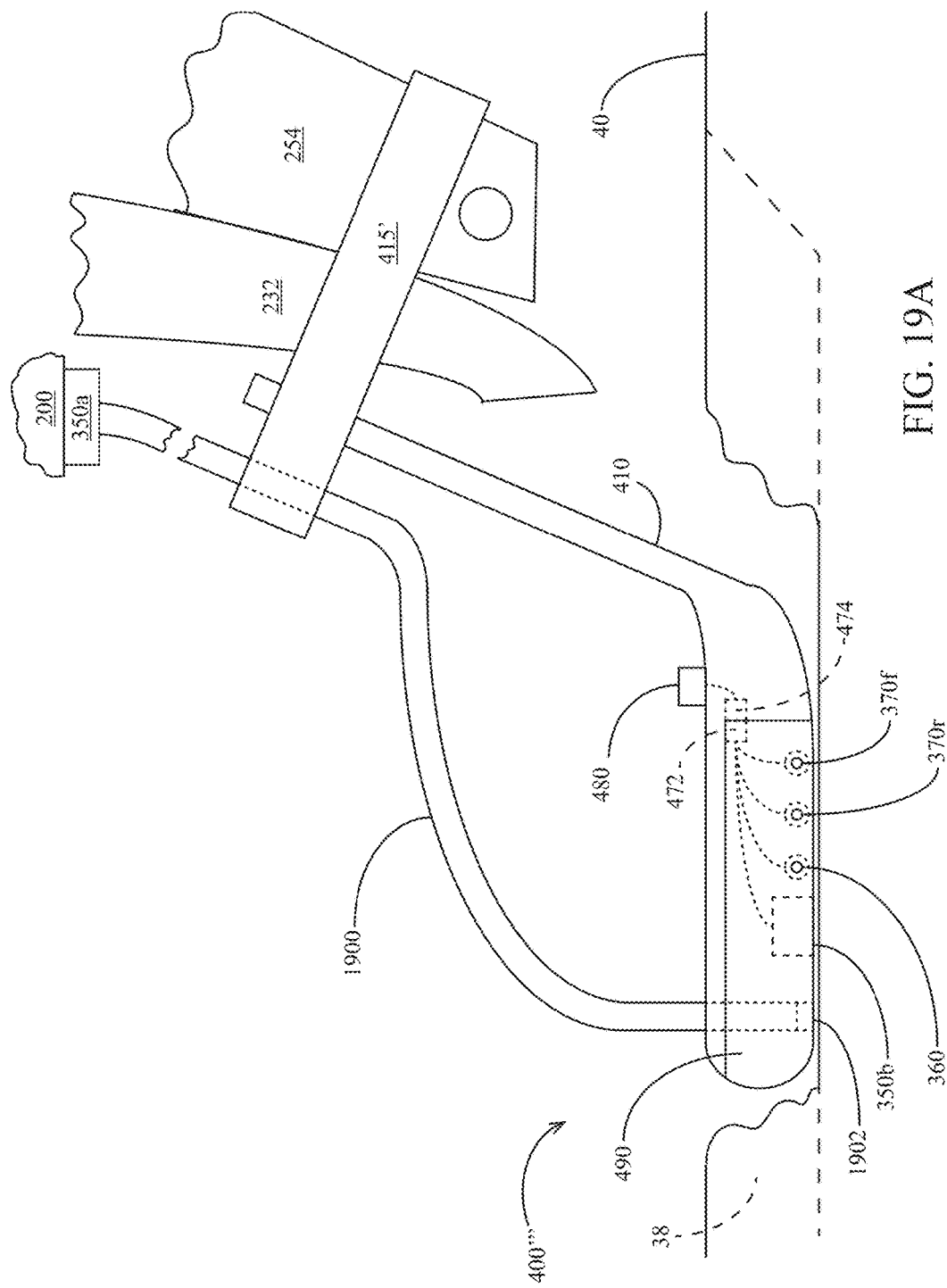
FIG. 19A is a side elevation view of an embodiment of an instrumented seed firmer incorporating fiber-optic cable transmitting light to a reflectivity sensor.
Figure 19B:
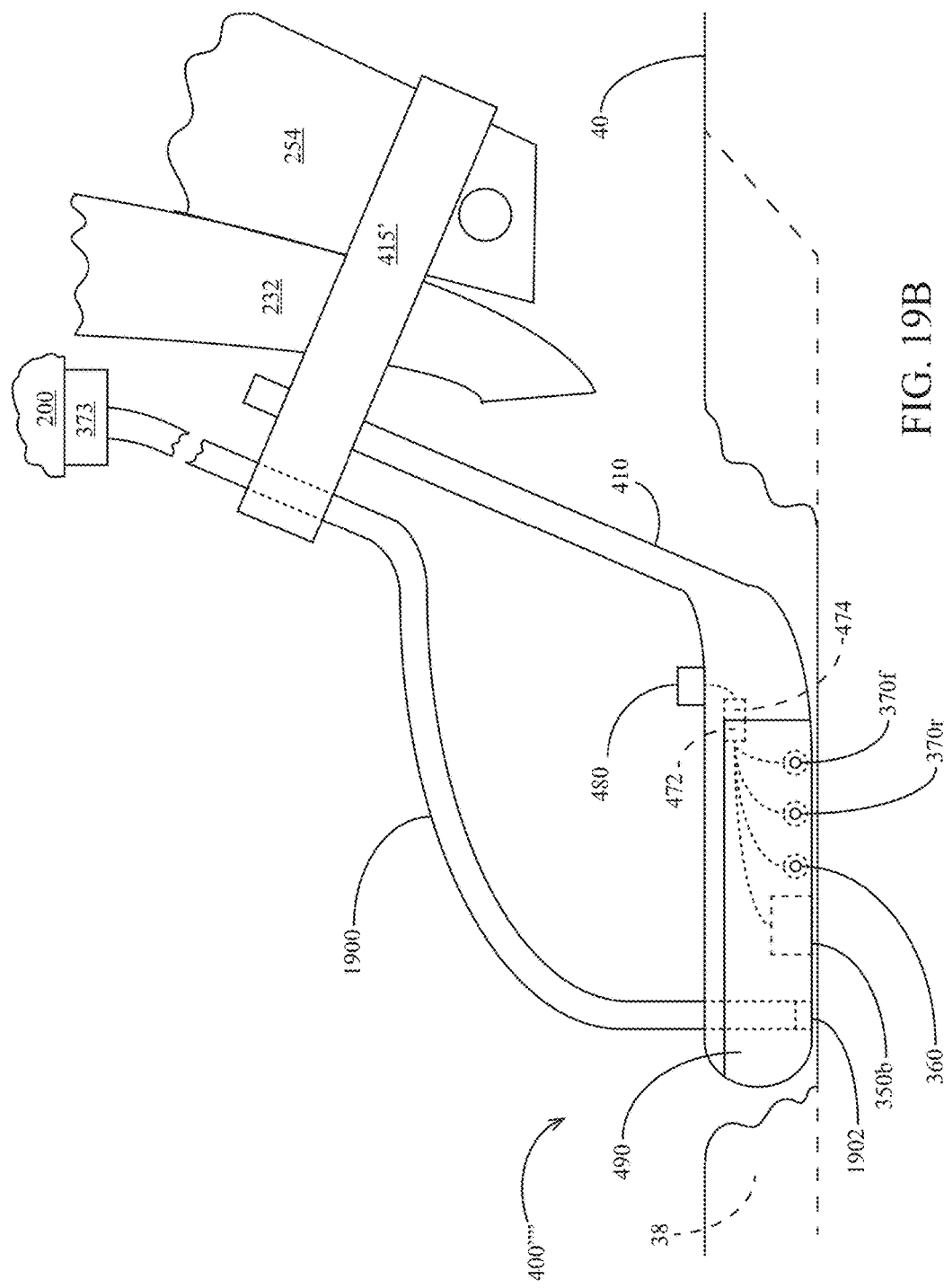
FIG. 19B is a side elevation view of an embodiment of an instrumented seed firmer incorporating fiber-optic cable transmitting light to a spectrometer.

Turning to FIG. 19A, another embodiment of the seed firmer 400''' is illustrated incorporating a fiber-optic cable 1900. The fiber-optic cable 1900 preferably terminates at a lens 1902 in the bottom of the firmer 400'''. The fiber-optic cable 1900 preferably extends to a reflectivity sensor 350a, which is preferably mounted separately from the seed firmer, e.g., elsewhere on the row unit 200. In operation, light reflected from the soil (preferably the bottom of trench 28) travels to the reflectivity sensor 350a via the fiber-optic cable 1900 such that the reflectivity sensor 350a is enabled to measure reflectivity of the soil at a location remote from the seed firmer 400'''. In other embodiments such as the seed firmer embodiment 400'''' illustrated in FIG. 19B, the fiber-optic cable extends to a spectrometer 373 configured to analyze light transmitted from the soil. The spectrometer 373 is preferably configured to analyze reflectivity at a spectrum of wavelengths. The spectrometer 373 is preferably in data communication with the monitor 50. The spectrometer 373 preferably comprises a fiber-optic spectrometer such as model no. USB4000 available from Ocean Optics, Inc. in Dunedin, Fla. In the embodiments 400''' and 400'''', a modified firmer bracket 415' is preferably configured to secure the fiber-optic cable 1900.

Figure 25:
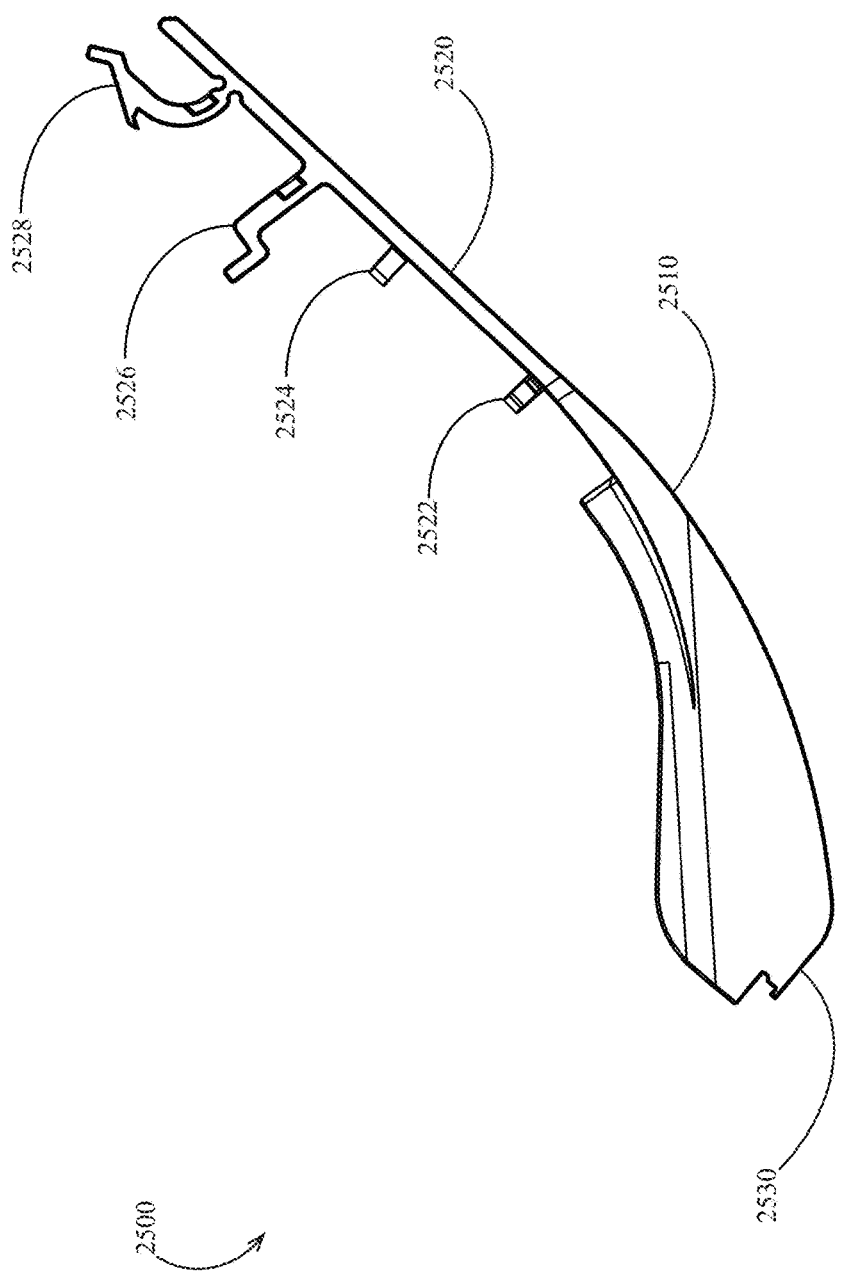
FIG. 25 is a side elevation view of another embodiment of a seed firmer.
Figure 26:
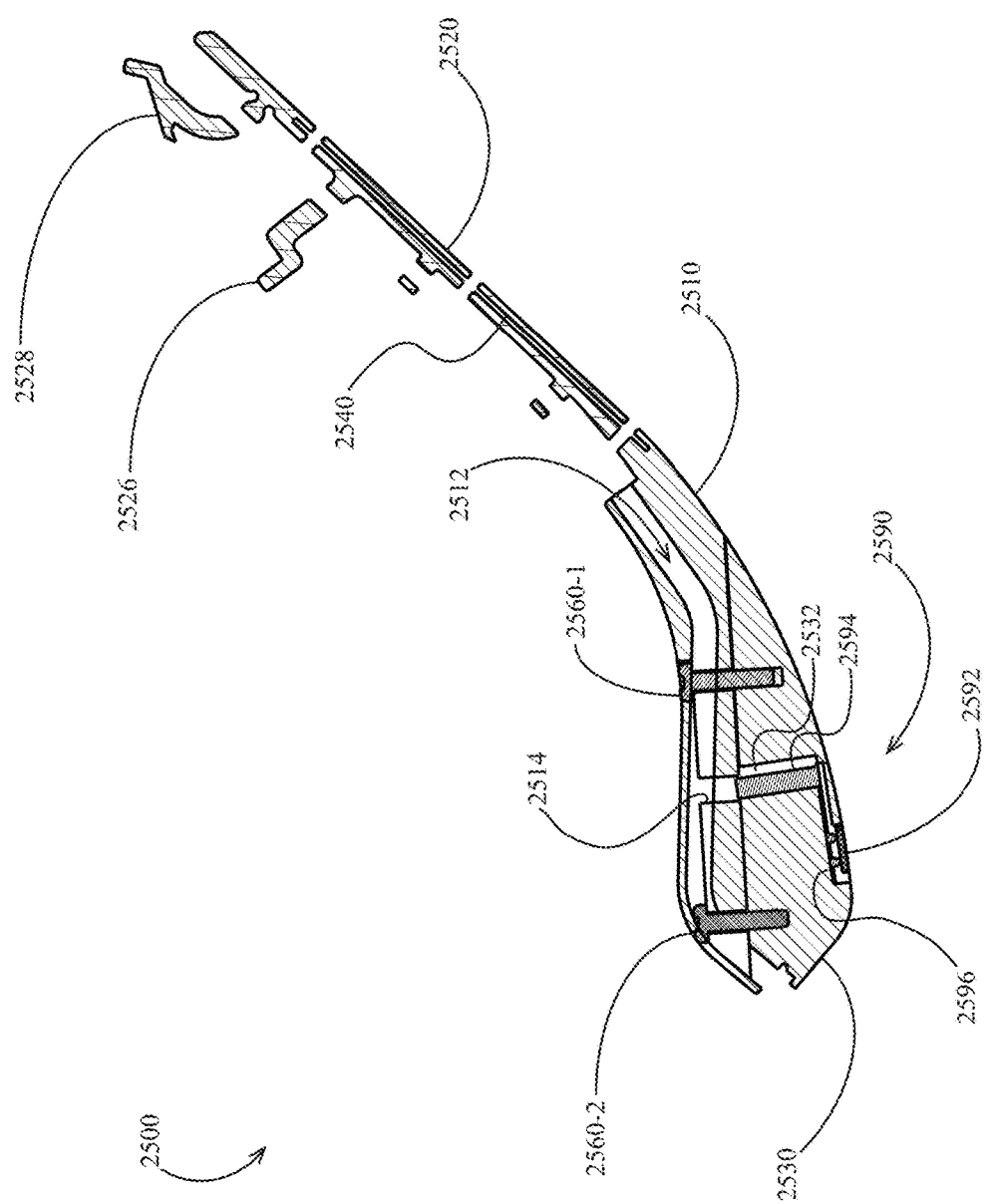
FIG. 26 is a side cross-sectional view of the seed firmer of FIG. 25.

Turning to FIGS. 25-26, another firmer embodiment 2500 is illustrated. The firmer 2500 includes an upper portion 2510 having a mounting portion 2520. The mounting portion 2520 is preferably stiffened by inclusion of a stiffening insert made of stiffer material than the mounting portion (e.g., the mounting portion may be made of plastic and the stiffening insert may be made of metal) in an inner cavity 2540 of the mounting portion 2520. The mounting portion 2520 preferably includes mounting tabs 2526, 2528 for releasably attaching the firmer 2500 to a bracket on the row unit. The mounting portion 2520 preferably includes mounting hooks 2522, 2524 for attaching a liquid application conduit (e.g., flexible tube) (not shown) to the firmer 2500. The upper portion 2510 preferably includes an internal cavity 2512 sized to receive the liquid application conduit. The internal cavity 2512 preferably includes a rearward aperture through which the liquid application conduit extends for dispensing liquid behind the firmer 2500. It should be appreciated that a plurality of liquid conduits may be inserted in the internal cavity 2512; additionally, a nozzle may be included at a terminal end of the conduit or conduits to redirect and/or split the flow of liquid applied in the trench behind the firmer 2500.

The firmer 2500 also preferably includes a ground-engaging portion 2530 mounted to the upper portion 2510. The ground-engaging portion 2530 may be removably mounted to the upper portion 2510; as illustrated, the ground-engaging portion is mounted to the upper portion by threaded screws 2560, but in other embodiments the ground-engaging portion may be installed and removed without the use of tools, e.g. by a slot-and-groove arrangement. The ground-engaging portion 2530 may also be permanently mounted to the upper portion 2510, e.g., by using rivets instead of screws 2560, or by molding the upper portion to the ground-engaging portion. The ground-engaging portion 2530 is preferably made of a material having greater wear-resistance than plastic such as metal (e.g., stainless steel or hardened white iron), may include a wear-resistant coating (or a non-stick coating as described herein), and may include a wear-resistant portion such as a tungsten carbide insert.

The ground-engaging portion 2530 preferably includes a sensor for detecting characteristics of the trench (e.g., soil moisture, soil organic matter, soil temperature, seed presence, seed spacing, percentage of seeds firmed, soil residue presence) such as a reflectivity sensor 2590, preferably housed in a cavity 2532 of the ground-engaging portion. The reflectivity sensor preferably includes a sensor circuit board 2596 having a sensor disposed to receive reflected light from the trench through a transparent window 2592. The transparent window 2592 is preferably mounted flush with a lower surface of the ground-engaging portion such that soil flows underneath the window without building up over the window or along an edge thereof. An electrical connection 2594 preferably connects the sensor circuit board 2596 to a wire or bus (not shown) placing the sensor circuit board in data communication with the monitor 50.

Turning to FIGS. 5-14, another seed firmer embodiment 500 is illustrated. A flexible portion 504 is preferably configured to resiliently press a firmer body 520 into the seed trench 38. Mounting tabs 514, 515 releasably couple the flexible portion 504 to the firmer bracket 415, preferably as described in the '585 application.

A flexible liquid conduit 506 preferably conducts liquid (e.g., liquid fertilizer) from a container to an outlet 507 for depositing in or adjacent to the trench 38. The conduit 506 preferably extends through the firmer body 520 between the outlet 507 and a fitting 529 which preferably constrains the conduit 506 from sliding relative to the firmer body 520. The portion of the conduit may extend through an aperture formed in the firmer body 520 or (as illustrated) through a channel covered by a removable cap 530. The cap 530 preferably engages sidewalls 522, 524 of the firmer body 520 by hooked tabs 532. Hooked tabs 532 preferably retain sidewalls 522, 524 from warping outward in addition to retaining the cap 530 on the firmer body 520. A screw 533 also preferably retains the cap 530 on the firmer body 520.

The conduit 506 is preferably retained to the flexible portion 504 of the seed firmer 500 by mounting hooks 508, 509 and by the mounting tabs 514, 515. The conduit 506 is preferably resiliently grasped by arms 512, 513 of the mounting hooks 508, 509 respectively. The conduit 506 is preferably received in slots 516, 517 of mounting tabs 514, 515, respectively.

A harness 505 preferably comprises a wire or plurality of wires in electrical communication with the firmer-mounted sensors described below. The harness is preferably received in slots 510, 511 of the mounting hooks 508, 509 and additionally retained in place by the conduit 506. The harness 505 is preferably grasped by slots 518, 519 of the mounting tabs 514, 515, respectively; the harness 505 is preferably pressed through a resilient opening of each slot 518, 519 and the resilient opening returns into place so that the slots retain the harness 505 unless the harness is forcibly removed.

In some embodiments the lowermost trench-engaging portion of the seed firmer 500 comprises a plate 540. The plate 540 may comprise a different material and/or a material having different properties from the remainder of the firmer body 520; for example, the plate 540 may have a greater hardness than the remainder of the firmer body 520 and may comprise powder metal. In some embodiments, the entire firmer body 520 is made of a relatively hard material such as powder metal. In an installment phase, the plate 540 is mounted to the remainder of the firmer body 520, e.g., by rods 592 fixed to plate 540 and secured to the remainder of the firmer body by snap rings 594; it should be appreciated that the plate may be either removably mounted or permanently mounted to the remainder of the firmer body.

The seed firmer 500 is preferably configured to removably receive a reflectivity sensor 350 within a cavity 527 within the firmer body 520. In a preferred embodiment, the reflectivity sensor 350 is removably installed in the seed firmer 500 by sliding the reflectivity sensor 350 into the cavity 527 until flexible tabs 525, 523 snap into place, securing the reflectivity sensor 350 in place until the flexible tabs are bent out of the way for removal of the reflectivity sensor. The reflectivity sensor 350 may be configured to perform any of the measurements described above with respect to the reflectivity sensor of seed firmer 400. The reflectivity sensor 350 preferably comprises a circuit board 580 (in some embodiments an over-molded printed circuit board). The reflectivity sensor 350 preferably detects light transmitted through a lens 550 having a lower surface coextensive with the surrounding lower surface of the firmer body 520 such that soil and seeds are not dragged by the lens. In embodiments having a plate 540, the bottom surface of the lens 550 is preferably coextensive with a bottom surface of the plate 540. The lens 550 is preferably a transparent material such as sapphire. The interface between the circuit board 580 and the lens 550 is preferably protected from dust and debris; in the illustrated embodiment the interface is protected by an O-ring 552, while in other embodiments the interface is protected by a potting compound. In a preferred embodiment, the lens 550 is mounted to the circuit board 580 and the lens slides into place within the lowermost surface of the firmer body 520 (and/or the plate 540) when the reflectivity sensor 350 is installed. In such embodiments, the flexible tabs 523, 525 preferably lock the reflectivity sensor into a position wherein the lens 550 is coextensive with the lowermost surface of the firmer body 520.

The seed firmer 500 preferably includes a temperature sensor 360. The temperature sensor 360 preferably comprises a probe 560. The probe 560 preferably comprises a thermo-conductive rod (e.g., a copper rod) extending through the width of the firmer body 500 and having opposing ends extending from the firmer body 500 to contact either side of the trench 38. The temperature sensor 360 preferably also comprises a resistance temperature detector ("RTD") 564 fixed to (e.g., screwed into a threaded hole in) the probe 560; the RTD is preferably in electrical communication with the circuit board 580 via an electrical lead 585; the circuit board 580 is preferably configured to process both reflectivity and temperature measurements and is preferably in electrical communication with the harness 505. In embodiments in which the plate 540 and/or the remainder of the firmer body 520 comprise a thermally conductive material, an insulating material 562 preferably supports the probe 560 such that temperature changes in the probe are minimally affected by contact with the firmer body; in such embodiments the probe 560 is preferably primarily surrounded by air in the interior of the firmer body 520 and the insulating material 562 (or firmer body) preferably contacts a minimal surface area of the probe. In some embodiments the insulating material comprises a low-conductivity plastic such as polystyrene or polypropylene.

Figure 15:
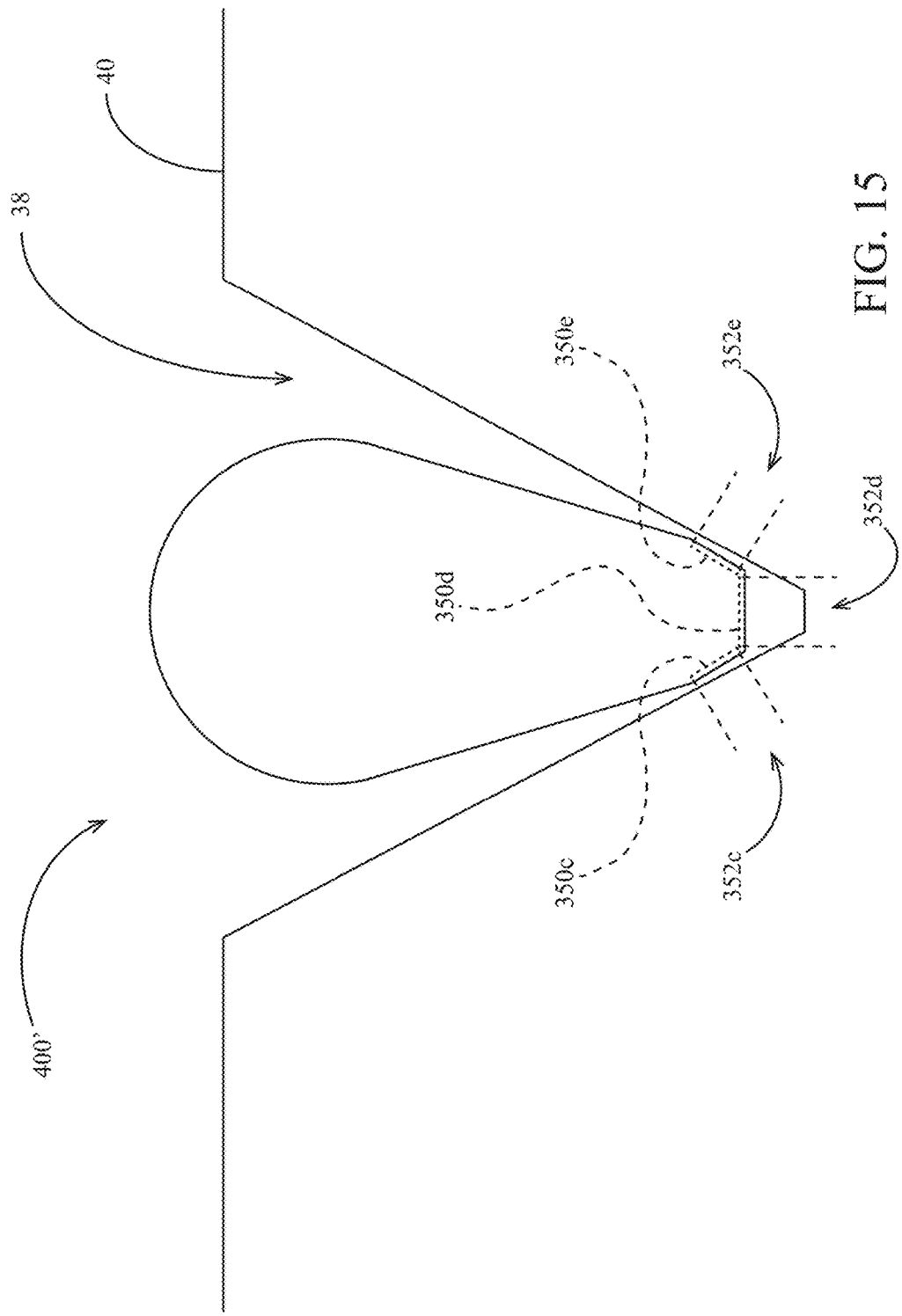
FIG. 15 is a rear view of another embodiment of a seed firmer.

Turning to FIG. 15, another embodiment 400' of the seed firmer is illustrated having a plurality of reflectivity sensors 350. Reflectivity sensors 350c, 350d and 350e are disposed to measure reflectivity of regions 352c, 352d and 352e, respectively, at and adjacent to the bottom of the trench 38. The regions 352c, 352d and 352e preferably constitute a substantially contiguous region preferably including all or substantially the entire portion of the trench in which seed rests after falling into the trench by gravity. In other embodiments, a plurality of temperature and/or electrical conductivity sensors are disposed to measure a larger, preferably substantially contiguous region.

Figure 16:
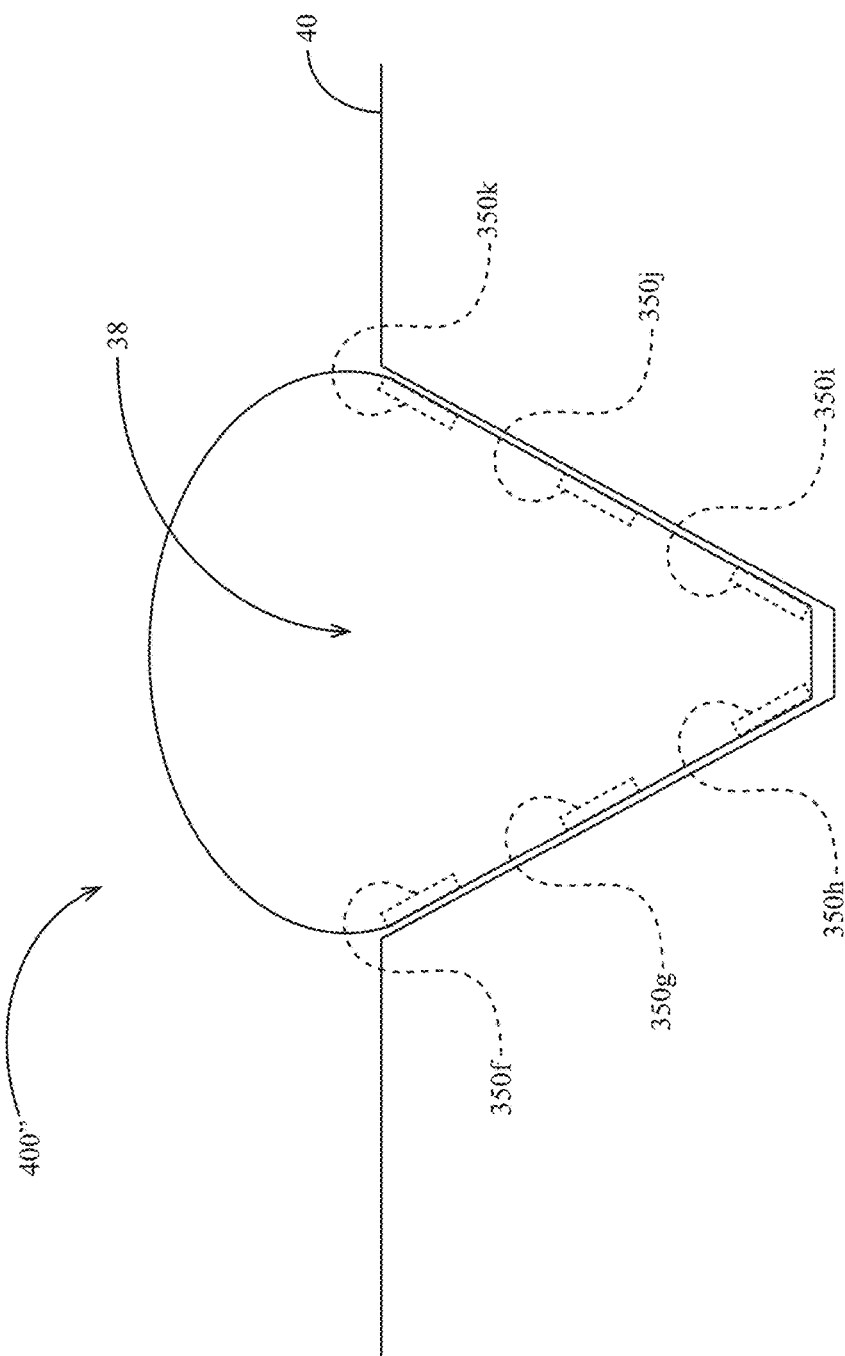
FIG. 16 is a rear view of still another embodiment of a seed firmer.

Turning to FIG. 16, another embodiment of a seed firmer 400" is illustrated having a plurality of reflectivity sensors 350 disposed to measure at either side of the trench 38 at various depths within in the trench. The reflectivity sensors 350f, 350k are disposed to measure reflectivity at or adjacent to the top of the trench 38. The reflectivity sensors 350h, 350i are disposed to measure reflectivity at or adjacent to the bottom of the trench 38. The reflectivity sensors 350g, 350j are disposed to measure reflectivity at an intermediate depth of the trench 38, e.g., at half the depth of the trench. It should be appreciated that in order to effectively make soil measurements at a depth at an intermediate depth of the trench, it is desirable to modify the shape of the seed firmer such that the sidewalls of the seed firmer engage the sides of the trench at an intermediate trench depth. Likewise, it should be appreciated that in order to effectively make soil measurements at a depth near the top of the trench (i.e., at or near the soil surface 40), it is desirable to modify the shape of the seed firmer such that the sidewalls of the seed firmer engage the sides of the trench at or near the top of the trench. In other embodiments, a plurality of temperature and/or electrical conductivity sensors are disposed to measure temperature and/or electrical conductivity, respectively, of soil at a plurality of depths within the trench 38.

Figure 18:
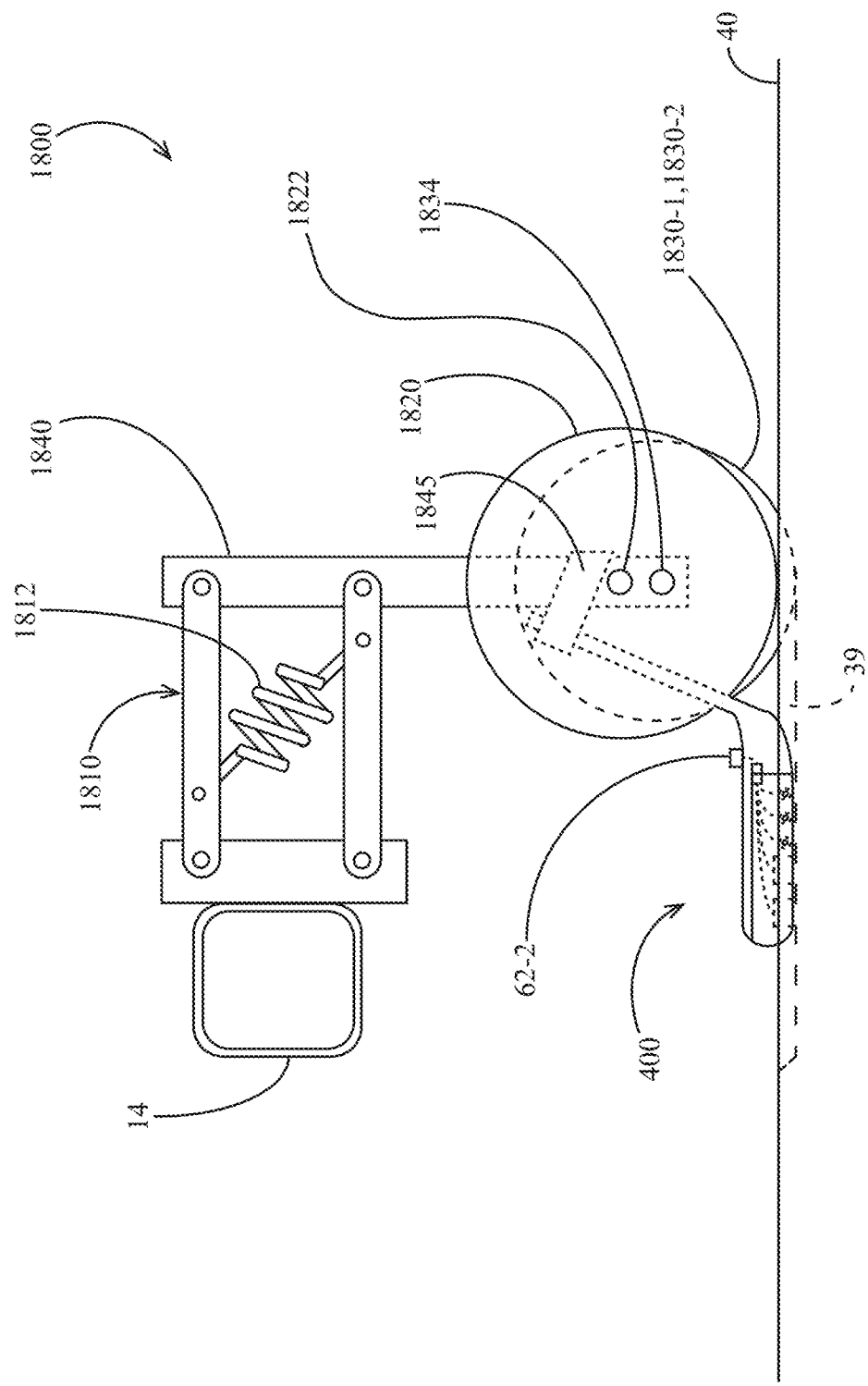
FIG. 18 is a side elevation view of an embodiment of a reference sensor.

As described above with respect to the system 300, in some embodiments a second set of reflectivity sensors 350, temperature sensors 360, and electrical conductivity sensors 370 are mounted to a reference sensor assembly 1800. One such embodiment is illustrated in FIG. 18, in which the reference sensor assembly opens a trench 39 in which a seed firmer 400 having firmer-mounted sensors is resiliently engaged in order to sense the soil characteristics of the bottom of the trench 39. The trench 39 is preferably at a shallow depth (e.g., between ⅛ and ½ inch) or at a deep depth (e.g., between 3 and 5 inches). The trench is preferably opened by a pair of opening discs 1830-1, 1830-2 disposed to open a v-shaped trench in the soil 40 and rotating about lower hubs 1834. The depth of the trench is preferably set by one or more gauge wheels 1820 rotating about upper hubs 1822. The upper and lower hubs are preferably fixedly mounted to a shank 1840. The seed firmer is preferably mounted to the shank 1840 by a firmer bracket 1845. The shank 1840 is preferably mounted to the toolbar 14. In some embodiments, the shank 1840 is mounted to the toolbar 14 by a parallel arm arrangement 1810 for vertical movement relative to the toolbar; in some such embodiments, the shank is resiliently biased toward the soil by an adjustable spring 1812 (or other downforce applicator). In the illustrated embodiment the shank 1840 is mounted forward of the toolbar 14; in other embodiments, the shank may be mounted rearward of the toolbar 14. In other embodiments, the firmer 400 may be mounted to the row unit shank 254, to a closing wheel assembly, or to a row cleaner assembly.

Figure 23:
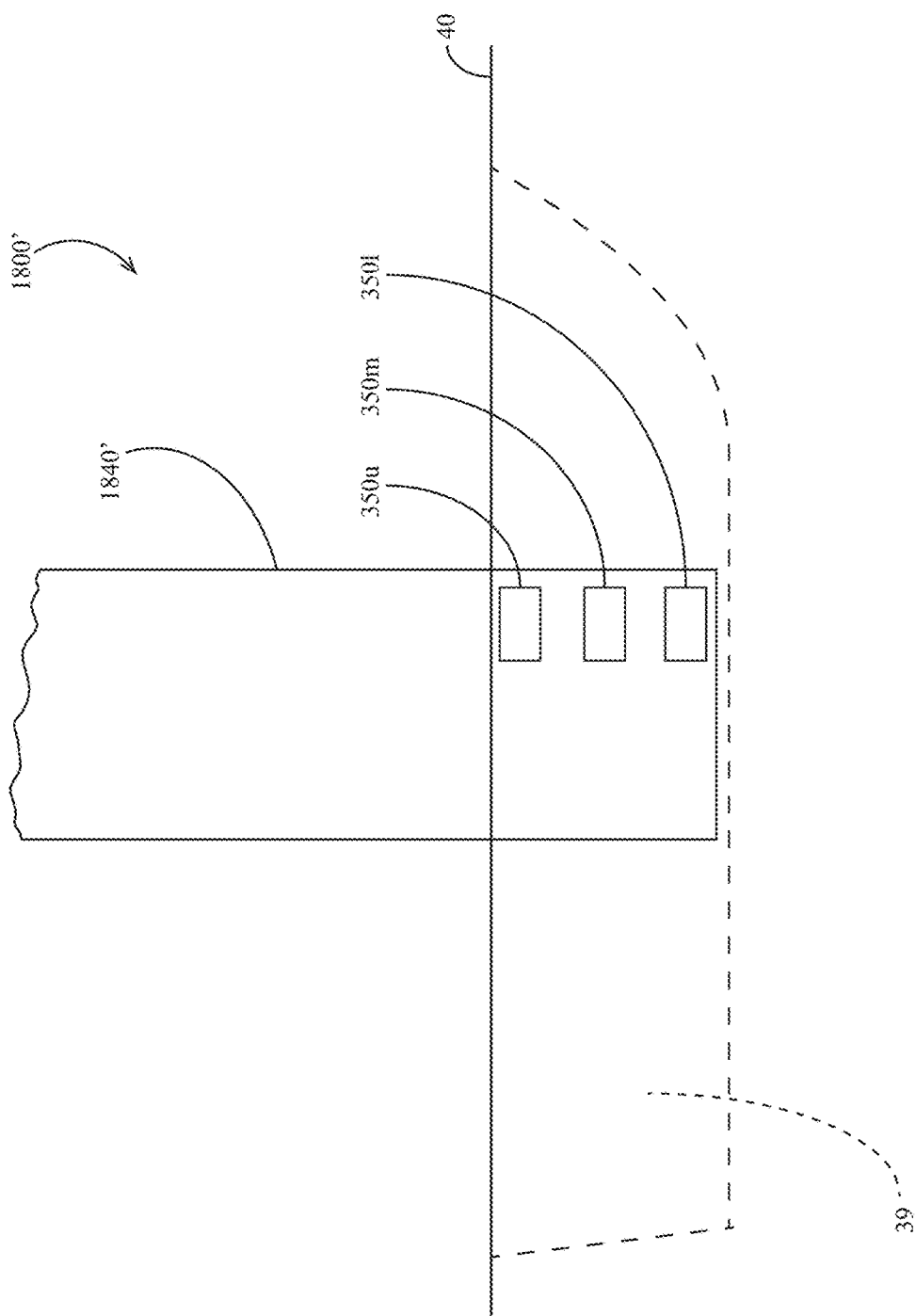
FIG. 23 is a side elevation view of another embodiment of a reference sensor having an instrumented shank.
Figure 24:
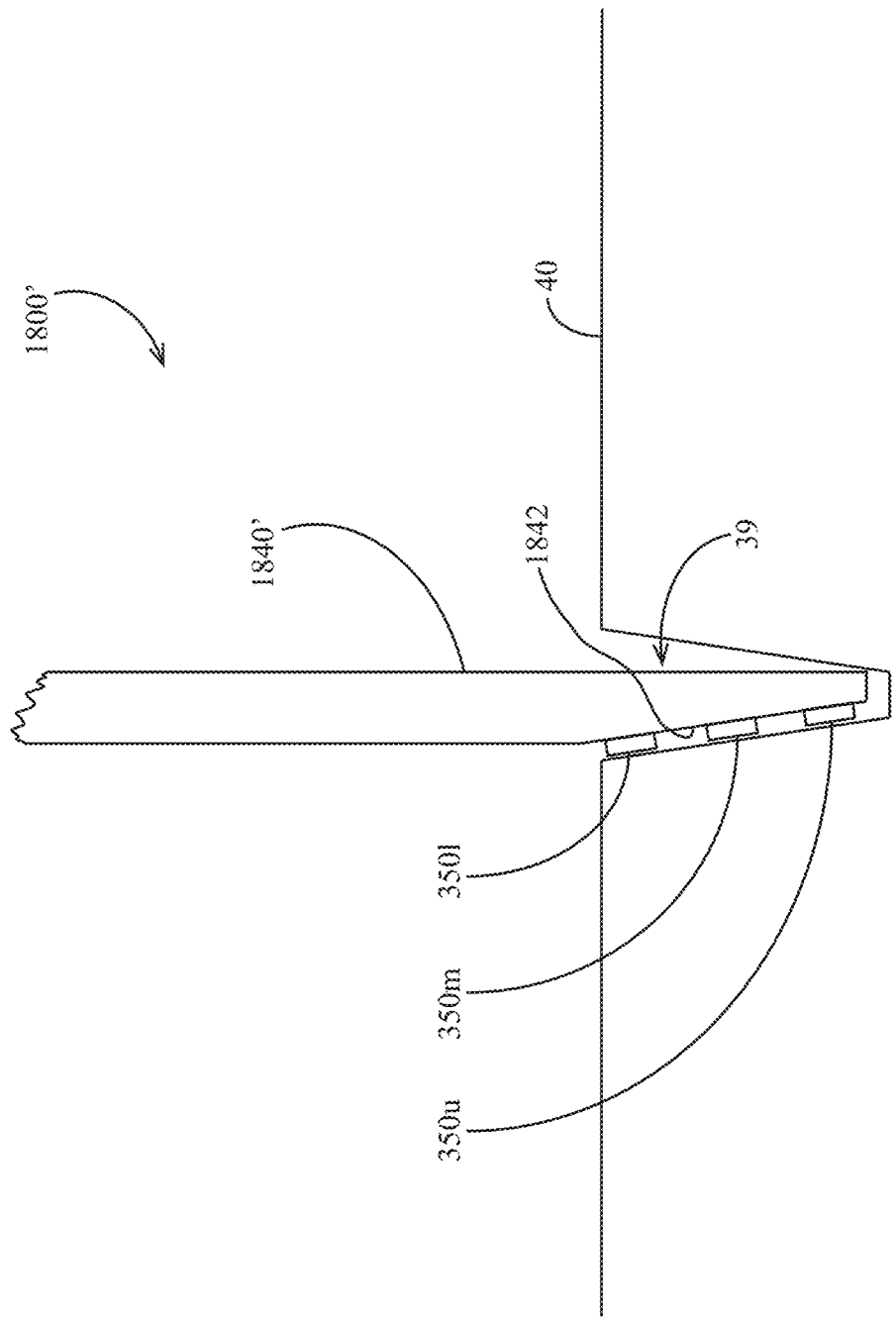
FIG. 24 is a front elevation view of the reference sensor of FIG. 23.

An embodiment of the reference sensor 1800' including an instrumented shank 1840' is illustrated in FIGS. 23 and 24. Reference sensors 350u, 350m, 350l, are preferably disposed on a lower end of the shank 1840 and disposed to contact soil on a sidewall of the trench 39 at or adjacent the top of the trench, at an intermediate trench depth, and at or adjacent the bottom of the trench, respectively. The shank 1840 extends into the trench and preferably includes an angled surface 1842 to which the reference sensors 350 are mounted; the angle of surface 1842 is preferably parallel to the sidewall of the trench 39.

It should be appreciated that the sensor embodiment of FIGS. 4A-4C may be mounted to and used in conjunction with implements other than seed planters such as tillage tools. For example, the seed firmer could be disposed to contact soil in a trench opened by (or soil surface otherwise passed over by) a tillage implement such as a disc harrow or soil ripper. On such equipment, the sensors could be mounted on a part of the equipment that contacts soil or on any extension that is connected to a part of the equipment and contacts soil. It should be appreciated that in some such embodiments, the seed firmer would not contact planted seed but would still measure and report soil characteristics as otherwise disclosed herein.

Figures 27A, 27B:
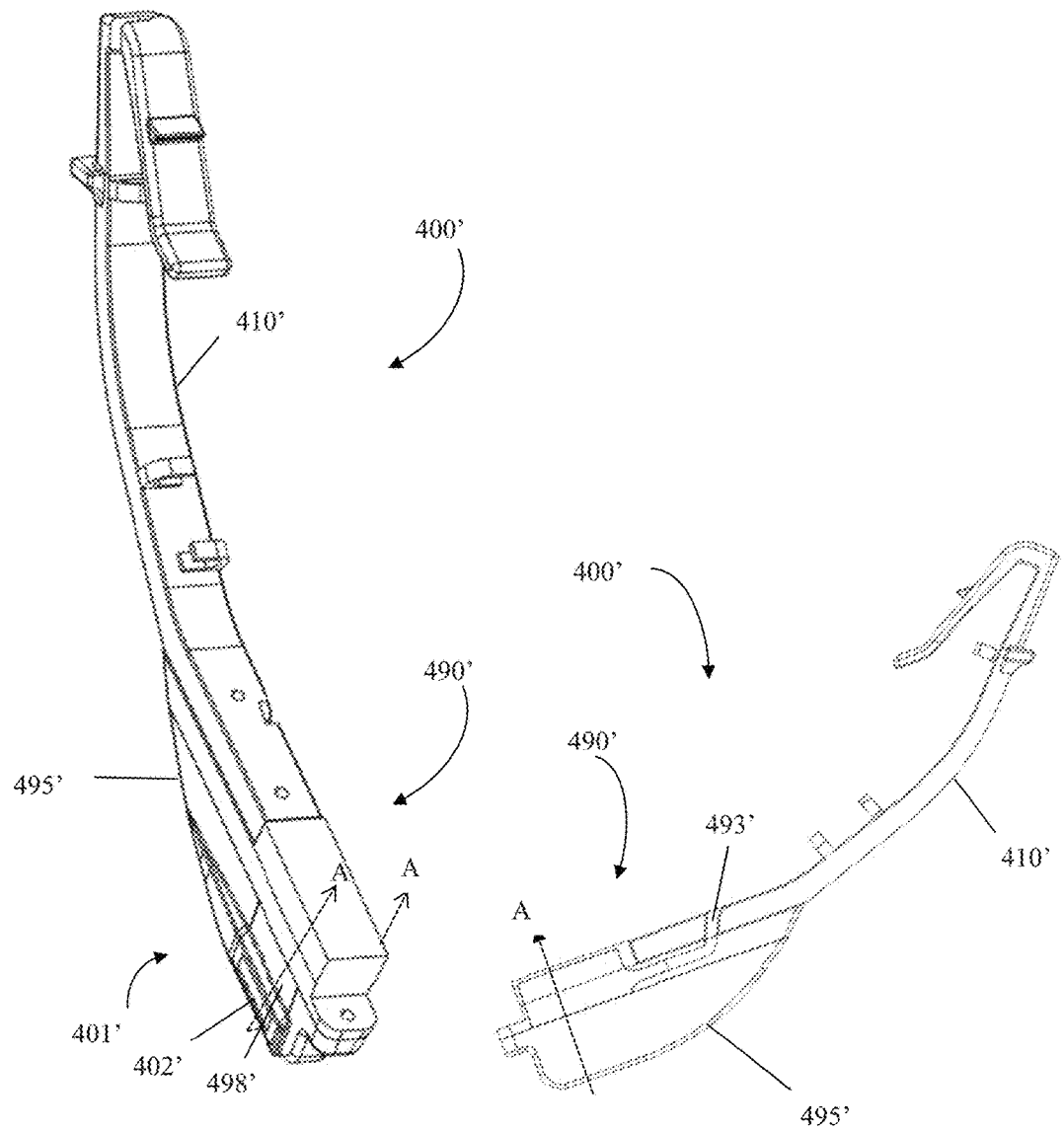
FIG. 27A is a perspective view of a seed firmer according to one embodiment.
FIG. 27B is a side view of the seed firmer of FIG. 27A.

In another embodiment, any of the sensors (reflectivity sensor 350, temperature sensor 360, electrical conductivity sensor 370, capacitive moisture sensor 351, and electronic tensiometer sensor 352) can be disposed in seed firmer 400' with an exposure through a side of seed firmer 400'. As illustrated in FIG. 27A in one embodiment, seed firmer 400' has a protrusion 401' from a side of seed firmer 400' through which the sensors sense. Disposed in protrusion 401' is a lens 402'. Having protrusion 401' minimizes any buildup that blocks lens 402', and lens 402' can stay in contact with the soil.

Figure 28A:
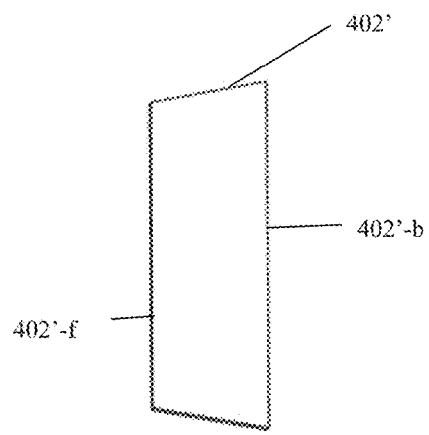
FIG. 28A is a side view of a lens according to one embodiment.
Figure 28B:
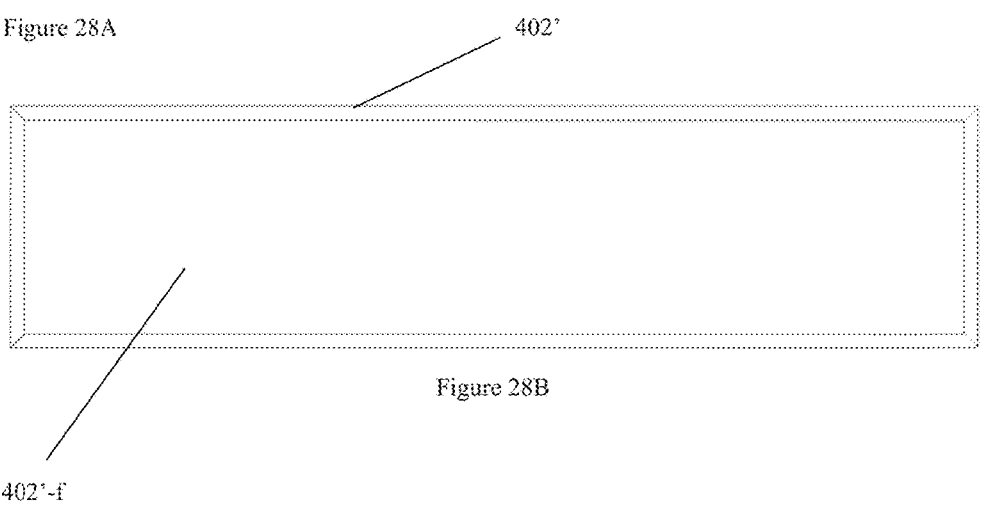
FIG. 28B is a front view of the lens of FIG. 28A.

Lens 402' can be made from any material that is durable to the abrasion caused by soil contact and transparent to the wavelengths of light used. In certain embodiment, the material has a Mohs hardness of at least 8. In certain embodiments, the material is sapphire, ruby, diamond, moissanite (SiC), or toughened glass (such as Gorilla™ glass). In one embodiment, the material is sapphire. In one embodiment as illustrated in FIGS. 28A and 28B, lens 402' is a trapezoidal shape with sides sloped from the back 402'-b to the front 402'-f of lens 402'. In this embodiment, lens 402' can sit within protrusion 401' with no retainers against the back 402'-b of lens 402'. Sensors that are disposed behind lens 402' are then not obstructed by any such retainers. Alternatively, lens 402' can be disposed the opposite to the previous embodiment with the sides sloped from the front 402-f to the back 402-b.

Figure 30A:
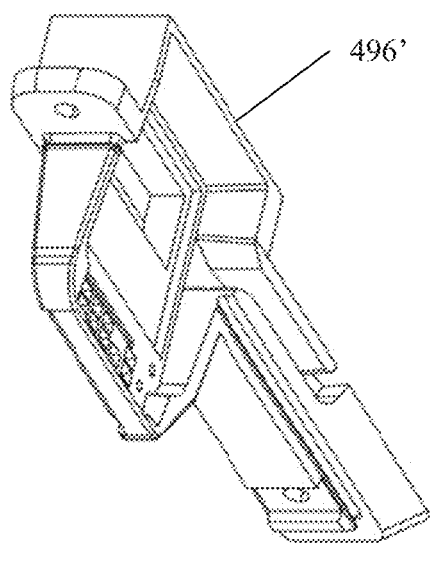
FIG. 30A is a perspective view of a sensor housing according to one embodiment.
Figure 30B:
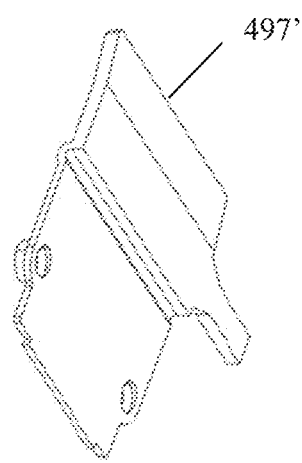
FIG. 30B is a perspective view of a cover according to one embodiment.
Figures 31A, 31B:
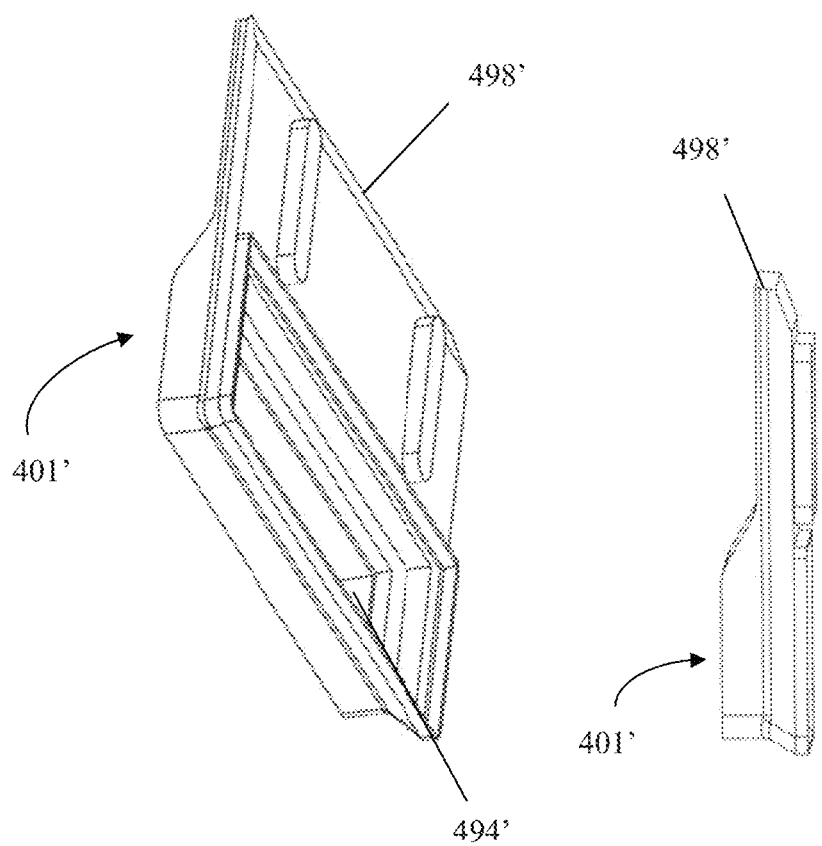
FIG. 31A is a perspective view of a lens body according to one embodiment.
FIG. 31B is a side view of the lens body of FIG. 31A.

For ease of assembly and for disposing sensors in seed firmer 400', seed firmer 400' can be fabricated from component parts. In this embodiment, seed firmer 400' has a resilient portion 410', which mounts to shank 254 and can urge seed firmer body portion 490' into resilient engagement with the trench 38. Firmer body portion 490' includes a firmer base 55495', sensor housing 496', and lens body 498'. Base 55495' is illustrated in FIGS. 29A to 29C. Sensor housing 496' is illustrated in FIG. 30A, and a cover 497' for mating with sensor housing 496' is illustrated in FIG. 30B. Lens body 498' is illustrated in FIGS. 31A and 31B, and lens body 498' is disposed in opening 499' in firmer base 55495'. Lens 402' is disposed in lens opening 494' in lens body 498'. Sensors are disposed (such as on a circuit board, such as 580 or 2596) in sensor housing 496'. As illustrated in FIG. 27B, there is a conduit 493 disposed through a side of resilient portion 410' and entering into sensor housing 496' for wiring (not shown) to connect to the sensors.

Protrusion 401' will primarily be on lens body 498', but a portion of protrusion 401' can also be disposed on firmer body 55495' to either or both sides of lens body 498' to create a taper out to and back from protrusion 401'. It is expected protrusion 401' will wear with contact with the soil. Disposing a major portion of protrusion 401' on lens body 498' allows for replacement of lens body 498' after protrusion 401' and/or lens 402' become worn or broken.

Figure 53:
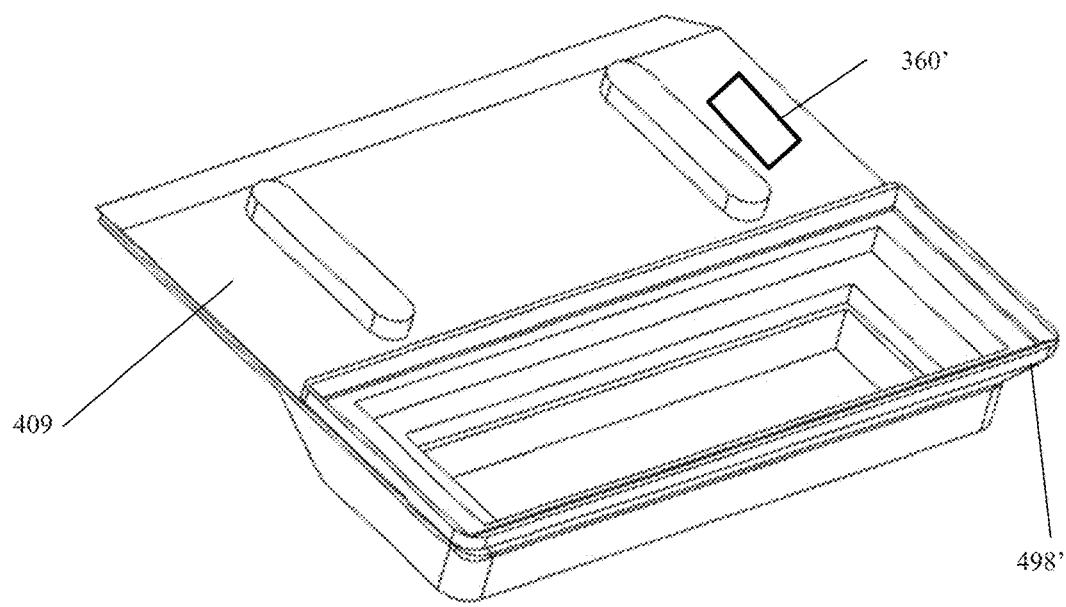
FIG. 53 is a perspective view of a temperature sensor disposed on an interior wall according to one embodiment.

In another embodiment illustrated in FIG. 53, a temperature sensor 360' is disposed in a seed firmer 400 (the reference to seed firmer 400 in this paragraph is to any seed firmer such as 400, 400', 400", or 400''') to measure temperature on an interior wall 409 that is in thermal conductivity with an exterior of seed firmer 400. Temperature sensor 360' measures the temperature of interior wall 409. In one embodiment, the area of interior wall 409 that temperature sensor 360' measures is no more than 50% of the area of interior wall 409. In other embodiments, the area is no more than 40%, no more than 30%, no more than 20%, no more than 10%, or no more than 5%. The smaller the area, the faster that temperature sensor 360' can react to changes in temperature. In one embodiment, temperature sensor 360' is a thermistor. Temperature sensor 360' can be in electrical communication with a circuit board (such as circuit board 580 or 2596).

Figure 54:
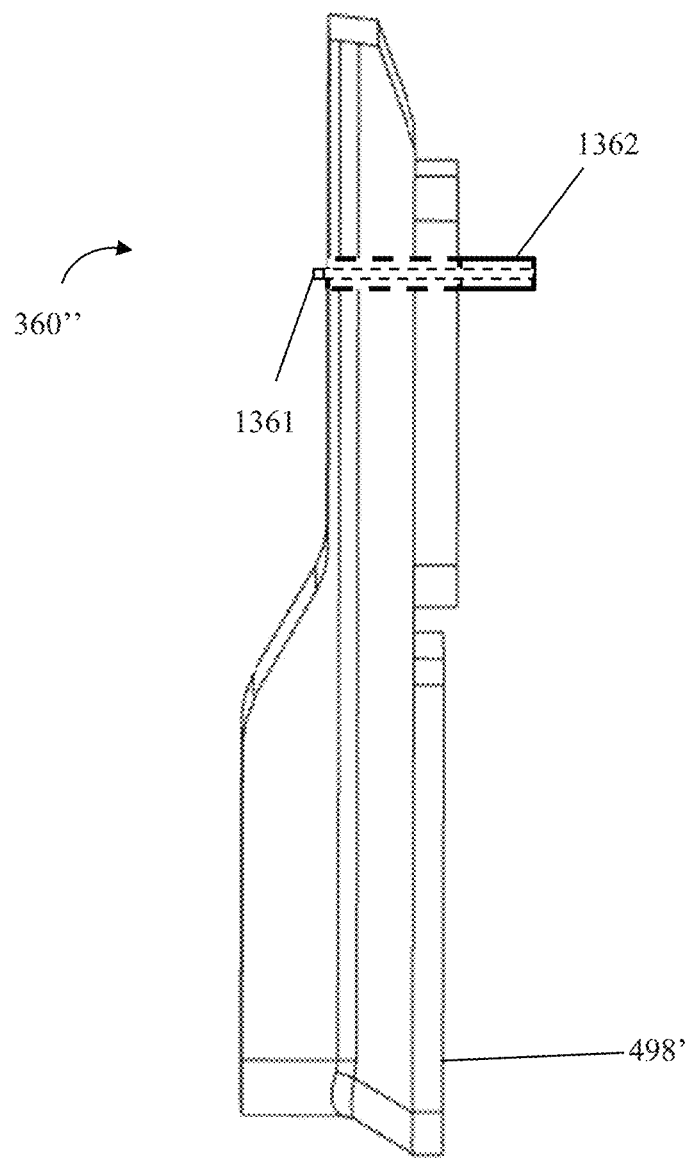
FIG. 54 is a side view of a temperature sensor disposed through a seed firmer to measure temperature of soil directly according to one embodiment.

In another embodiment illustrated in FIG. 54, a temperature sensor 360" is disposed through seed firmer 400 (the reference to seed firmer 400 in this paragraph is to any seed firmer such as 400, 400', 400", or 400''') to measure temperature of soil directly. Temperature sensor 360" has an internal thermally conductive material 1361 covered by a thermally insulating material 1362 with a portion of thermally conductive material 1361 exposed to contact soil. The thermally conductive material in one embodiment can be copper. Temperature sensor 360" can be in electrical communication with a circuit board (such as circuit board 580 or 2596).

In either of the embodiments in FIGS. 53 and 54, temperature sensor 360', 360" is modular. It can be a separate part that can be in communication with monitor 50 and separately replaceable from other parts.

Figure 32:
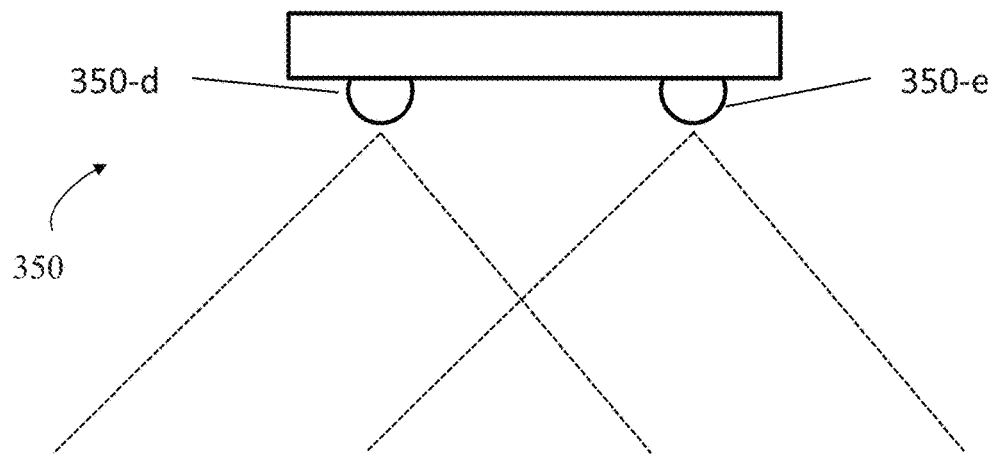
FIG. 32 is a side view of a sensor with an emitter and a detector according to one embodiment.

In one embodiment with seed firmer 400', the sensor is the reflectivity sensor 350. Reflectivity sensor 350 can be two components with an emitter 350-*e* and a detector 350-*d*. This embodiment is illustrated in FIG. 32.

In certain embodiments, the wavelength used in reflectivity sensor 350 is in a range of 400 to 1600 nm. In another embodiment, the wavelength is 550 to 1450 nm. In one embodiment, there is a combination of wavelengths. In one embodiment, sensor 350 has a combination of 574 nm, 850 nm, 940 nm, and 1450 nm. In another embodiment, sensor 350 has a combination of 589 nm, 850 nm, 940 nm, and 1450 nm. In another embodiment, sensor 350 has a combination of 640 nm, 850 nm, 940 nm, and 1450 nm. In another embodiment, the 850 nm wavelength in any of the previous embodiments is replaced with 1200 nm. In another embodiment, the 574 nm wavelength of any of the previous embodiments is replaced with 590 nm. For each of the wavelengths described herein, it is to be understood that the number is actually +/−10 nm of the listed value.

In one embodiment, the field of view from the front 402-*f* of lens 402' to the soil surface is 0 to 7.5 mm (0 to 0.3 inches). In another embodiment, the field of view is 0 to 6.25 mm (0 to 0.25 inches). In another embodiment, the field of view is 0 to 5 mm (0 to 0.2 inches). In another embodiment, the field of is 0 to 2.5 mm (0 to 0.1 inches).

As seed firmer 400' travels across trench 38, there may be instances where there is a gap between trench 38 and seed firmer 400' such that ambient light will be detected by reflectivity sensor 350. This will give a falsely high result. In one embodiment to remove the signal increase from ambient light, emitter 350-*e* can be pulsed on and off. The background signal is measured when there is no signal from emitter 350-*e*. The measured reflectivity is then determined by subtracting the background signal from the raw signal when emitter 350-*e* is emitting to provide the actual amount of reflectivity.

Figure 33:
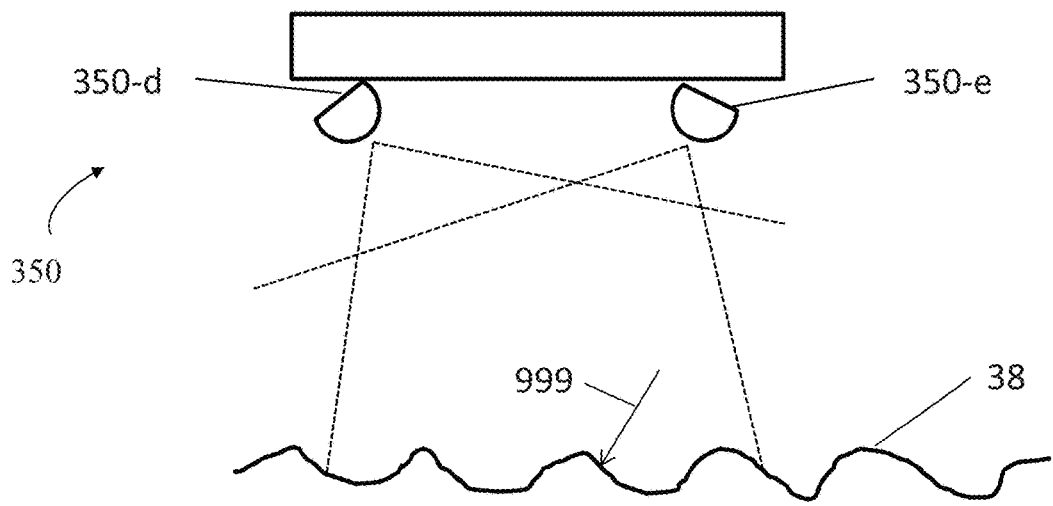
FIG. 33 is a side view of a sensor with an emitter and a detector that are angled towards each other according to one embodiment.

As shown in FIG. 32, when reflectivity sensor 350 has just one emitter 350 *e* and one detector 350-*d*, the area of overlap between the area illuminated by emitter 350-*e* and the area viewed by detector 350-*d* can be limited. In one embodiment as illustrated in FIG. 33, emitter 350-*e* and detector 350-*d* can be angled towards each other to increase the overlap. While this is effective, this embodiment does increase the manufacturing cost to angle the emitter 350-*e* and detector 350-*d*. Also, when the surface of trench 38 is not smooth, there can be some ray of light 999 that will impact trench 38 and not be reflected towards detector 350-*d*.

Figure 34:
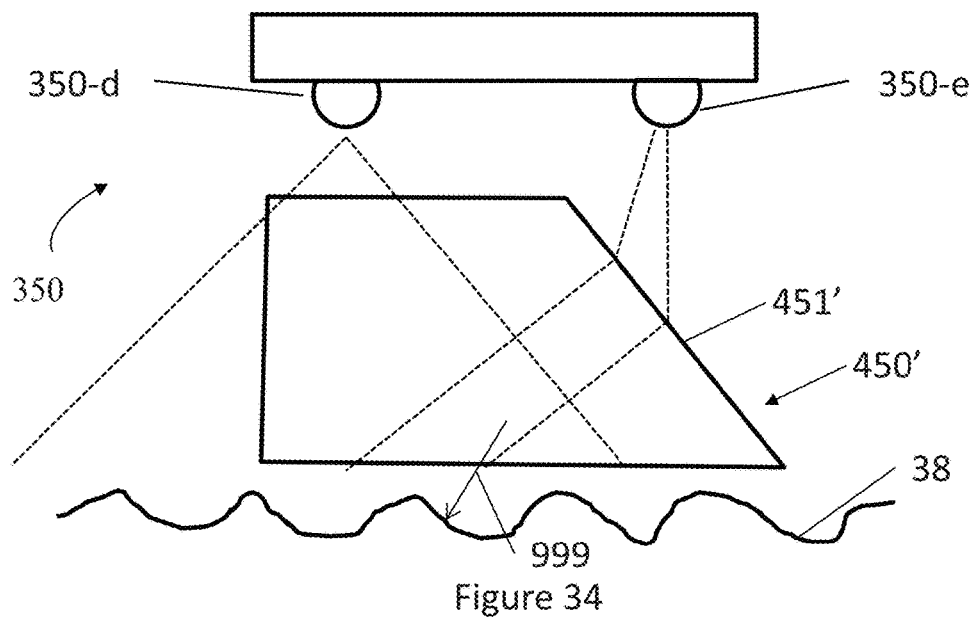
FIG. 34 is a side view of a sensor and prism combination according to one embodiment.

In another embodiment illustrated in FIG. 34, the configuration from FIG. 32 can be used, and a prism 450' with a sloped side 451' disposed under emitter 350-*e* can refract the light from emitter 350-*e* towards the area viewed by detector 350-*d*. Again, with a single emitter 350-*e*, ray of light 999 may impact trench 38 and not be reflected towards detector 350-*d*.

Figure 35:
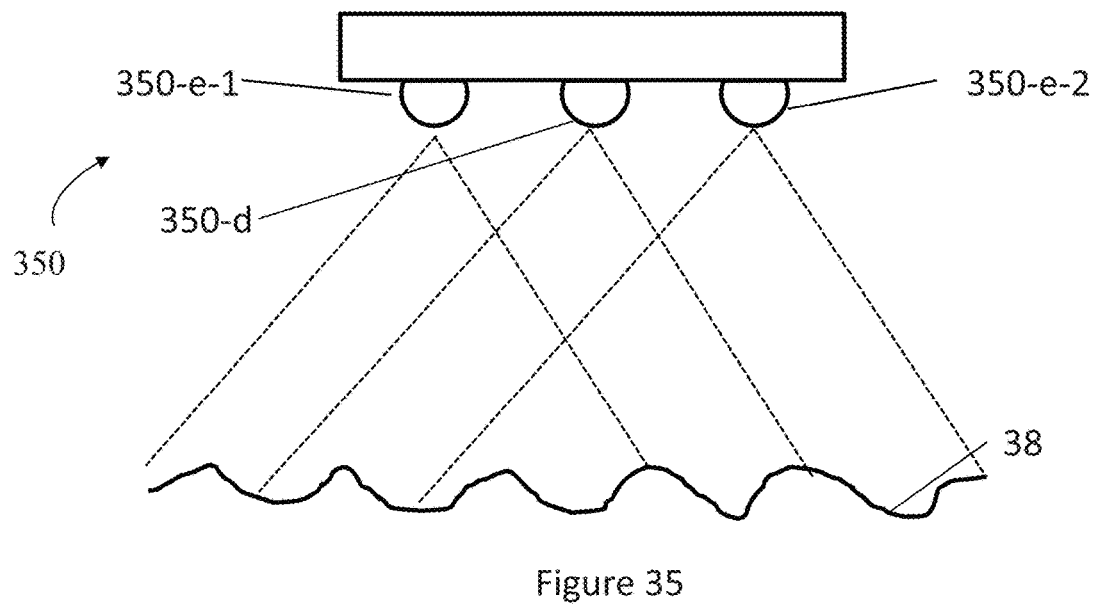
FIG. 35 is a side view of a sensor with two emitters and a detector according to one embodiment.
Figure 36:
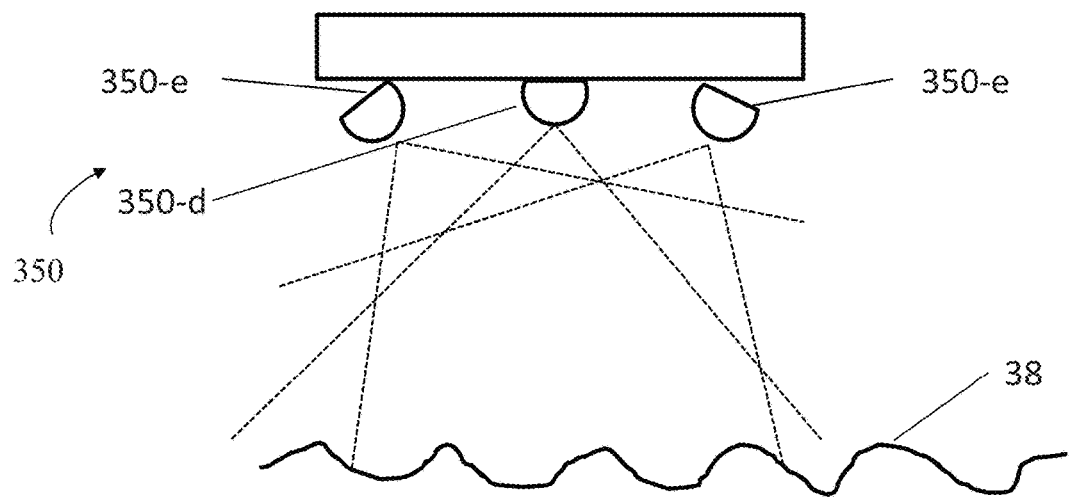
FIG. 36 is a side view of a sensor with two emitters angled toward a detector according to one embodiment.

In another embodiment illustrated in FIG. 35, sensor 350 can have two emitters 350-*e*-1 and 350-*e*-2 and one detector 350-*d*. This increases the overlap between the area viewed by detector 350-*d* and the area illuminated by emitters 350-*e*-1 and 350-*e*-2. In another embodiment, to further increase the overlap, emitters 350-*e*-1 and 350-*e*-2 can be angled towards detector 350-*d* as illustrated in FIG. 36.

Figure 37:
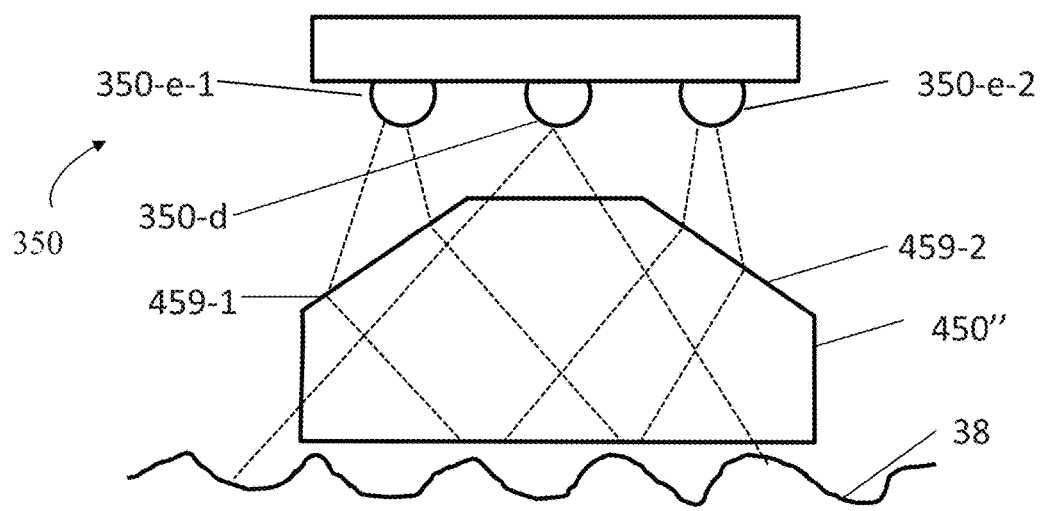
FIG. 37 is a side view of a sensor with two emitters and a detector and a prism according to one embodiment.

In another embodiment illustrated in FIG. 37, two emitters 350-*e*-1 and 350-*e*-2 are disposed next to detector 350-*d*. A prism 450" has two sloped surfaces 459-1 and 459-2 for refracting light from emitters 350-*e*-1 and 350-*e*-2 towards the area viewed by detector 350-*d*.

Figure 38:
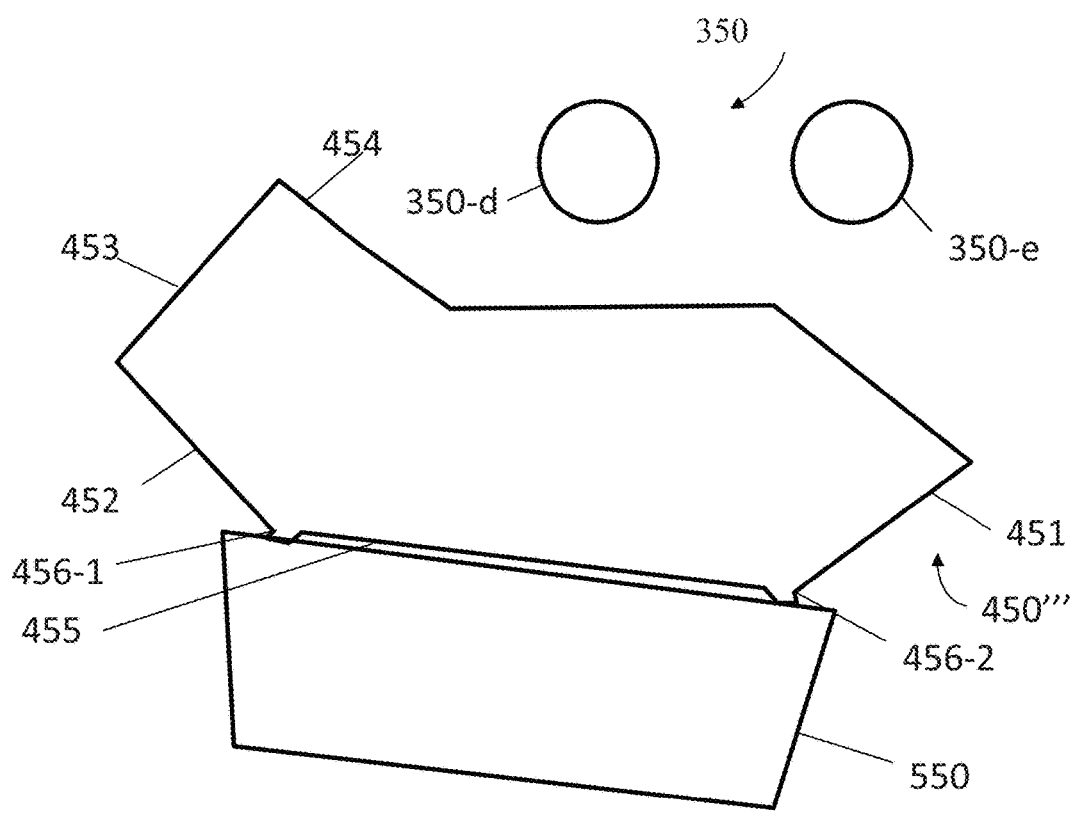
FIG. 38 is a side view of a sensor with an emitter and a detector along with a prism that uses the critical angle of the material of the prism according to one embodiment.

In another embodiment illustrated in FIG. 38, a single emitter 350-*e* can be used in conjunction with a prism 400" to approximate a dual emitter. Prism 450''' is designed with angled sides to utilize the critical angle of the material used to make prism 450" (to keep light within the material). The angles vary depending on the material. In one embodiment, the material for prism 450' is polycarbonate. A portion of the light from emitter 350-*e* will impact side 451 and be reflected to side 452 to side 453 to side 454 before exiting bottom 455. Optionally, spacers 456-1 and 456-2 can be disposed on the bottom 455 to provide a gap between prism 450''' and lens 550.

Figure 39:
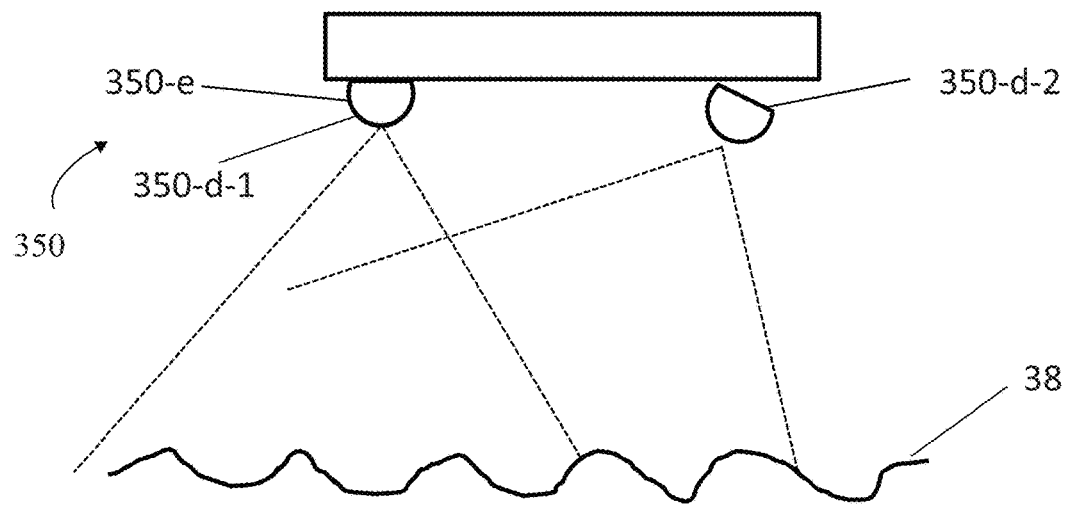
FIG. 39 is a side view of a sensor with one emitter and two detectors according to one embodiment.

In another embodiment, illustrated in FIG. 39, reflectivity sensor has one emitter 350-*e* and two detectors 350-*d*-1 and 350-*d*-2. As shown, emitter 350-*e* and detector 350-*d*-1 are aligned as viewed into the figure. Detector 350-*d*-2 is angled towards emitter 350-1 and detector 350-*d*-2.

Figure 40:
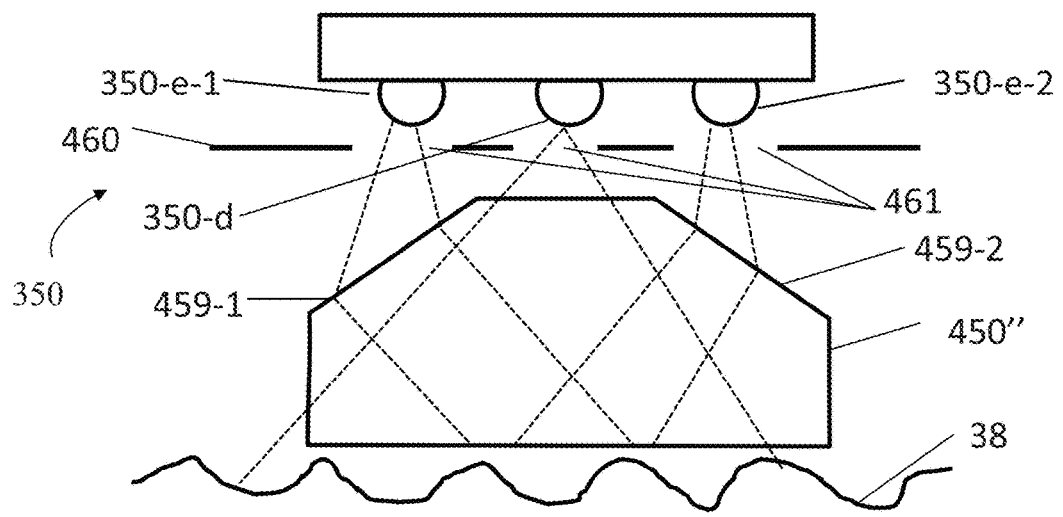
FIG. 40 is a side sectional view of an orifice plate used with the embodiment of FIG. 37.

In another embodiment that can be used with any of the previous embodiments or following embodiments, an aperture plate 460 can be disposed adjacent to the sensor 350 with apertures 461 adjacent to each emitter 350-*e* and detector 350-*d*. This embodiment is illustrated in FIG. 40 with the embodiment from FIG. 37. The aperture plate 460 can assist in controlling the half angles.

Figure 41:
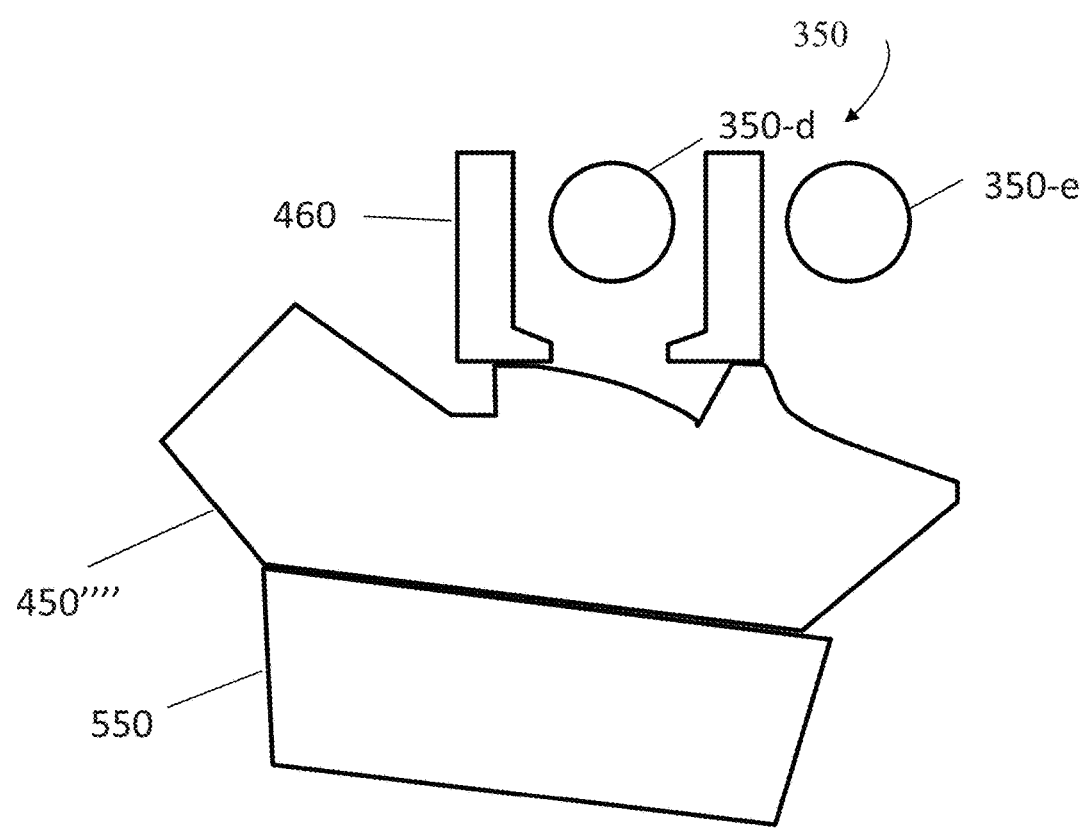
FIG. 41 is a side sectional view of a sensor with one emitter and one detector along with a prism that uses the critical angle of the material of the prism according to one embodiment.
Figure 42A:
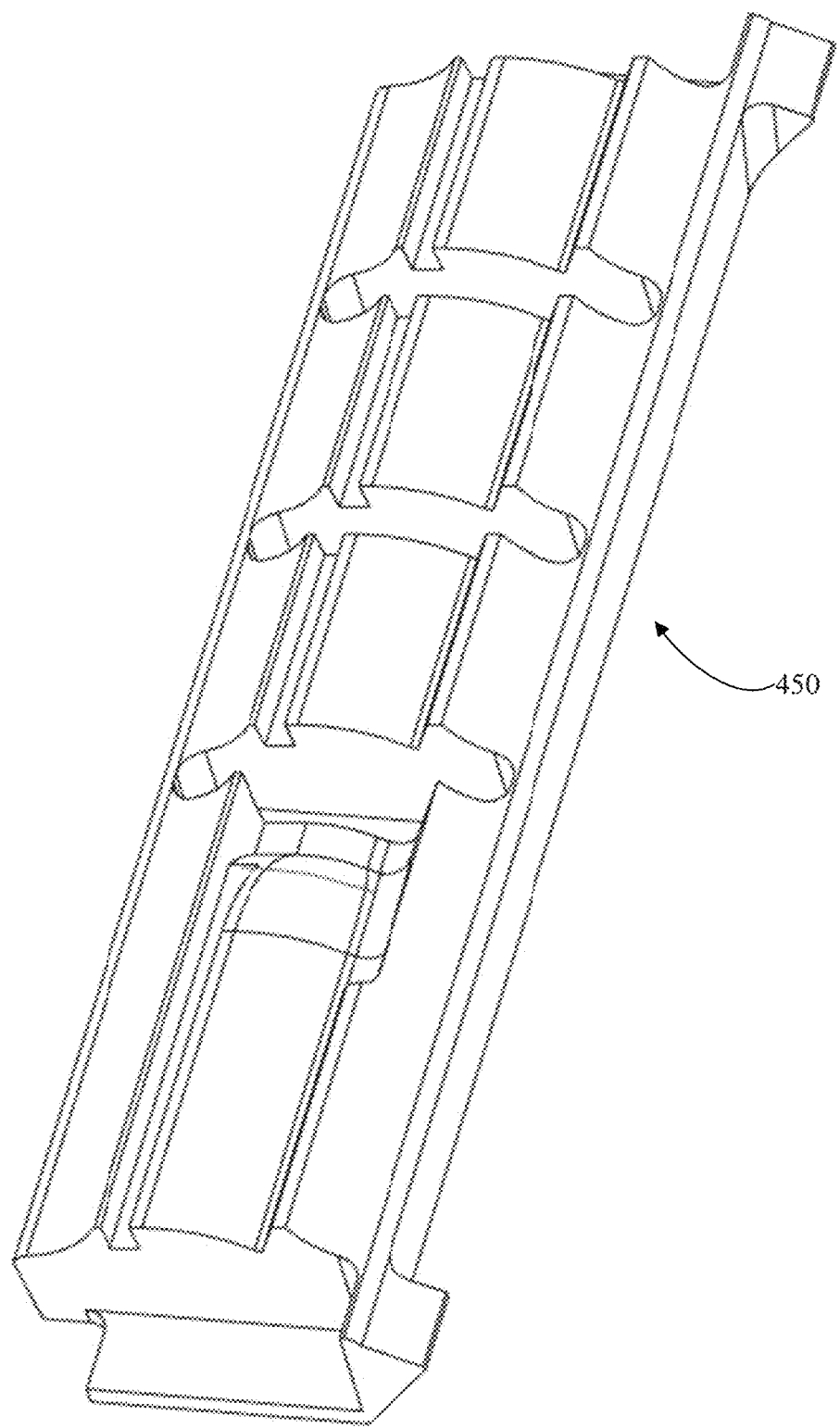
FIG. 42A is an isometric view of a prism according to one embodiment.
Figures 42B, 42C:
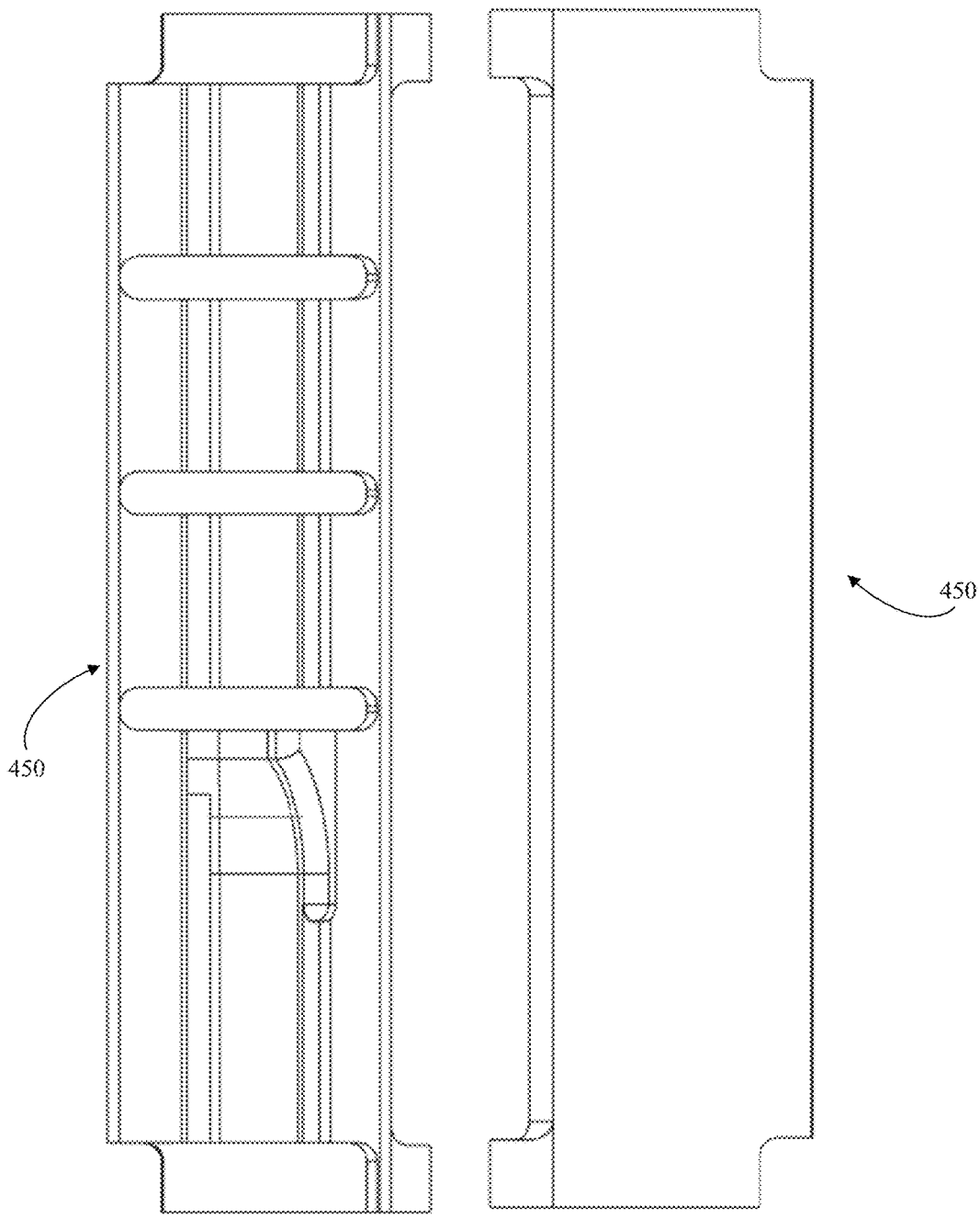
FIG. 42B is a top plan view of the prism of FIG. 42A.
FIG. 42C is a bottom elevation view of the prism of FIG. 42A.
Figure 42D:
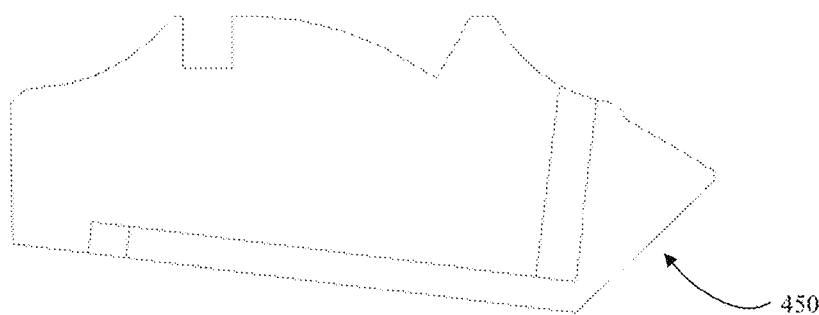
FIG. 42D is a front elevation view of the prism of FIG. 42A.
Figure 42E:
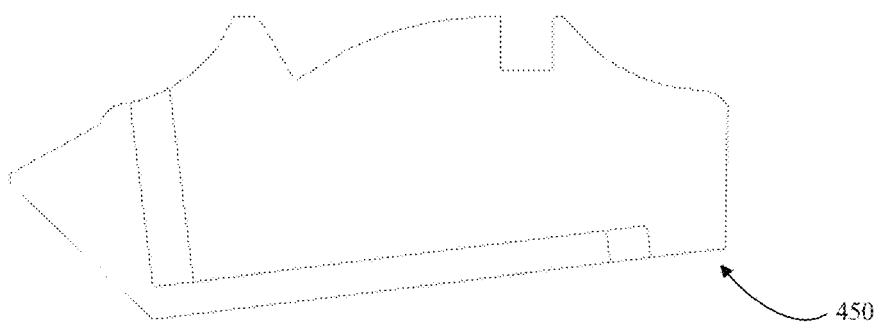
FIG. 42E is a rear elevation view of the prism of FIG. 42A.
Figure 42F:
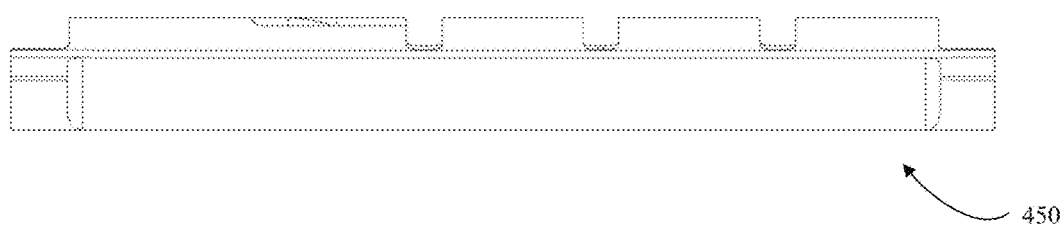
FIG. 42F is a right elevation view of the prism of FIG. 42A.
Figure 42G:
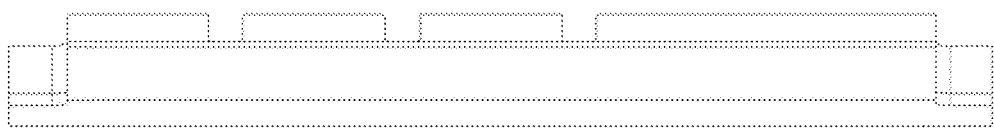
FIG. 42G is a left elevation view of the prism of FIG. 42A.

In another embodiment illustrated in FIG. 41, a reflectivity sensor 350 has one emitter 350-*e* and one detector 350-*d*. Disposed adjacent to the detector is an orifice plate 460 that is only controlling the light entering detector 350-*d*. Prism 450"" is then disposed adjacent to the emitter 350-*e* and detector 350-*d*.

In another embodiment of a prism, multiple views of prism 450 can be seen in FIGS. 42A-42G.

Figure 43:
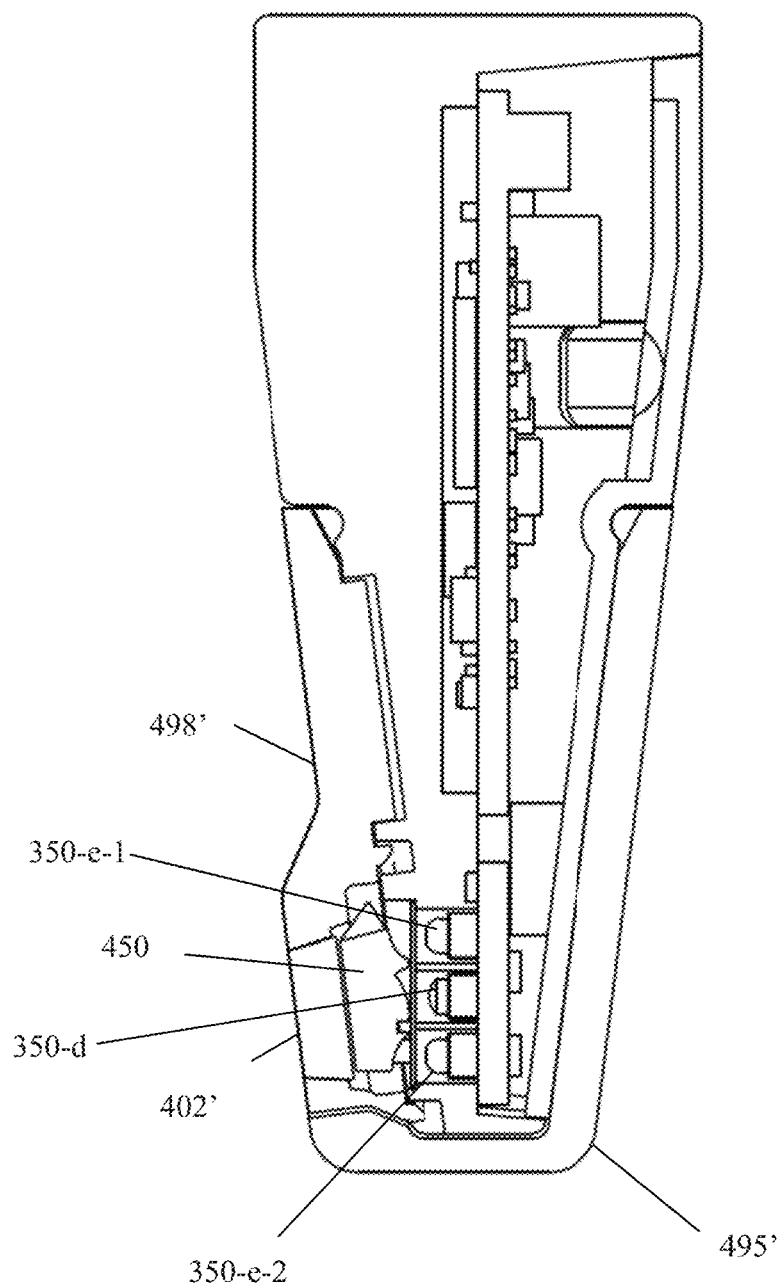
FIG. 43 is a sectional view of seed firmer of FIG. 27A at section A-A.

FIG. 43 is a cross-sectional view of seed firmer 400' of FIG. 27A taken at section A-A. Two emitters 350-*e*-1 and 350-*e*-2 and one detector 350-*d* are disposed in sensor housing 496'. Prism 450 from FIGS. 42A-42G is disposed between emitters 350-*e*-1 and 350-*e*-2 and detector 350-*d* and lens 402'.

Figure 44A:
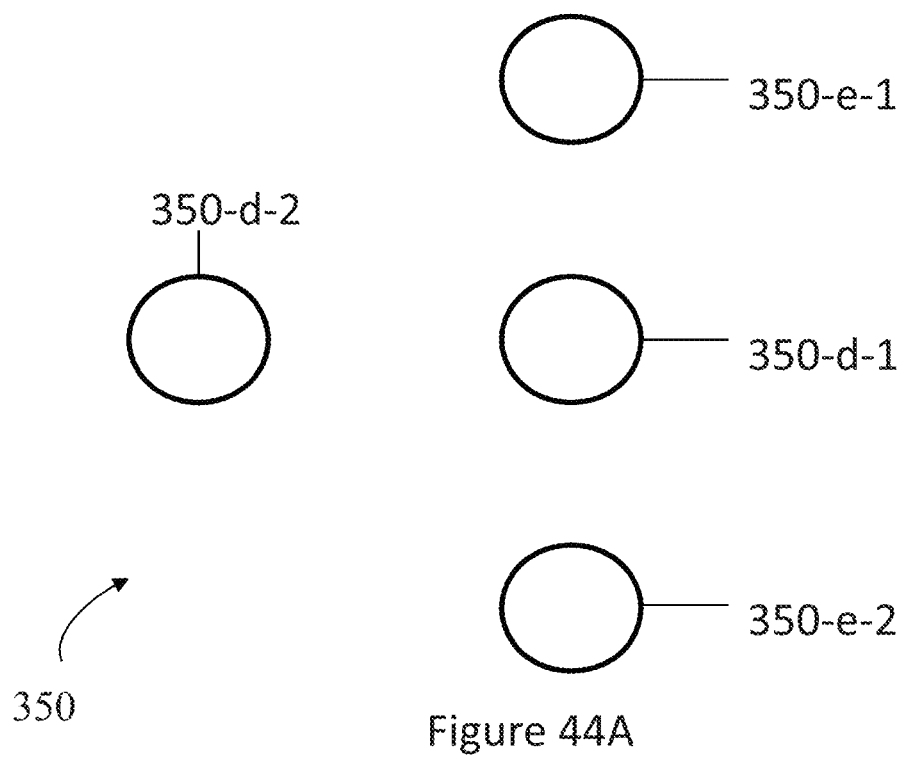
FIG. 44A is a front schematic view of a sensor with two emitters and one detector in line and an offset detector according to one embodiment.
Figure 44B:
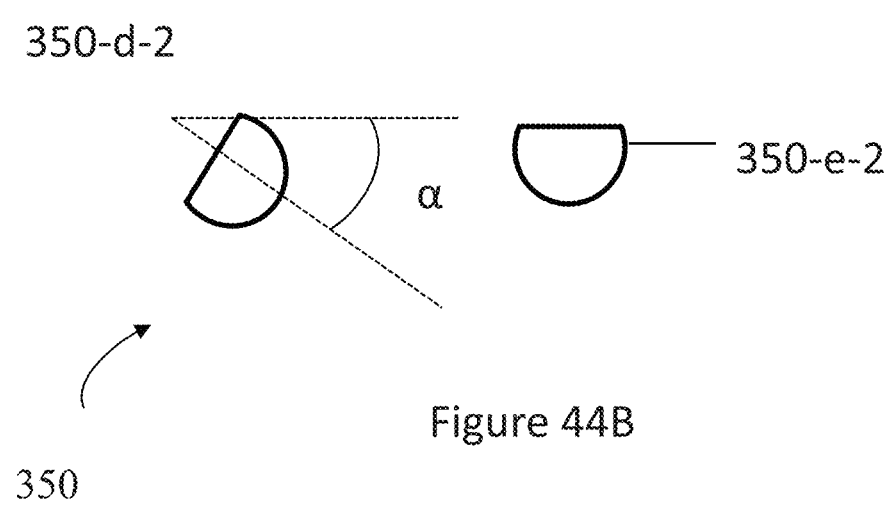
FIG. 44B is a side schematic view of the sensor of FIG. 44A.

In another embodiment as illustrated in FIGS. 44A and 44B, there is a reflectivity sensor 350 that has two emitters 350-*e*-1 and 350-*e*-2 in line with a detector 350-*d*-1. As viewed the emitters 350-*e*-1 and 350-*e*-2 are pointed out of the paper, and the view of detector 350-*d*-1 is pointed out of the paper. There is a second detector that is offset from emitters 350-*e*-1 and 350-*e*-2 and detector 350-*d*-1. In another embodiment (not shown) emitter 350-*e*-2 is omitted. As seen in FIG. 44B, detector 350-*d*-2 is angled from vertical by an angle $\alpha$ and is viewing towards emitters 350-*e*-1 and 350-*e*-2 and detector 350-*d*-1, which are aligned into the paper. In one embodiment, the angle $\alpha$ is 30 to 60°. In another embodiment, the angle $\alpha$ is 45°. In one embodiment, the wavelength of light used in this arrangement is 940 nm. This arrangement allows for measurement of void spaces in soil. Detecting void spaces in soil will inform how effective tillage has been. The less or smaller void spaces indicates more compaction and less effective tillage. More or larger void spaces indicates better tillage. Having this measurement of tillage effectiveness allows for adjustment of downforce on row unit 200 as described herein.

Figure 47:
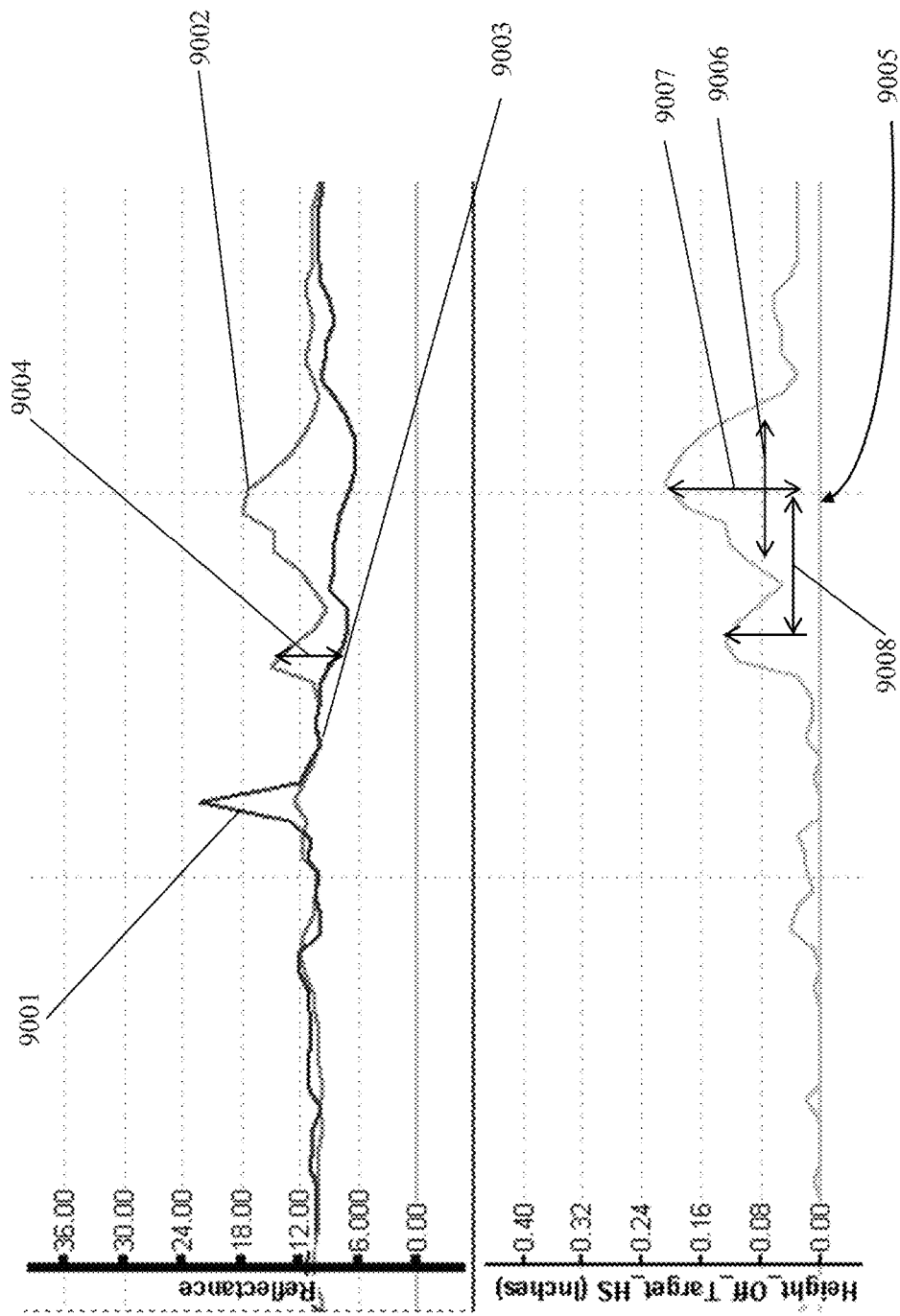
FIG. 47 illustrates a representative reflectance measurement and height off target.
Figure 48:
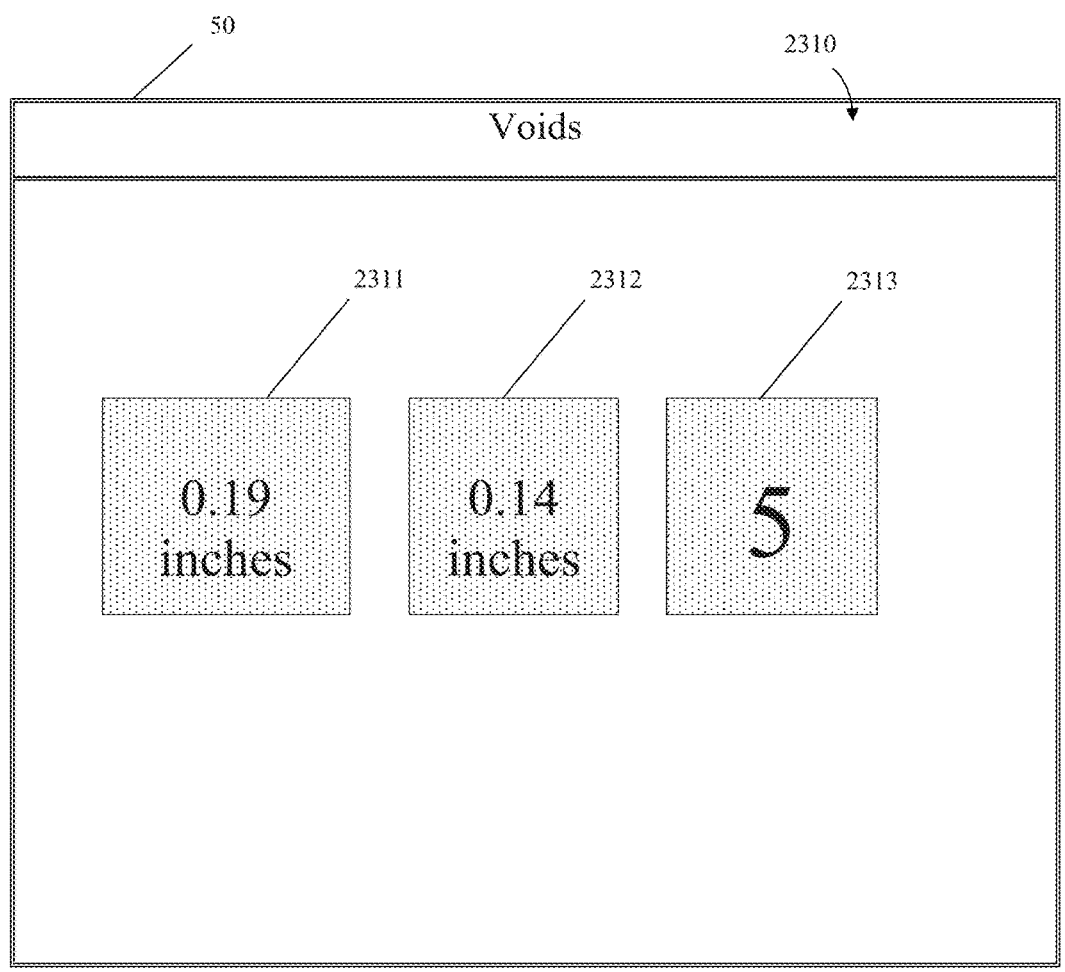
FIG. 48 illustrates an embodiment of a void screen.

The depth away from seed firmer 400, 400' and the length of void spaces can be measured by this arrangement. For short distances (generally up to 2.5 cm (1 inch) or up to about 1.27 cm (0.5 inches), the signal output from detector 350-*d*-2 increases as the distance to the target surface increases. While the signal from the primary reflectance detector, 350-*d*-1, stays mostly constant to slightly decreasing. An illustrative reflectance measurement is shown in FIG. 47 along with a corresponding calculated height off of target. The reflectance measurement from 350-*d*-1 9001 and the reflectance measurement from 350-*d*-2 9002 are shown. When reflectance measurement from 350-*d*-1 9001 and the reflectance measurement from 350-*d*-2 9002 are approximately the same, region 9003 is when target soil is flush with lens 402'. As a void is detected at region 9004, reflectance measurement from 350 *d* 1 9001 remains about the same or decreases, and the reflectance measurement from 350-*d*-2 9002 increases. The distance from the target surface is a function of the ratio between signals produced by 350-*d*-1 and 350-*d*-2. In one embodiment, the distance is calculated as (350-*d*-2 signal−350-*d*-1 signal)/(350-*d*-2 signal+350-*d*-1 signal)*scaling constant. The scaling constant is a number that converts the reflectance measurement into distance. For the illustrated configuration, the scaling factor is 0.44. The scaling factor is measured and depends on emitter and detector placement, aperture plate dimensions, and prism geometry. In one embodiment, a scaling factor can be determined by placing a target at a known distance. A plot of the calculated target distance produces an elevation profile 9005 along the scanned surface. Knowing travel speed, the length 9006, depth 9007, and spacing 9008 of these voids can be calculated. A running average of these void characteristics (length 9006, depth 9007, and spacing 9008) can be calculated and then reported as another metric to characterize the texture of the soil being scanned. For example, once every second, a summary of average void length, average void depth, and number of voids during that period could be recorded/transmitted to monitor 50. The timing interval can be any selected amount of time greater than 0. Having a shorter amount of time, a smaller space is analyzed. An example of monitor 50 displaying on screen 2310 void length 2311, void depth 2312, and number of voids 2313 is illustrated in FIG. 48.

In another embodiment, any scratches or films that form on lens 402' will affect the reflectivity detected by reflectivity sensor 350. There will be an increase in internal reflectivity within seed firmer 400, 400'. The increase in reflectivity will increase the reflectance measurement. This increase can be accounted for when seed firmer 400, 400' is removed from trench 38. The reading of seed firmer 400, 400' at this time will become the new base reading, e.g. zeroed out. The next time seed firmer 400, 400' is run in trench 38, the reflectivity above the new base or zero reading will be the actually measured reading.

Figure 45:
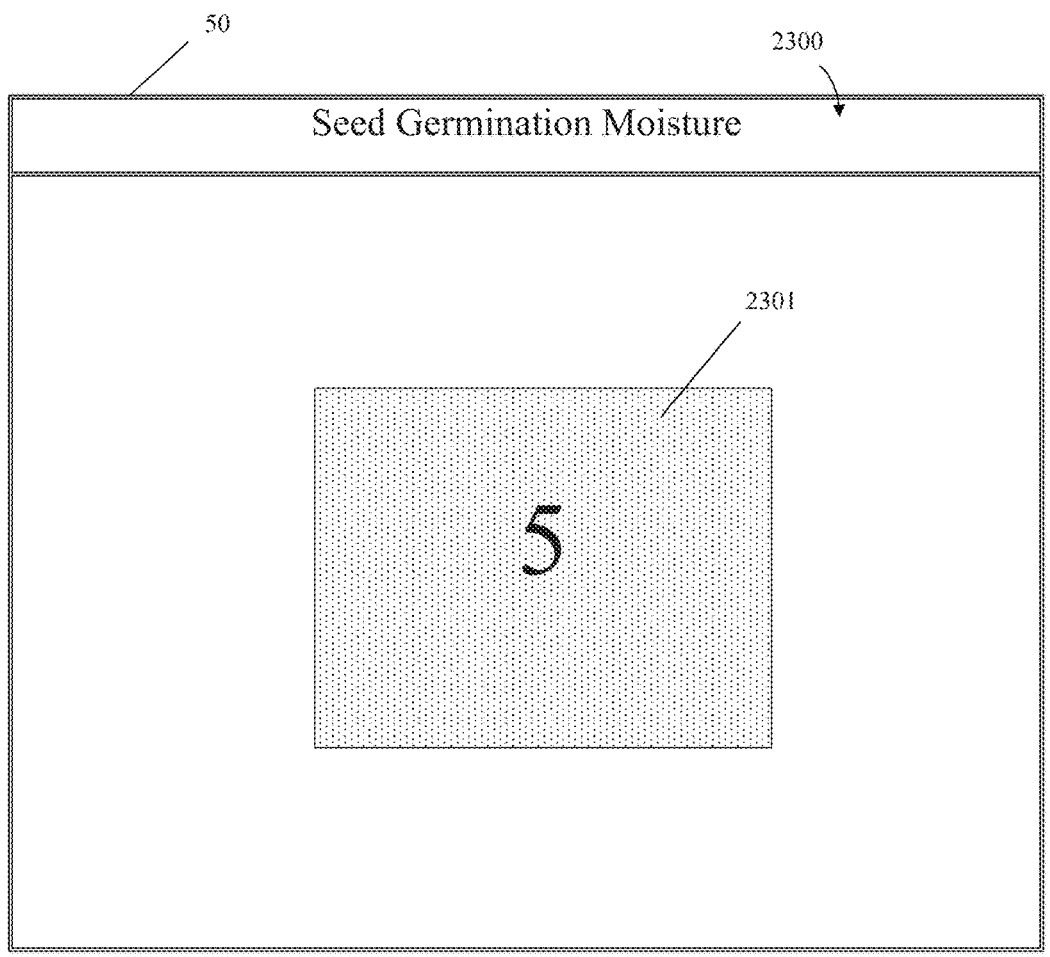
FIG. 45 illustrates an embodiment of a seed germination moisture screen.

In another embodiment, the reflectivity measurement from reflectivity sensor 350 allows for a seed germination moisture value to be obtained from a data table and displayed to an operator on monitor 50. Seed germination moisture is a dimensionless measurement related to the amount of water that is available to a seed for each given soil type. For different types of soil, water is retained differently. For example, sandy soil does not hold onto water as much as clay soil does. Even though there can be more water in clay than sand, there can be the same amount of water that is released from the soil to the seed. Seed germination moisture is a measurement of weight gain of a seed that has been placed in soil. Seed is placed in soil for a sufficient period of time to allow moisture to enter the seed. In one embodiment, three days is the period. The weight of the seed before and after is measured. Also, the reflectivity of soils at different water contents is stored in a data table. A scale of 1 to 10 can be used. Numbers in the middle of the scale, such as 4-7, can be associated with water contents in each soil type that is an acceptable level of water for seeds. Low numbers, such as 1-3, can be used to indicate that soil is too dry for the seed. High numbers, such as 8-10, can be used to indicate that soil is too wet for the seed. Knowing the soil type as input by the operator and the measured reflectivity, seed germination moisture can be obtained from the data table. The result can be displayed on monitor 50 with the actual number. Also, the result can be accompanied by a color. For example, the font color of the reported result or the screen color on monitor 50 can use green for values within the acceptable level and another color, such as yellow or red, for values that are high or low. An example of monitor 50 displaying on screen 2300 seed germination moisture 2301 is illustrated in FIG. 45. Alternatively, seed generation moisture 2301 can be displayed on monitor 50 in FIG. 20. Also, a uniform moisture can be displayed on monitor 50 (not shown). Uniform moisture is the standard deviation of seed germination moisture.

Depending on the seed germination moisture reading, the depth of planting can be adjusted as described herein. If the seed germination moisture is indicating too dry of conditions, then the depth can be increased to go deeper until a specified moisture level is achieved. If the seed germination moisture is indicating too moist, then the depth can be decreased to go shallower until a specified moisture level is achieved.

Figure 50:
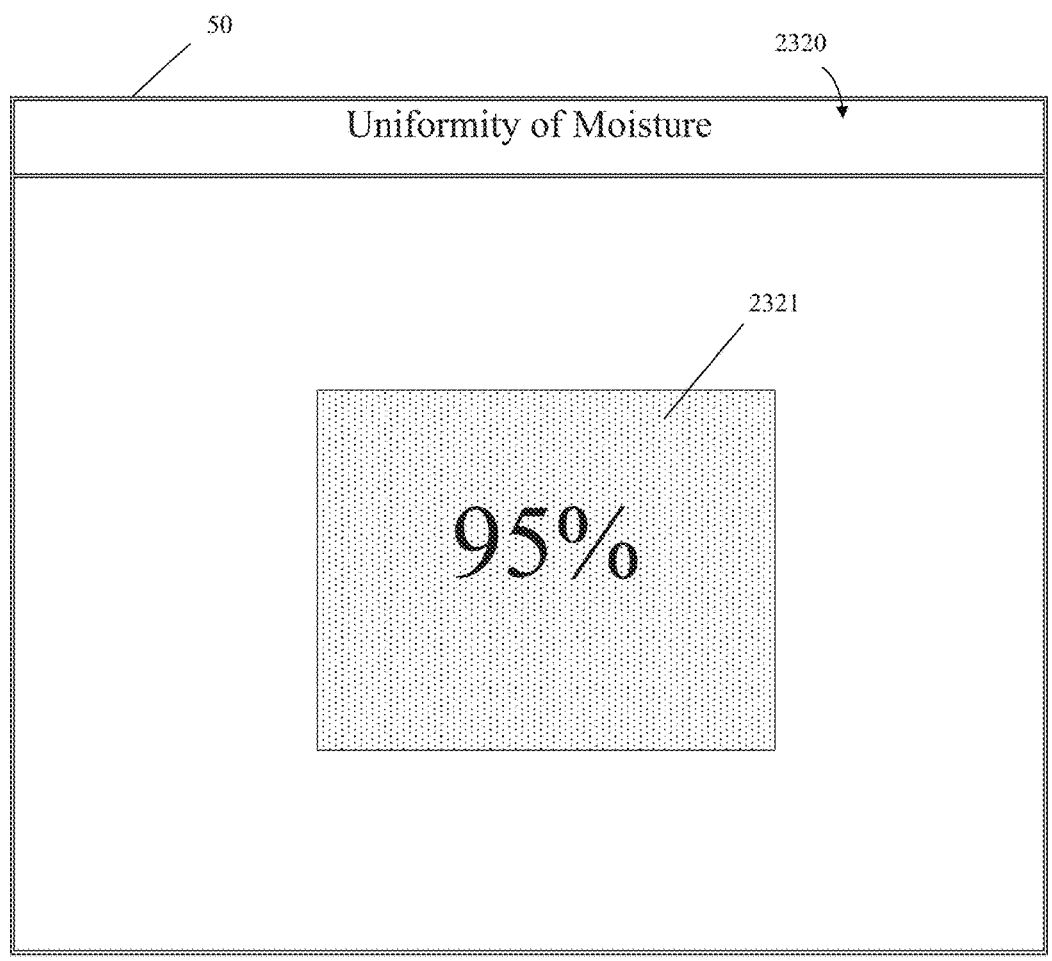
FIG. 50 illustrates an embodiment of a uniformity of moisture screen.
Figure 51:
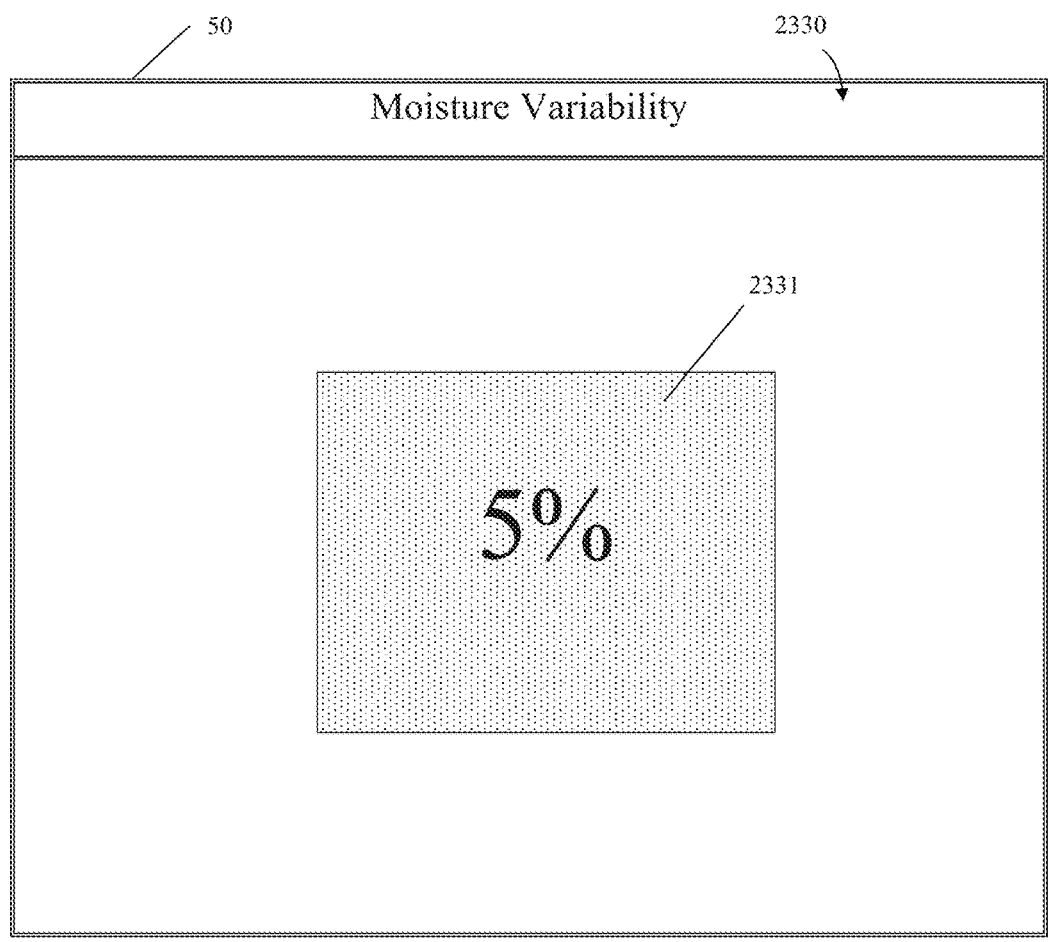
FIG. 51 illustrates an embodiment of a moisture variability screen.

In another embodiment, the uniformity of moisture or moisture variability can be measured and displayed on monitor 50. An example of monitor 50 displaying on screen 2320 uniformity of moisture 2321 and/or displaying on screen 2330 moisture variability 2331 are illustrated in FIGS. 50 and 51. One or both can be displayed, or both can be displayed on the same screen. Uniformity of moisture is 1-moisture variability. Any of the moisture readings can be used, such as capacitance moisture, seed germination moisture, or even volumetric water content or matrix potential or days until germination, to calculate uniformity of moisture and moisture variability. Moisture variability is deviation from the average measurement. In one embodiment, moisture variability is calculated by dividing the standard deviation by the average using any of the moisture measurements. This provides a percentage. Any other mathematical method for expressing variation in measurement can also be used. In one embodiment, root mean square can be used in place of the standard deviation. In addition to displaying the result on monitor 50, the result can be accompanied by a color. For example, the font color of the reported result or the screen color on monitor 50 can use green for values within the acceptable level and another color, such as yellow or red, for values that are unacceptable. For the above days to germination, this is determined by creating a database by placing seeds in different moisture levels and measuring the days until germination. Uniformity of moisture and moisture variability is then the variability in the days until germination.

Depending on the uniformity of moisture reading or moisture variability reading, the depth of planting can be adjusted as described herein. In one embodiment, depth can be adjusted to maximize uniformity of moisture and minimize moisture variability.

Figure 52:
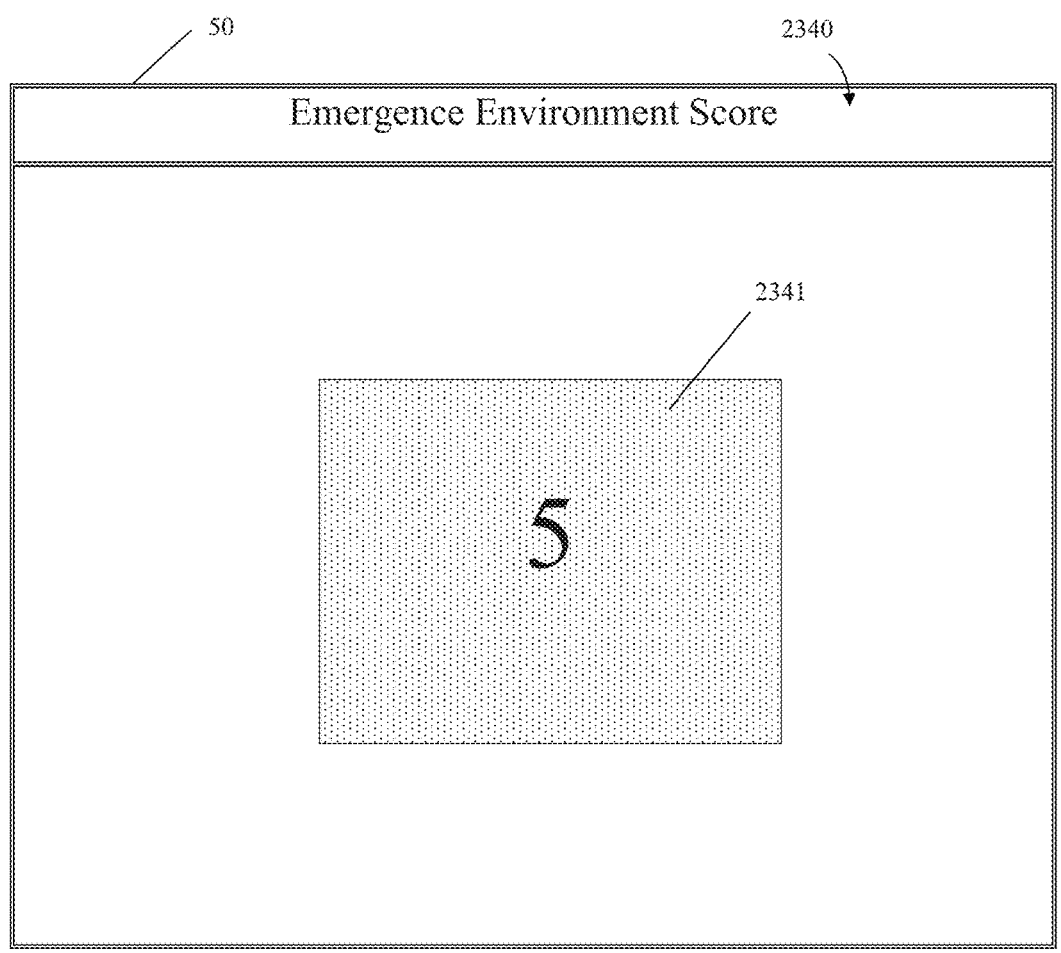
FIG. 52 illustrates an embodiment of an emergence environment score.

In another embodiment, an emergence environment score can be calculated and displayed on monitor 50. An example of monitor 50 displaying on screen 2340 an emergence environment score 2441 is illustrated in FIG. 52. The emergence environment score is a combination of temperature and moisture correlated to how long a seed takes to germinate under these conditions. A database can be created by placing seeds in different combinations of temperature and moisture and measuring the days until germination. The emergence environment score displayed on monitor 50 can be the days until germination from the database. In another embodiment, the emergence environment score can be the percentage of seeds planted that will germinate within a selected number of days. The selected number of days can be input into monitor 50. In another embodiment, a scaled score can be used that is based on a scale of 1 to 10 with 1 representing the shortest number of days that a seed takes to germinate and 10 representing the longest number of days that a seed takes to germinate. For example, if a seed can germinate within 2 days, this is assigned a value of 1, and if the longest that the seed takes to germinate is 17 days, this is assigned a value of 10. In addition to displaying the result on monitor 50, the result can be accompanied by a color. For example, the font color of the reported result or the screen color on monitor 50 can use green for values within the selected number of days and another color, such as yellow or red, for values that are greater than the selected number of days.

Depending on the emergence environment score, the depth of planting can be adjusted as described herein. In one embodiment, depth can be adjusted to minimize the number of days to germination.

Figure 46:
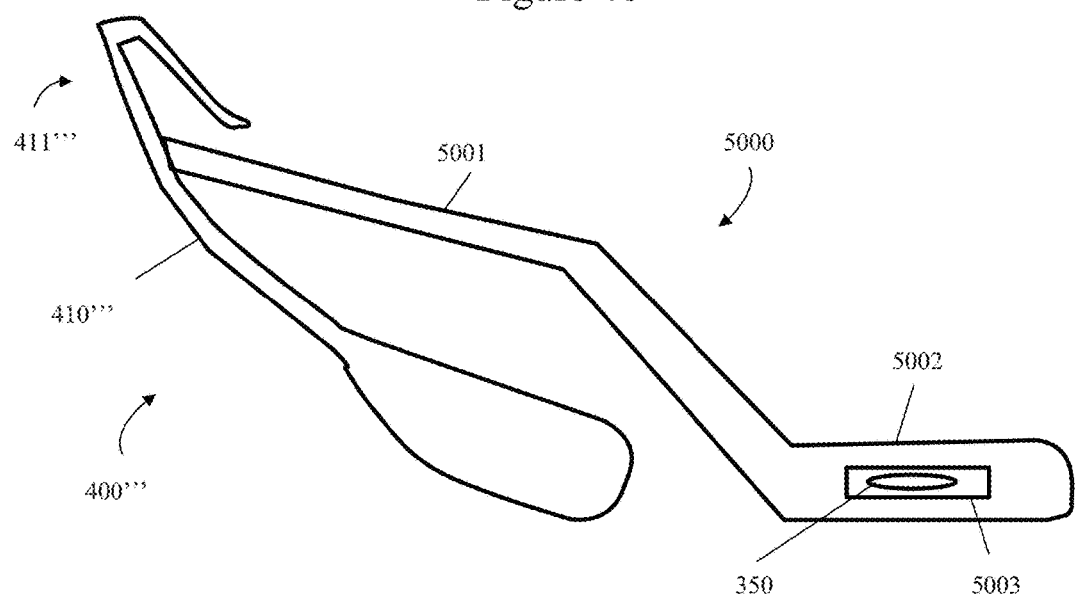
FIG. 46 is a side view of a seed firmer and sensor arm according to one embodiment.

In another embodiment, any of the previous embodiments can be in a device separate from seed firmer 400, 400'. As illustrated in FIG. 46, any of the sensors described herein (sensor 350 is illustrated in the Figure) is disposed in sensor arm 5000. Sensor arm 5000 has flexible portion 5001 that is attached to seed firmer 400' at an end of flexible portion 410' of seed firmer 400''' proximate to bracket insert portion 411'''. At the opposite end of flexible portion 5001 is base 5002. Sensor 350 is disposed in base 5002 behind lens 5003. While it is desirable for any of the sensors to be in seed firmer 400''', there may be times when a difference in the applied force is needed. In one embodiment, seed firmer 400''' may need a lower amount of force to firm a seed but a greater force is needed to keep the sensor in soil contact. A different amount of stiffness can be designed into flexible portion 5001 as compared to flexible portion 410'''. By having the seed firmed by seed firmer 400, 400' first, then the biasing from sensor arm 5000 does not touch the seed that is already firmed into trench 38 or does not move the seed if contact is made.

In other embodiments, any of the sensors do not need to be disposed in a firmer, and in particular any of the embodiments illustrated in FIGS. 27A to 54. The sensors can be in any implement that is disposed on an agricultural implement in contact with the soil. For example, firmer body 490 can be mounted to any bracket and disposed anywhere on an agricultural implement and in contact with soil. Examples of an agricultural implement include, but are not limited to, planters, harvesters, sprayers, side dress bars, tillers, fertilizer spreaders, and tractor.

Figure 49:
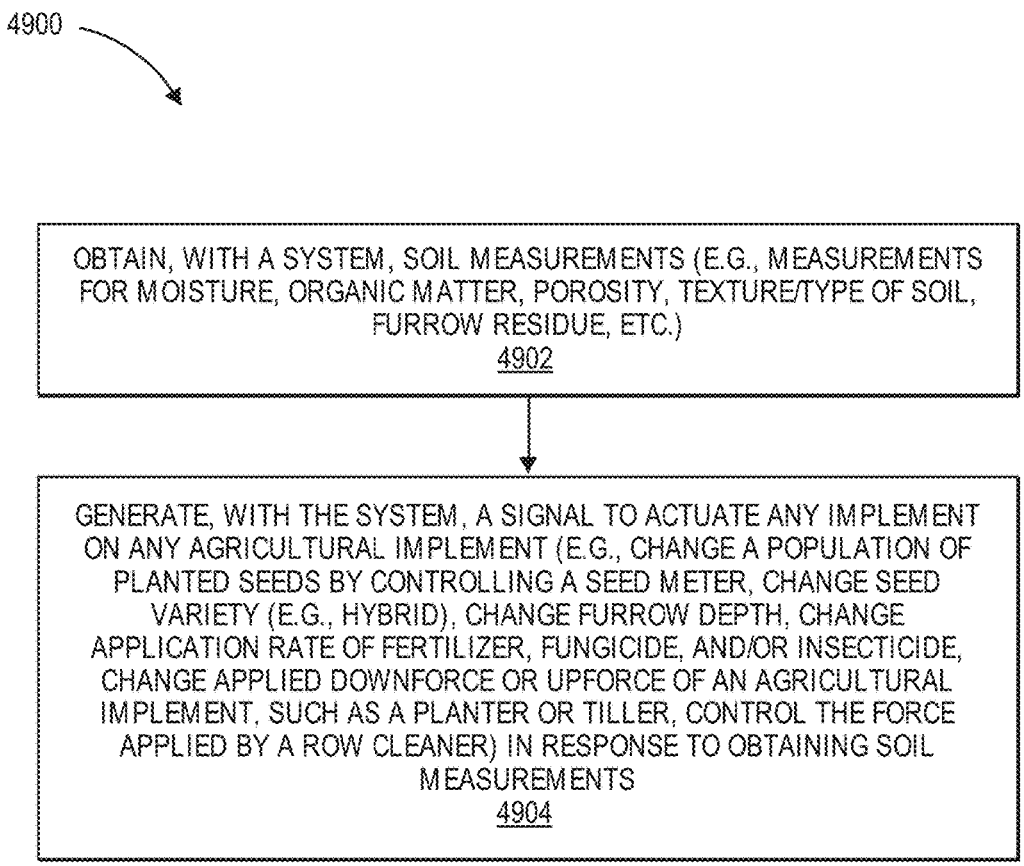
FIG. 49 illustrates a flow diagram of one embodiment for a method 4900 of obtaining soil measurements and then generating a signal to actuate any implement on any agricultural implement.

FIG. 49 illustrates a flow diagram of one embodiment for a method 4900 of obtaining soil measurements and then generating a signal to actuate any implement on any agricultural implement. The method 4900 is performed by hardware (circuitry, dedicated logic, etc.), software (such as is run on a general purpose computer system or a dedicated machine or a device), or a combination of both. In one embodiment, the method 4900 is performed by at least one system or device (e.g., monitor 50, soil monitoring system, seed firmer, sensors, implement, row unit, etc.). The system executes instructions of a software application or program with processing logic. The software application or program can be initiated by a system or may notify an operator or user of a machine (e.g., tractor, planter, combine) depending on whether soil measurements cause a signal to actuate an implement.

In any embodiment herein, at operation 4902, a system or device (e.g., soil monitoring system, monitor 50, seed firmer, sensors) can obtain soil measurements (e.g., measurements for moisture, organic matter, porosity, texture/type of soil, furrow residue, etc.). At operation 4904, the system or device (e.g., soil monitoring system, monitor 50) can generate a signal to actuate any implement on any agricultural implement (e.g., change a population of planted seeds by controlling a seed meter, change seed variety (e.g., hybrid), change furrow depth, change application rate of fertilizer, fungicide, and/or insecticide, change applied downforce or upforce of an agricultural implement, such as a planter or tiller, control the force applied by a row cleaner) in response to obtaining soil measurements. This can be done in real time on the go. Examples of soil measurements that can be measured and the control of implements include, but are not limited to:

A) moisture, organic matter, porosity, or texture/type of soil to change a population of planted seeds by controlling a seed meter;

B) moisture, organic matter, porosity, or texture/type of soil to change seed variety (e.g., hybrid);

C) moisture, organic matter, porosity, or texture/type of soil to change furrow depth:

D) moisture, organic matter, porosity, or texture/type of soil to change application rate of fertilizer, fungicide, and/or insecticide:

E) moisture, organic matter, porosity, or texture/type of soil to change applied downforce or upforce of an agricultural implement, such as a planter or tiller:

F) furrow residue to control the force applied by a row cleaner.

Data Processing and Display

Figure 20:
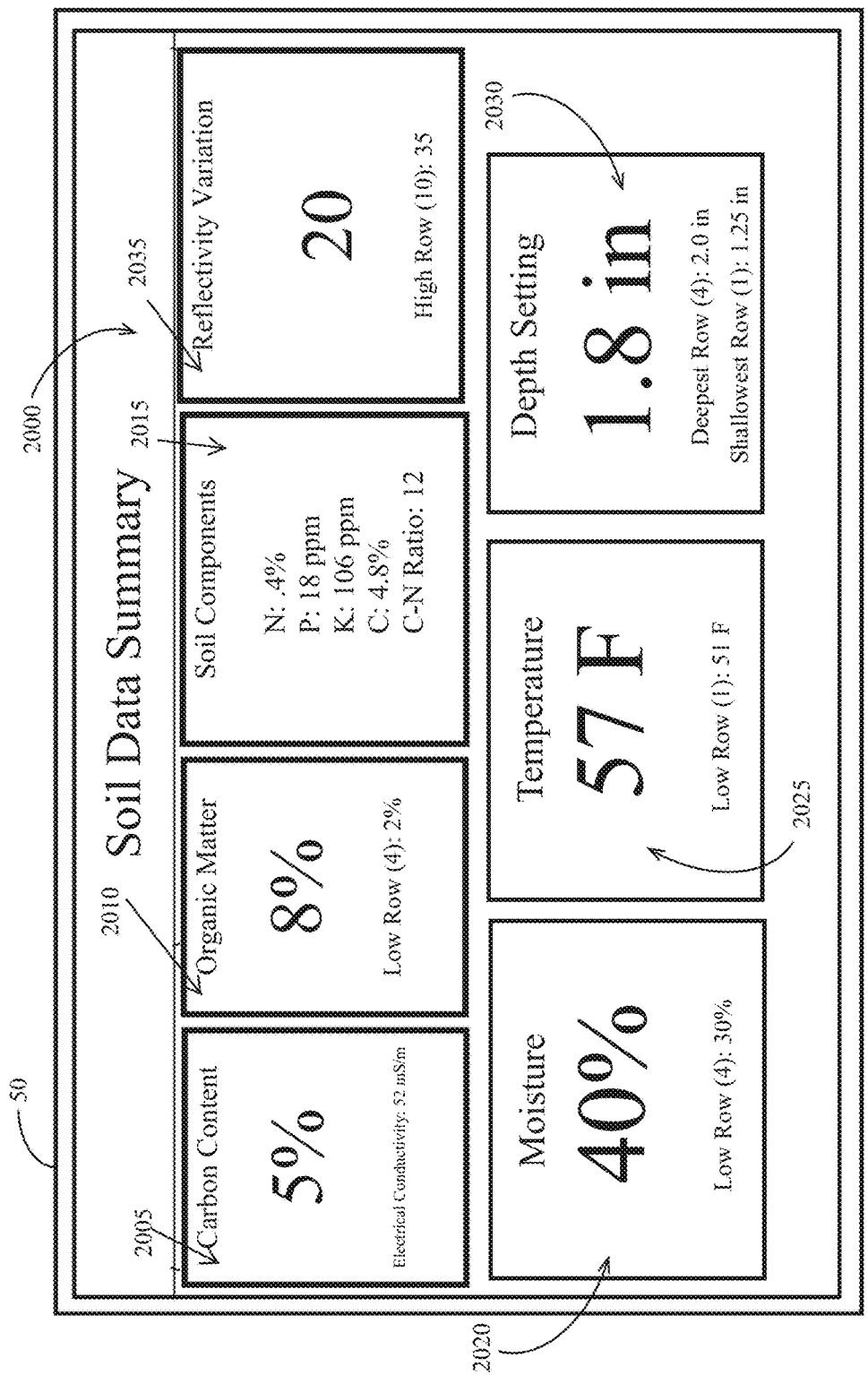
FIG. 20 illustrates an embodiment of a soil data display screen.

Referring to FIG. 20, the implement monitor 50 may display a soil data summary 2000 displaying a representation (e.g., numerical or legend-based representation) of soil data gathered using the seed firmer 400 and associated sensors. The soil data may be displayed in windows such as a soil moisture window 2020 and soil temperature window 2025. A depth setting window 2030 may additionally show the current depth setting of the row units of the implement, e.g., the depth at which the seed farmers 400 are making their respective measurements. A reflectivity variation window 2035 may show a statistical reflectivity variation during a threshold period (e.g., the prior 30 seconds) or over a threshold distance traveled by the implement (e.g., the preceding 30 feet). The statistical reflectivity variation may comprise any function of the reflectivity signal (e.g., generated by each reflectivity sensor 350) such as the variance or standard deviation of the reflectivity signal. The monitor 50 may additionally display a representation of a predicted agronomic result (e.g., percentage of plants successfully emerged) based on the reflectivity variation value. For example, values of reflectivity emergence may be used to look up a predicted plant emergence value in an empirically-generated database (e.g., stored in memory of the implement monitor 50 or stored in and updated on a remote server in data communication with the implement monitor) associating reflectivity values with predicted plant emergence.

Each window in the soil data summary 2000 preferably shows an average value for all row units ("rows") at which the measurement is made and optionally the row unit for which the value is highest and/or lowest along with the value associated with such row unit or row units. Selecting (e.g., clicking or tapping) each window preferably shows the individual (row-by-row) values of the data associated with the window for each of the row units at which the measurement is made.

A carbon content window 2005 preferably displays an estimate of the soil carbon content. The carbon content is preferably estimated based on the electrical conductivity measured by the electrical conductivity sensors 370, e.g., using an empirical relation or empirical look-up table relating electrical conductivity to an estimated carbon content percentage. The window 2005 preferably additionally displays the electrical conductivity measured by the electrical conductivity sensors 370.

An organic matter window 2010 preferably displays an estimate of the soil organic matter content. The organic matter content is preferably estimated based on the reflectivity at one or a plurality of wavelengths measured by the reflectivity sensors 350, e.g., using an empirical relation or empirical look-up table relating reflectivity at one or a plurality of wavelengths to an estimated organic matter percentage.

A soil components window 2015 preferably displays an estimate of the fractional presence of one or a plurality of soil components, e.g., nitrogen, phosphorous, potassium, and carbon. Each soil component estimate is preferably based on the reflectivity at one or a plurality of wavelengths measured by the reflectivity sensors 350, e.g., using an empirical relation or empirical look-up table relating reflectivity at one or a plurality of wavelengths to an estimated fractional presence of a soil component. In some embodiments, the soil component estimate is preferably determined based on a signal or signals generated by the spectrometer 373. In some embodiments, the window 2015 additionally displays a ratio between the carbon and nitrogen components of the soil.

A moisture window 2020 preferably displays an estimate of soil moisture. The moisture estimate is preferably based on the reflectivity at one or a plurality of wavelengths (e.g., 930 or 940 nanometers) measured by the reflectivity sensors 350, e.g., using an empirical relation or empirical look-up table relating reflectivity at one or a plurality of wavelengths to an estimated moisture. In some embodiments, the moisture measurement is determined as disclosed in the '975 application.

A temperature window 2025 preferably displays an estimate of soil temperature. The temperature estimate is preferably based on the signal generated by one or more temperature sensors 350.

A depth window 2030 preferably displays the current depth setting. The monitor 50 preferably also enables the user to remotely actuate the row unit 200 to a desired trench depth as disclosed in International Patent Application No. PCT/US2014/029352, incorporated herein by reference.

Figure 21:
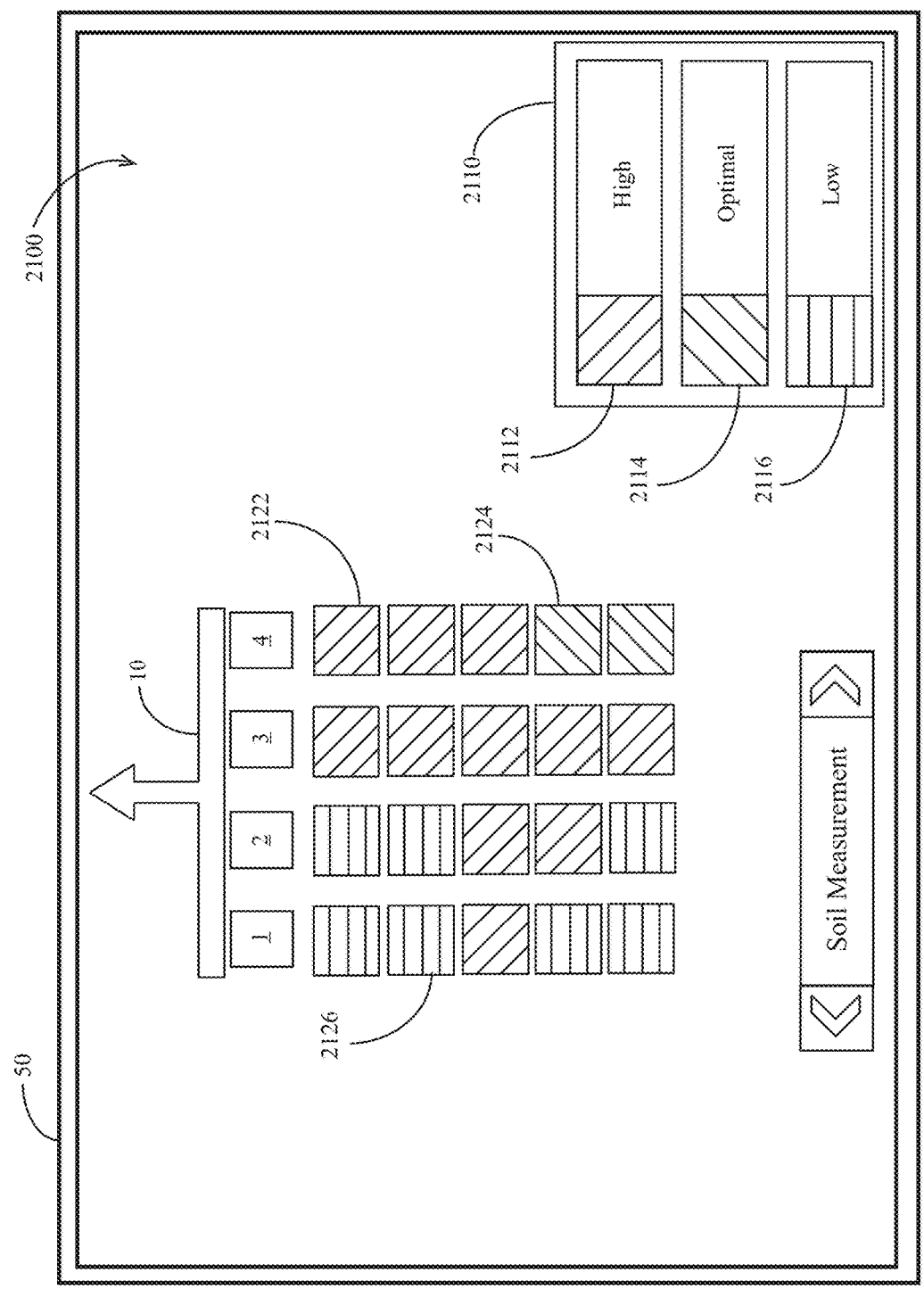
FIG. 21 illustrates an embodiment of a spatial map screen.

Turning to FIG. 21, the monitor 50 is preferably configured to display one or more map windows 2100 in which a plurality of soil data, measurement, and/or estimate values (such as the reflectivity variation) are represented by blocks 2122, 2124, 2126, each block having a color or pattern associating the measurement at the block position to the ranges 2112, 2114, 2116, respectively (of legend 2110) in which the measurements fall. A map window 2100 is preferably generated and displayed for each soil data, measurement, and/or estimate displayed on the soil data screen 2000, preferably including carbon content, electrical conductivity, organic matter, soil components (including nitrogen, phosphorous, and potassium), moisture and soil temperature. The subsets may correspond to numerical ranges of reflectivity variation. The subsets may be named according to an agronomic indication empirically associated with the range of reflectivity variation. For example, a reflectivity variation below a first threshold at which no emergence failure is predicted may be labeled "Good"; a reflectivity variation between the first threshold and a second threshold at which predicted emergence failure is agronomically unacceptable (e.g., is likely to affect yield by more than a yield threshold) may be labeled "Acceptable" a reflectivity variation above the second threshold may be labeled "Poor emergence predicted".

Figure 17:
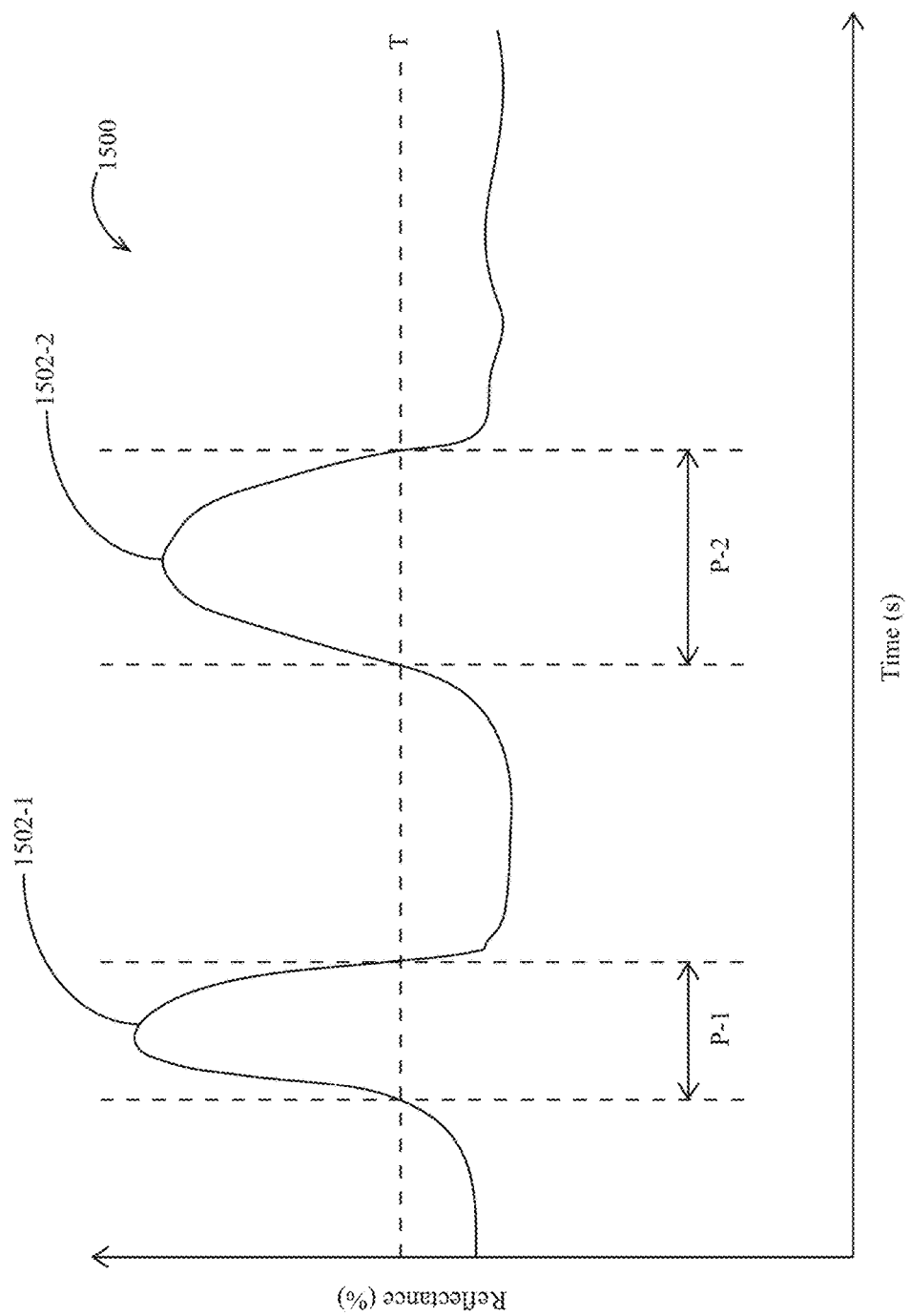
FIG. 17 is a plot of a reflectivity sensor signal.
Figure 22:
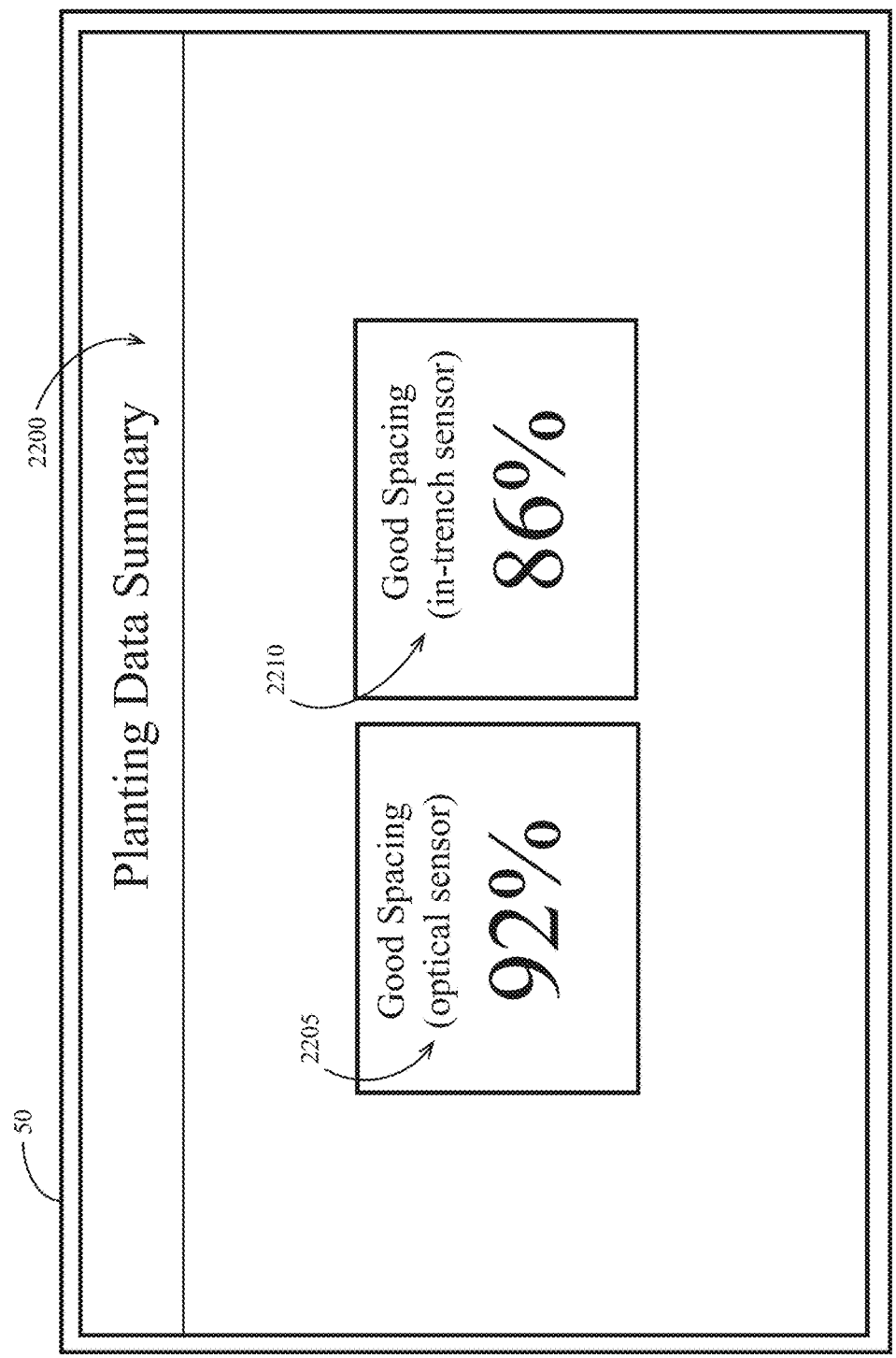
FIG. 22 illustrates an embodiment of a seed planting data display screen.

Turning to FIG. 22, the monitor 50 is preferably configured to display one or more planting data windows including planting data measured by the seed sensors 305 and/or the reflectivity sensors 350. The window 2205 preferably displays a good spacing value calculated based on seed pulses from the optical (or electromagnetic) seed sensors 305. The window 2210 preferably displays a good spacing value based on seed pulses from the reflectivity sensors 350. Referring to FIG. 17, seed pulses 1502 in a reflectivity signal 1500 may be identified by a reflectance level exceeding a threshold T associated with passage of a seed beneath the seed firmer. A time of each seed pulse 1502 may be established to be the midpoint of each period P between the first and second crossings of the threshold T. Once times of seed pulses are identified (whether from the seed sensor 305 or from the reflectivity sensor 350), the seed pulse times are preferably used to calculate a good spacing value as disclosed in U.S. patent application Ser. No. 13/752,031 ("the '031 application"), incorporated by reference herein. In some embodiments, in addition to good spacing other seed planting information (including, e.g., population, singulation, skips and multiples) is also calculated and displayed on the screen 2200 according to the methods disclosed in the '031 application. In some embodiments, the same wavelength (and/or the same reflectivity sensor 350) is used for seed detection as moisture and other soil data measurements; in some embodiments the wavelength is about 940 nanometers. Where the reflectivity signal 1500 is used for both seed detection and soil measurement (e.g., moisture), the portion of the signal identified as a seed pulse (e.g., the periods P) are preferably not used in calculating the soil measurement; for example, the signal during each period P may be assumed to be a line between the times immediately prior to and immediately following the period P, or in other embodiments it may be assumed to be the average value of the signal during the previous 30 seconds of signal not falling within any seed pulse period P. In some embodiments, the screen 2200 also displays a percentage or absolute difference between the good spacing values or other seed planting information determined based on seed sensor pulses and the same information determined based on reflectivity sensor pulses.

In some embodiments, seed sensing is improved by selectively measuring reflectivity at a wavelength or wavelengths associated with a characteristic or characteristics of the seed being planted. In some such embodiments, the system 300 prompts the operator to select a crop, seed type, seed hybrid, seed treatment and/or another characteristic of the seed to be planted. The wavelength or wavelengths at which reflectivity is measured to identify seed pulses is preferably selected based on the seed characteristic or characteristics selected by the operator.

In some embodiments, the "good spacing" values are calculated based on both the seed pulse signals generated by the optical or electromagnetic seed sensors 305 and the reflectivity sensors 350.

In some such embodiments, the "good spacing" value for a row unit is based on the seed pulses generated the reflectivity sensor 350 associated with the row unit, which are filtered based on the signal generated by the optical seed sensor 305 on the same row unit. For example, a confidence value may be associated each seed pulse generated by the optical seed sensor, e.g., directly related to the amplitude of the optical seed sensor seed pulse; that confidence value may then be modified based on the optical seed sensor signal, e.g., increased if a seed pulse was observed at the optical seed sensor within a threshold period prior to the reflectivity sensor seed pulse, and decreased if the a seed pulse was not observed at the optical seed sensor within a threshold period prior to the reflectivity sensor seed pulse. A seed pulse is then recognized and stored as a seed placement if the modified confidence value exceeds a threshold.

In other such embodiments, the "good spacing" value for a row unit is based on the seed pulses generated the optical seed sensor 305 associated with the row unit, which are modified based on the signal generated by the reflectivity sensor 350 on the same row unit. For example, the seed pulses generated by the optical seed sensor 305 may be associated with the time of the next seed pulse generated by the reflectivity sensor 350. If no seed pulse is generated by the reflectivity sensor 350 within a threshold time after the seed pulse generated by the seed sensor 305, then the seed pulse generated by the seed sensor 305 may be either ignored (e.g., if a confidence value associated with the seed sensor seed pulse is below a threshold) or adjusted by an average time delay between reflectivity sensor seed pulses and seed sensor seed pulses (e.g., the average time delay for the last 10, 100 or 300 seeds).

In addition to displaying seed planting information such as good spacing values, in some embodiments the seed pulses measured may be used to time deposition of in-trench liquid and other crop inputs in order to time application such that the applied crop input lands on the seed, adjacent to the seed, or between seeds as desired. In some such embodiments, a liquid applicator valve selectively permitting liquid to flow from outlet 507 of the liquid conduit 506 is briefly opened a threshold time (e.g., 0 seconds, 1 ms, 10 ms, 100 ms or 1 second) after a seed pulse 1502 is identified in signal 1500 from the reflectivity sensor 350 associated with the same row unit 200 as the liquid applicator valve.

A signal generated by the reflectivity sensor may also be used to identify the presence of crop residue (e.g., corn stalks) in the seed trench. Where reflectivity in a range of wavelengths associated with crop residue (e.g., between 560 and 580 nm) exceeds a threshold, the system 300 preferably determines that crop residue is present in the trench at the current GPS-reported location. The spatial variation in residue may then be mapped and displayed to a user. Additionally, the downpressure supplied to a row cleaner assembly (e.g., a pressure-controlled row cleaner as disclosed in U.S. Pat. No. 8,550,020, incorporated herein by reference) may be adjusted either automatically by the system 300 in response to the identification of residue or adjusted by the user. In one example, the system may command a valve associated with a row cleaner downpressure actuator to increase by 5 psi in response to an indication that crop residue is present in the seed trench. Similarly, a closing wheel downforce actuator may also be adjusted by the system 300 or the operator in response to an indication that crop residue is present in the seed trench.

In some embodiments, an orientation of each seed is determined based on the width of reflectivity-based seed pulse periods P. In some such embodiments, pulses having a period longer than a threshold (an absolute threshold or a threshold percentage in excess of the mean pulse period) are categorized in a first category while pulses having a shorter period than the threshold are categorized in a second category. The first and second category preferably correspond to first and second seed orientations. Percentages of seeds over the previous 30 seconds falling in the first and/or second category may be displayed on the screen 2200. The orientation of each seed is preferably mapped spatially using the GPS coordinates of the seed such that individual plant performance may be compared to seed orientation during scouting operations.

In some embodiments, a determination of seed-to-soil contact is made based on the existence or lack of a recognized seed pulse generated by the reflectivity sensor 350. For example, where a seed pulse is generated by the optical seed sensor 305 and no seed pulse is generated by the reflectivity sensor 350 within a threshold time after the optical seed sensor seed pulse, a "Poor" seed-to-soil contact value is preferably stored and associated with the location at which the reflectivity sensor seed pulse was expected. An index of seed-to-soil contact may be generated for a row or rows by comparing the number of seeds having "Poor" seed-to-soil contact over a threshold number of seeds planted, distance traveled, or time elapsed. The operator may then be alerted via the monitor 50 as to the row or rows exhibiting seed-to-soil contact below a threshold value of the index. Additionally, the spatial variation in seed-to-soil contact may be mapped and displayed to the user. Additionally, a criterion representing the percentage of seeds firmed (e.g., not having "Poor" seed-to-soil contact) over a preceding time period or number of seeds may be displayed to the operator.

In one embodiment, the depth of planting can be adjusted based on soil properties measured by the sensors and/or camera so that seeds are planted where the desired temperature, moisture, and/or conductance is found in trench 38. A signal can be sent to the depth adjustment actuator 380 to modify the position of the depth adjustment rocker 268 and thus the height of the gauge wheels 248 to place the seed at the desired depth. In one embodiment, an overall goal is to have the seeds germinate at about the same time. This leads to greater consistency and crop yield. When certain seeds germinate before other seeds, the earlier resulting plants can shade out the later resulting plants to deprive them of needed sunlight and can disproportionately take up more nutrients from the surrounding soil, which reduces the yield from the later germinating seeds. Days to germination is based on a combination of moisture availability (soil moisture tension) and temperature.

In another embodiment, the depth can be adjusted based on a combination of current temperature and moisture conditions in the field and the predicted temperature and moisture delivery from a weather forecast. This process is described in U.S. Patent Publication No. 2016/0037709, which is incorporated herein by reference.

In any of the foregoing embodiments for depth control for moisture, the control can be further limited by a minimum threshold temperature. A minimum threshold temperature (for example 10° C. (50° F.)) can be set so that the planter will not plant below a depth where the minimum threshold temperature is. This can be based on the actual measured temperature or by accounting for the temperature measured at a specific time of day. Throughout the day, soil is heated by sunshine or cooled during night time. The minimum threshold temperature can be based on an average temperature in the soil over a 24 hour period. The difference between actual temperature at a specific time of day and average temperature can be calculated and used to determine the depth for planting so that the temperature is above a minimum threshold temperature.

The soil conditions of conductivity, moisture, temperature, and/or reflectance can be used to directly vary planted population (seeds/acre), nutrient application (gallons/acre), and/or pesticide application (lb./acre) based off of zones created by organic matter, soil moisture, and/or electrical conductivity.

In another embodiment, any of the sensors or camera can be adapted to harvest energy to power the sensor and/or wireless communication. As the sensors are dragged through the soil, the heat generated by soil contact or the motion of the sensors can be used as an energy source for the sensors.

Temperature Sensor

Figure 55:
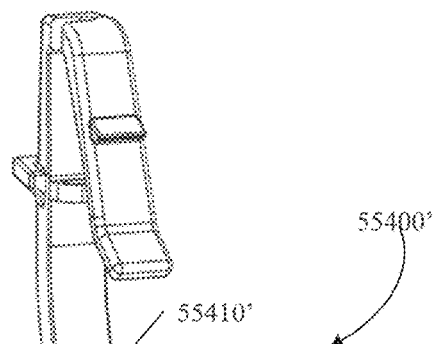
FIG. 55 is a perspective view of a seed firmer according to one embodiment.
Figure 56:
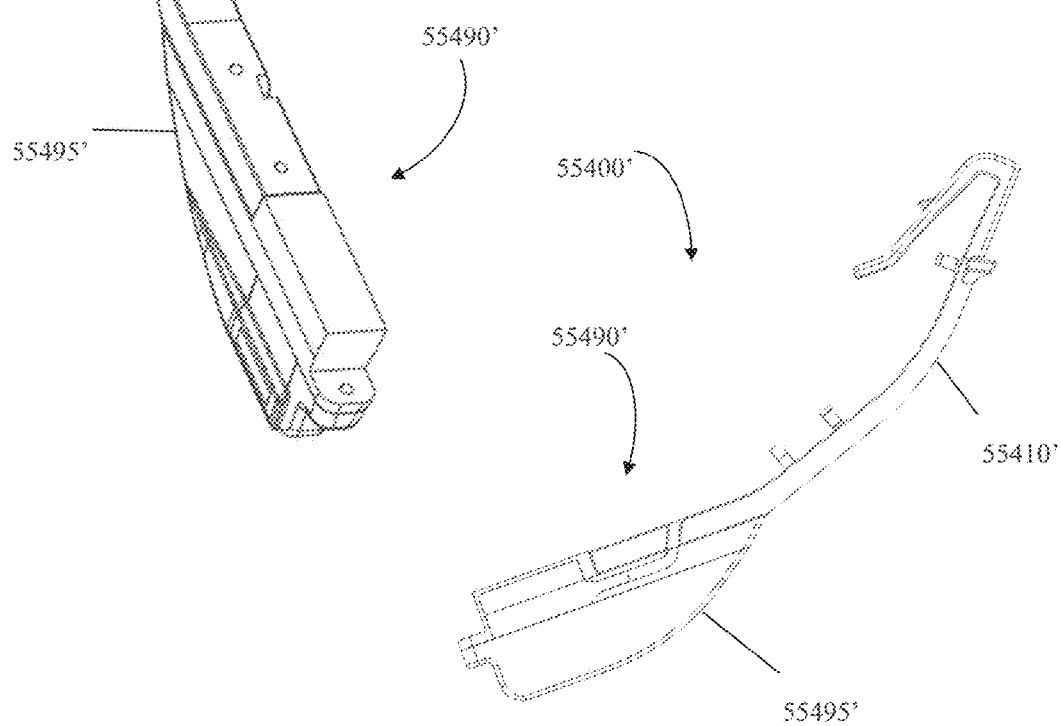
FIG. 56 is a side view of the seed firmer of FIG. 55.
Figure 57:
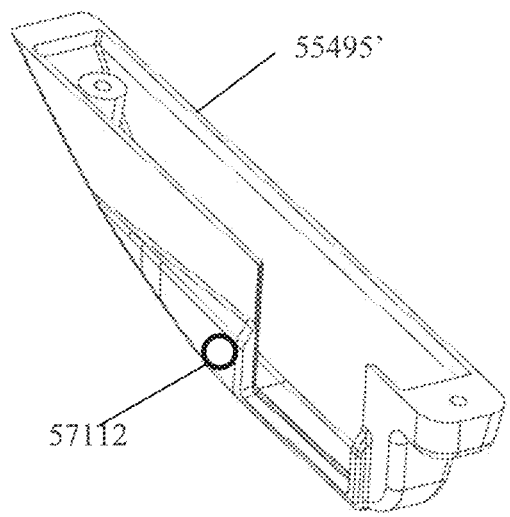
FIG. 57 is a perspective view of the firmer base according to one embodiment.
Figure 58:
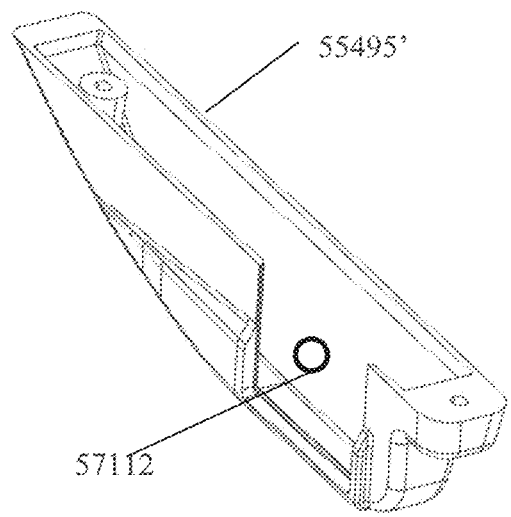
FIG. 58 is a perspective view of the firmer base according to one embodiment.

In some embodiments, a thermopile 59110 is disposed in an implement, such as seed firmer 55400'. Seed firmer 55400', which is described in U.S. Application No. 62/482,116, is illustrated in FIGS. 55 and 56. Seed firmer 55400' has a flexible portion 55410', a firmer body 55490', and a firmer base 55495'. FIGS. 57 and 58 illustrate alternative embodiments for a window 57112 disposed in firmer base 55495'. Window 57112 is an infrared transparent material that allows infrared radiation to be detected by thermopile 59110 as illustrated in FIG. 59. In FIG. 57, window 57112 can be disposed on the same side as other sensors (not shown). In FIG. 58, window 57112 can be disposed on a side opposite to other sensors (not shown).

By infrared transparent, it is meant that the material is of a type and thickness that allows at least 50% of the infrared radiation entering the material to pass through the material. In other embodiments, the amount is at least 60%, at least 70%, at least 80%, or at least 90%.

In other embodiments, window 57112 is not transparent to visual light. In other embodiments, window 57112 is translucent to visual light or is opaque to visual light.

In one embodiment, window 57112 is UHMW polyethylene. UHMW polyethylene is generally defined as a polyethylene having a weight average molecular weight of at least 3 million, or in other embodiments, 3 million to 7 million. In one embodiment, the UHMW polyethylene has a thickness to allow about 80% of the infrared radiation to pass through. In one embodiment, the thickness is 0.5 mm (0.02 inches). UHMW polyethylene has scratch resistance for operating in contact with soil.

Thermopile 59110 measures the amount of infrared radiation received. In one embodiment, thermopile 59110 is a TMP006 infrared thermopile sensor in a chip-scale package from Texas Instruments.

FIG. 59 illustrates an embodiment with thermopile 59110 disposed on a circuit board 59111 and disposed at a distance from window 57112 to have a selected field of view. In certain embodiments, the field of view is selected to be at least 70° up to 180°. In other embodiments, the field of view is 90° to 150°, 110° to 130°, or about 120°. In other embodiments, the field of view can be restricted by including a shroud 60113 disposed over thermopile 59111 as illustrated in FIGS. 60A and 60B. Shroud 60113 has an aperture 60114 that restricts the field of view of thermopile 59110.

Figure 61:
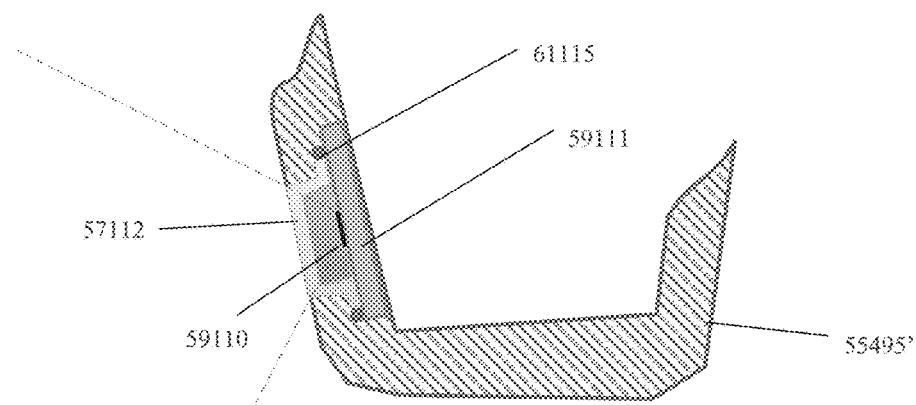
FIG. 61 illustrates a thermopile and window disposed in a body according to one embodiment.

FIG. 61 illustrates an embodiment for disposing thermopile 59110 in firmer base 55495'. In this embodiment, window 57112 is a box shaped cover that is disposed over thermopile 59110 and circuit board 59111 and disposed in an opening in firmer base 55495'. An O-ring 61115 can be disposed around window 57112 to provide a seal.

Figures 62, 63, 64:
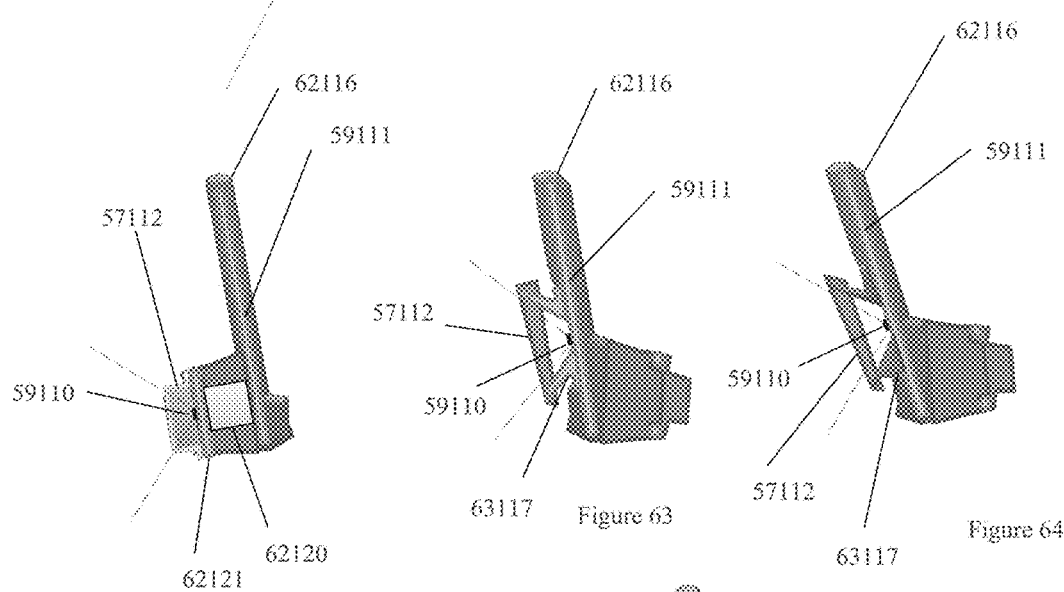
FIG. 62 illustrates a thermopile and window disposed in a body according to one embodiment.
FIG. 63 illustrates a thermopile and window disposed in a body according to one embodiment.
FIG. 64 illustrates a thermopile and window disposed in a body according to one embodiment.

FIGS. 62-64 illustrate other mounting arrangements. Firmer base 55495' is removed for clarity.

FIG. 62 illustrates an embodiment to place thermopile 59110 closer to the opening in firmer base 55495' when disposed on a mounting frame 62116. Mounting frame 62116 is used to assemble and hold the parts within firmer base 55495'. Circuit board 59111 is disposed in mounting frame 62116. An extender 62120 connects circuit board 59111 to circuit board 62121. Thermopile 110 is disposed on circuit board 62121. Window 57112 is disposed over thermopile 59110 and circuit board 62121 similar to the embodiment in FIG. 61.

FIG. 63 illustrates two different embodiments. FIG. 63 illustrates thermopile 59110 being disposed opposite other sensors. FIG. 63 also illustrates window 57112 being disposed in the opening in firmer base 55495'. To space mounting frame 62116 away from window 57112, a lip 63117 is disposed between window 57112 to mounting frame 62116. In one embodiment, lip 63117 can be an elastomeric material, such as silicone rubber.

FIG. 64 is an alternative embodiment to FIG. 63 in which lip 63117 is unitary with mounting frame 62116.

Figure 65:
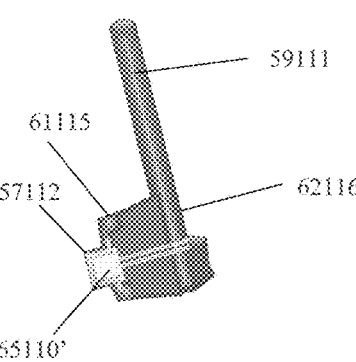
FIG. 65 illustrates a can thermopile and window disposed in a body according to one embodiment.

In another embodiment, thermopile 59110 is a can thermopile 65110'. FIG. 65 illustrates an arrangement for a can thermopile 65110' disposed on a circuit board 57111 and a window 57112.

In other embodiments, thermopile 59110 does not need to be disposed in a firmer 55400'. The thermopile 59110 can be in any implement that is disposed on an agricultural implement in contact with the soil. For example, firmer body 55490' can be mounted to any bracket and disposed anywhere on an agricultural implement and in contact with soil. Examples of an agricultural implement include, but are not limited to, planters, harvesters, sprayers, side dress bars, tillers, fertilizer spreaders, and tractor.

The arrangement of the thermopile and the selection of materials are suited to measuring soil temperature while traversing a field.

Figure 66:
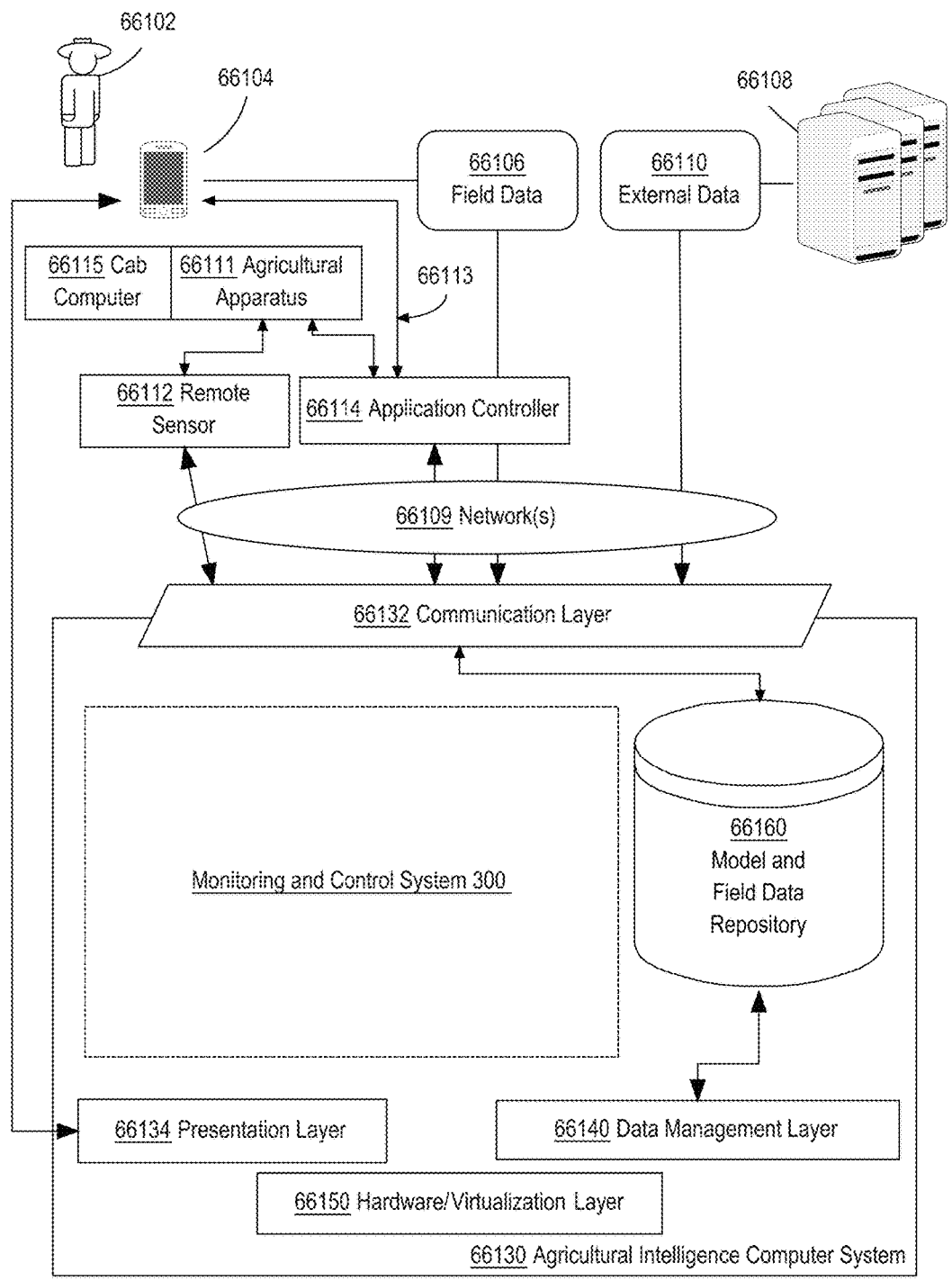
FIG. 66 illustrates an example computer system that is configured to perform the functions described herein, shown in a field environment with other apparatus with which the system may interoperate.

Additional embodiments are disclosed in sections according to the following outline:

1. General Overview
2. EXAMPLE AGRICULTURAL INTELLIGENCE COMPUTER SYSTEM
   2.1. STRUCTURAL OVERVIEW
   2.2. APPLICATION PROGRAM OVERVIEW
   2.3. DATA INGEST TO THE COMPUTER SYSTEM
   2.4. PROCESS OVERVIEW—AGRONOMIC MODEL TRAINING
   2.5. IMPLEMENTATION EXAMPLE—HARDWARE OVERVIEW
1. General Overview
2. Example Agricultural Intelligence Computer System
   2.1 Structural Overview FIG. 66 illustrates an example computer system that is configured to perform the functions described herein, shown in a field environment with other apparatus with which the system may interoperate. In one embodiment, a user 66102 owns, operates or possesses a field manager computing device 66104 in a field location or associated with a field location such as a field intended for agricultural activities or a management location for one or more agricultural fields. The field manager computer device 66104 is programmed or configured to provide field data 66106 to an agricultural intelligence computer system 66130 via one or more networks 66109.

Examples of field data 66106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source, method), (f) chemical application data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 66108 is communicatively coupled to agricultural intelligence computer system 66130 and is programmed or configured to send external data 66110 to agricultural intelligence computer system 66130 via the network(s) 66109. The external data server computer 66108 may be owned or operated by the same legal person or entity as the agricultural intelligence computer system 66130, or by a different person or entity such as a government agency, non-governmental organization (NGO), and/or a private data service provider. Examples of external data include weather data, imagery data, soil data, or statistical data relating to crop yields, among others. External data 66110 may consist of the same type of information as field data 66106. In some embodiments, the external data 66110 is provided by an external data server 66108 owned by the same entity that owns and/or operates the agricultural intelligence computer system 66130. For example, the agricultural intelligence computer system 66130 may include a data server focused exclusively on a type of data that might otherwise be obtained from third party sources, such as weather data. In some embodiments, an external data server 66108 may actually be incorporated within the system 66130.

An agricultural apparatus 66111 may have one or more remote sensors 66112 fixed thereon, which sensors are communicatively coupled either directly or indirectly via agricultural apparatus 66111 to the agricultural intelligence computer system 66130 and are programmed or configured to send sensor data to agricultural intelligence computer system 66130. Examples of agricultural apparatus 66111 include tractors, combines, harvesters, planters, trucks, fertilizer equipment, aerial vehicles including unmanned aerial vehicles, and any other item of physical machinery or hardware, typically mobile machinery, and which may be used in tasks associated with agriculture. In some embodiments, a single unit of apparatus 66111 may comprise a plurality of sensors 66112 that are coupled locally in a network on the apparatus; controller area network (CAN) is example of such a network that can be installed in combines, harvesters, sprayers, and cultivators. Application controller 66114 is communicatively coupled to agricultural intelligence computer system 66130 via the network(s) 66109 and is programmed or configured to receive one or more scripts that are used to control an operating parameter of an agricultural vehicle or implement from the agricultural intelligence computer system 66130. For instance, a controller area network (CAN) bus interface may be used to enable communications from the agricultural intelligence computer system 66130 to the agricultural apparatus 66111, such as how the CLIMATE FIELDVIEW DRIVE, available from The Climate Corporation, San Francisco, Calif., is used. Sensor data may consist of the same type of information as field data 66106. In some embodiments, remote sensors 66112 may not be fixed to an agricultural apparatus 66111 but may be remotely located in the field and may communicate with network 109.

The apparatus 66111 may comprise a cab computer 115 that is programmed with a cab application, which may comprise a version or variant of the mobile application for device 66104 that is further described in other sections herein. In an embodiment, cab computer 66115 comprises a compact computer, often a tablet-sized computer or smartphone, with a graphical screen display, such as a color display, that is mounted within an operator's cab of the apparatus 66111. Cab computer 66115 may implement some or all of the operations and functions that are described further herein for the mobile computer device 66104.

The network(s) 66109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 66. The various elements of FIG. 66 may also have direct (wired or wireless) communications links. The sensors 66112, controller 66114, external data server computer 66108, and other elements of the system each comprise an interface compatible with the network(s) 66109 and are programmed or configured to use standardized protocols for communication across the networks such as TCP/IP, Bluetooth, CAN protocol and higher-layer protocols such as HTTP, TLS, and the like.

Agricultural intelligence computer system 66130 is programmed or configured to receive field data 66106 from field manager computing device 66104, external data 66110 from external data server computer 66108, and sensor data from remote sensor 66112. Agricultural intelligence computer system 66130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 66114, in the manner described further in other sections of this disclosure.

In an embodiment, agricultural intelligence computer system 66130 is programmed with or comprises a communication layer 66132, presentation layer 66134, data management layer 66140, hardware/virtualization layer 66150, and model and field data repository 66160. "Layer," in this context, refers to any combination of electronic digital interface circuits, microcontrollers, firmware such as drivers, and/or computer programs or other software elements.

Communication layer 66132 may be programmed or configured to perform input/output interfacing functions including sending requests to field manager computing device 66104, external data server computer 66108, and remote sensor 66112 for field data, external data, and sensor data respectively. Communication layer 66132 may be programmed or configured to send the received data to model and field data repository 66160 to be stored as field data 66106.

Presentation layer 66134 may be programmed or configured to generate a graphical user interface (GUI) to be displayed on field manager computing device 66104, cab computer 66115 or other computers that are coupled to the system 66130 through the network 109. The GUI may comprise controls for inputting data to be sent to agricultural intelligence computer system 66130, generating requests for models and/or recommendations, and/or displaying recommendations, notifications, models, and other field data.

Data management layer 66140 may be programmed or configured to manage read operations and write operations involving the repository 66160 and other functional elements of the system, including queries and result sets communicated between the functional elements of the system and the repository. Examples of data management layer 66140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, distributed databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 66106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 66102 may specify identification data by accessing a map on the user device (served by the agricultural intelligence computer system 66130) and drawing boundaries of the field over the map. Such CLU selection or map drawings represent geographic identifiers. In alternative embodiments, the user may specify identification data by accessing field identification data (provided as shape files or in a similar format) from the U. S. Department of Agriculture Farm Service Agency or other source via the user device and providing such field identification data to the agricultural intelligence computer system.

In an example embodiment, the agricultural intelligence computer system 66130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 70:
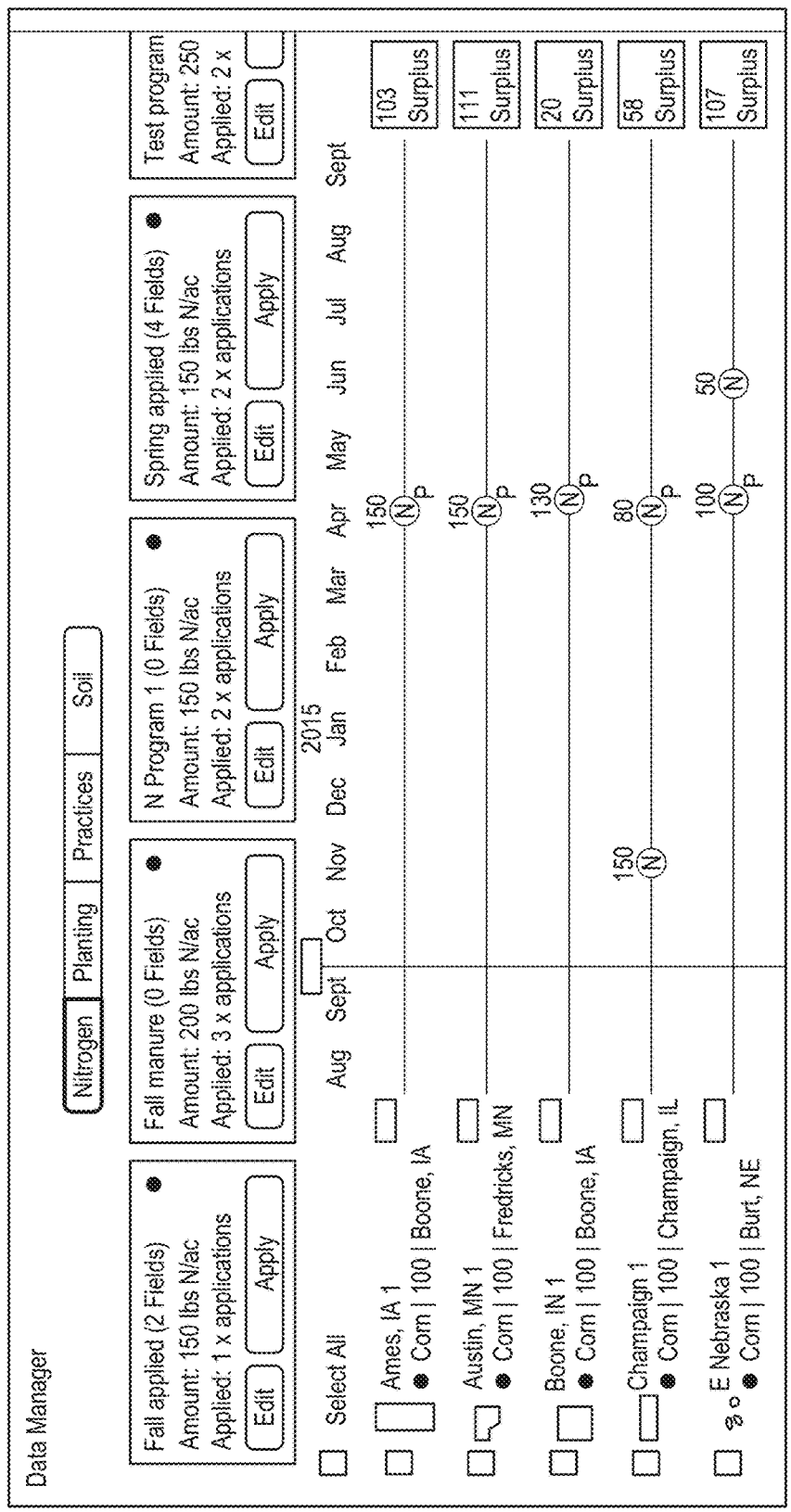
FIG. 70 depicts an example embodiment of a timeline view for data entry.

FIG. 70 depicts an example embodiment of a timeline view for data entry.

Using the display depicted in FIG. 70, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 70, the top two timelines have the "Spring applied" program selected, which includes an application of 150 lbs N/ac in early April. The data manager may provide an interface for editing a program. In an embodiment, when a particular program is edited, each field that has selected the particular program is edited. For example, in FIG. 70, if the "Spring applied" program is edited to reduce the application of nitrogen to 130 lbs N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 70, the interface may update to indicate that the "Spring applied" program is no longer being applied to the top field. While the nitrogen application in early April may remain, updates to the "Spring applied" program would not alter the April application of nitrogen.

FIG. 71 depicts an example embodiment of a spreadsheet view for data entry. Using the display depicted in FIG. 71, a user can create and edit information for one or more fields. The data manager may include spreadsheets for inputting information with respect to Nitrogen, Planting, Practices, and Soil as depicted in FIG. 71. To edit a particular entry, a user computer may select the particular entry in the spreadsheet and update the values. For example, FIG. 71 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 66160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In an embodiment, computer-executable instructions for implementing various aspects of system 66130 including but not limited to the instructions depicted in FIG. 67(*a*) and FIG. 67(*b*) and instructions for implementing aspects of monitoring and control system 300 comprise a set of one or more pages of main memory, such as RAM, in the agricultural intelligence computer system 66130 into which executable instructions have been loaded and which when executed cause the agricultural intelligence computing system to perform the functions or operations that are described herein with reference to those modules. For example, instructions implementing features of monitoring and control system 300 may comprise a set of pages in RAM that contain instructions which when executed cause performing the target identification functions that are described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each of the computer-implemented instructions shown in the drawings or described herein also may represent one or more files or projects of source code that are digitally stored in a mass storage device such as non-volatile RAM or disk storage, in the agricultural intelligence computer system 66130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 66130.

Figure 69:
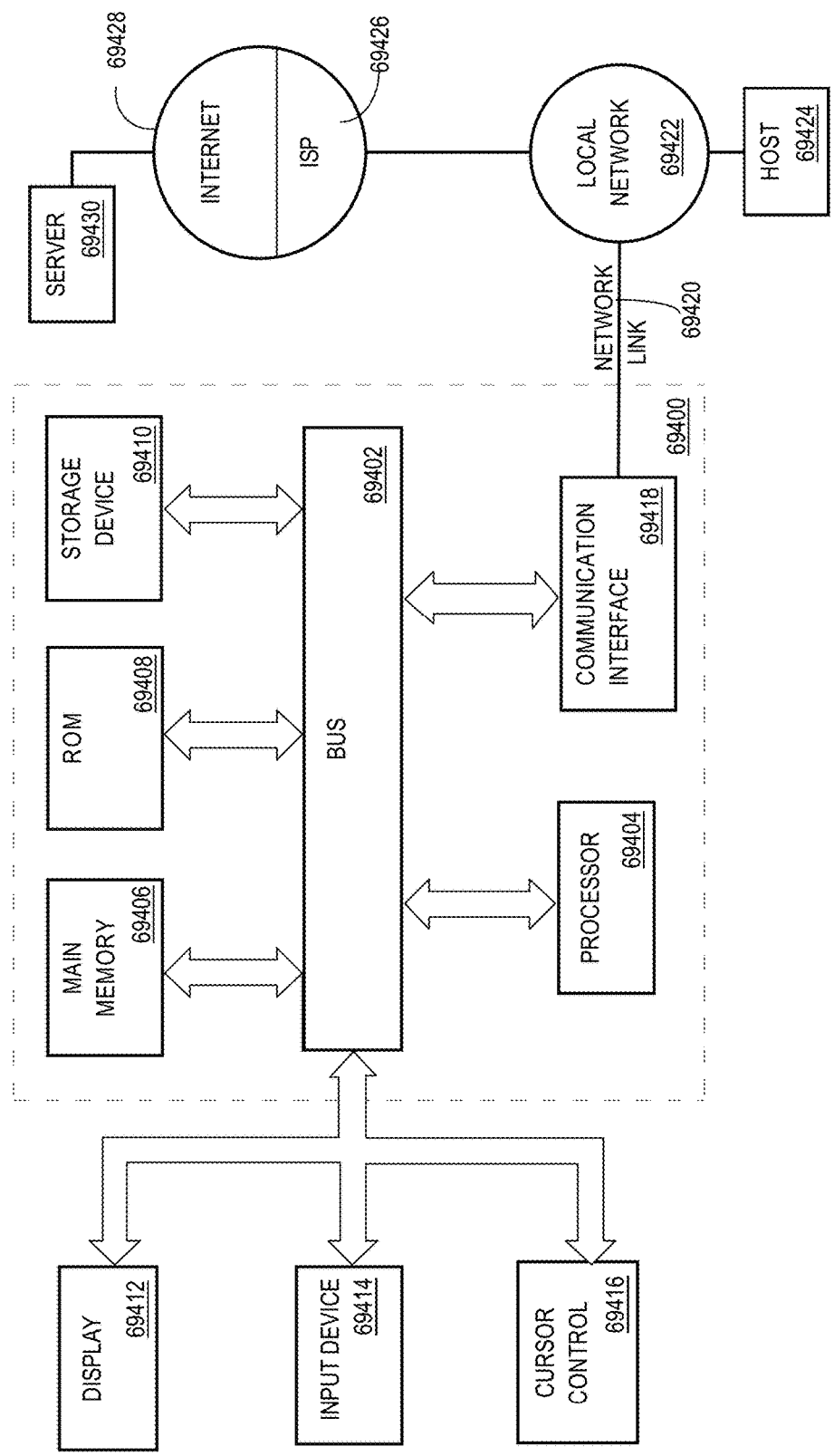
FIG. 69 is a block diagram that illustrates a computer system upon which an embodiment of the invention may be implemented.

Hardware/virtualization layer 66150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 69. The layer 66150 also may comprise programmed instructions that are configured to support virtualization, containerization, or other technologies.

For purposes of illustrating a clear example, FIG. 66 shows a limited number of instances of certain functional elements. However, in other embodiments, there may be any number of such elements. For example, embodiments may use thousands or millions of different mobile computing devices 104 associated with different users. Further, the system 66130 and/or external data server computer 66108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 66102 interacts with agricultural intelligence computer system 66130 using field manager computing device 66104 configured with an operating system and one or more application programs or apps; the field manager computing device 66104 also may interoperate with the agricultural intelligence computer system independently and automatically under program control or logical control and direct user interaction is not always required. Field manager computing device 66104 broadly represents one or more of a smart phone, PDA, tablet computing device, laptop computer, desktop computer, workstation, or any other computing device capable of transmitting and receiving information and performing the functions described herein. Field manager computing device 66104 may communicate via a network using a mobile application stored on field manager computing device 66104, and in some embodiments, the device may be coupled using a cable 66113 or connector to the sensor 66112 and/or controller 66114. A particular user 66102 may own, operate or possess and use, in connection with system 66130, more than one field manager computing device 66104 at a time.

The mobile application may provide client-side functionality, via the network to one or more mobile computing devices. In an example embodiment, field manager computing device 66104 may access the mobile application via a web browser or a local client application or app. Field manager computing device 66104 may transmit data to, and receive data from, one or more front-end servers, using web-based protocols or formats such as HTTP, XML and/or JSON, or app-specific protocols. In an example embodiment, the data may take the form of requests and user information input, such as field data, into the mobile computing device. In some embodiments, the mobile application interacts with location tracking hardware and software on field manager computing device 66104 which determines the location of field manager computing device 66104 using standard tracking techniques such as multilateration of radio signals, the global positioning system (GPS), Wi-Fi positioning systems, or other methods of mobile positioning. In some cases, location data or other data associated with the device 66104, user 66102, and/or user account(s) may be obtained by queries to an operating system of the device or by requesting an app on the device to obtain data from the operating system.

In an embodiment, field manager computing device 66104 sends field data 66106 to agricultural intelligence computer system 66130 comprising or including, but not limited to, data values representing one or more of: a geographical location of the one or more fields, tillage information for the one or more fields, crops planted in the one or more fields, and soil data extracted from the one or more fields. Field manager computing device 66104 may send field data 66106 in response to user input from user 66102 specifying the data values for the one or more fields. Additionally, field manager computing device 66104 may automatically send field data 66106 when one or more of the data values becomes available to field manager computing device 66104. For example, field manager computing device 66104 may be communicatively coupled to remote sensor 66112 and/or application controller 66114 which include an irrigation sensor and/or irrigation controller and/or agricultural implement controller. In response to receiving data indicating that application controller 66114 released water onto the one or more fields or, more generally, that application controller 66114 caused a machine (such as an agricultural implement) to operate in a certain way based on a control signal from application controller 66114, field manager computing device 66104 may send field data 66106 or other data to agricultural intelligence computer system 66130 indicating that water was released on the one or more fields or, more generally, data indicating that the computer-controlled machine operation has been completed. Field data 66106 identified in this disclosure may be input and communicated using electronic digital data that is communicated between computing devices using parameterized URLs over HTTP, or another suitable communication or messaging protocol.

A commercial example of a mobile application in which aspects of this disclosure may be implemented is CLIMATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

Figure 67A:
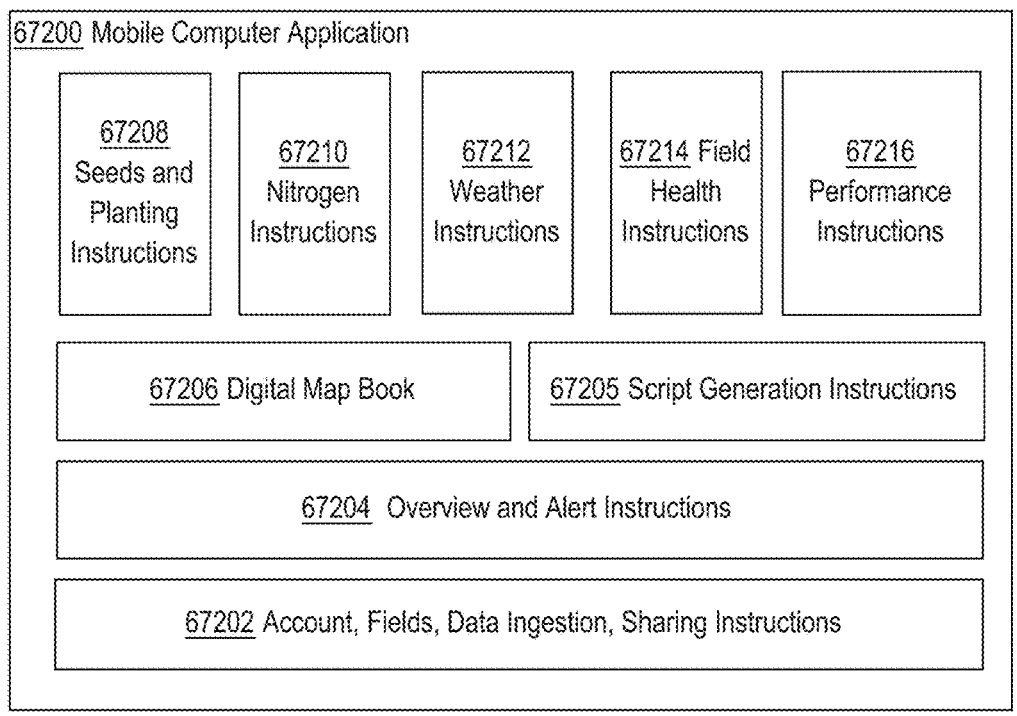
FIG. 67(a) and FIG. 67(b) illustrate two views of an example logical organization of sets of instructions in main memory when an example mobile application is loaded for execution.
Figure 67B:
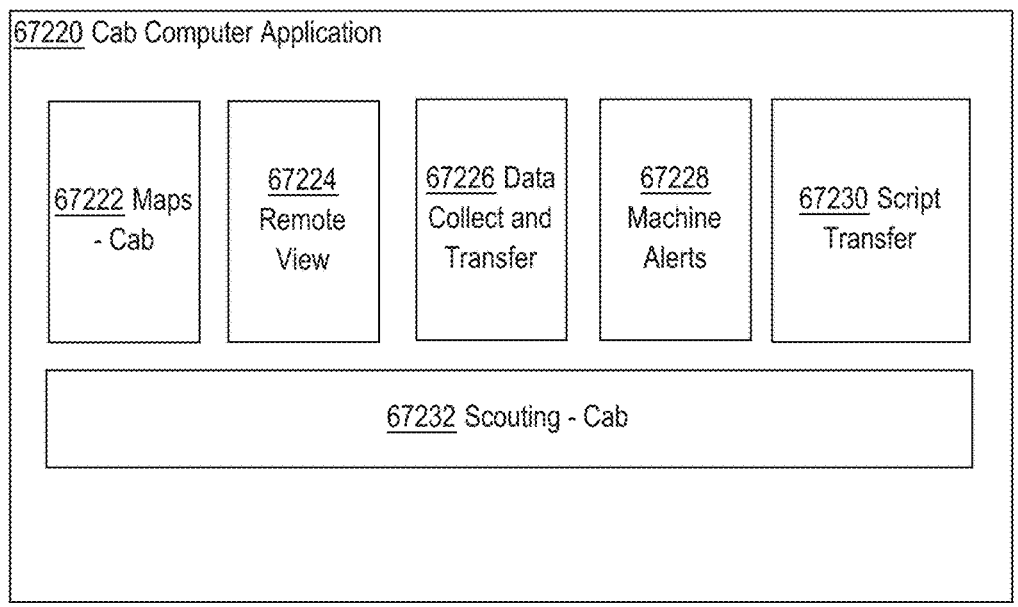

FIG. 67(a) and FIG. 67(b) illustrate two views of an example logical organization of sets of instructions in main memory when an example mobile application is loaded for execution. In FIG. 67(a) and FIG. 67(b), each named element represents a region of one or more pages of RAM or other main memory, or one or more blocks of disk storage or other non-volatile storage, and the programmed instructions within those regions. In one embodiment, in view 67(a), a mobile computer application 67200 comprises account-fields-data ingestion-sharing instructions 67202, overview and alert instructions 67204, digital map book instructions 67206, seeds and planting instructions 67208, nitrogen instructions 67210, weather instructions 67212, field health instructions 67214, and performance instructions 67216.

In one embodiment, a mobile computer application 67200 comprises account, fields, data ingestion, sharing instructions 67202 which are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, e-mail with attachment, external APIs that push data to the mobile application, or instructions that call APIs of external systems to pull data into the mobile application. In one embodiment, mobile computer application 67200 comprises a data inbox. In response to receiving a selection of the data inbox, the mobile computer application 67200 may display a graphical user interface for manually uploading data files and importing uploaded files to a data manager.

In one embodiment, digital map book instructions 67206 comprise field map data layers stored in device memory and are programmed with data visualization tools and geospatial field notes. This provides growers with convenient information close at hand for reference, logging and visual insights into field performance. In one embodiment, overview and alert instructions 67204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 67208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 67205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 67200 may display one or more fields broken into management zones, such as the field map data layers created as part of digital map book instructions 67206. In one embodiment, the management zones comprise soil zones along with a panel identifying each soil zone and a soil name, texture, drainage for each zone, or other field data. Mobile computer application 67200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 67200 may make the script available for download in a format readable by an application controller, such as an archived or compressed format. Additionally, and/or alternatively, a script may be sent directly to cab computer 66115 from mobile computer application 67200 and/or uploaded to one or more data servers and stored for further use.

In one embodiment, nitrogen instructions 67210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of fertilizer application zones and/or images generated from subfield soil data, such as data obtained from sensors, at a high spatial resolution (as fine as millimeters or smaller depending on sensor proximity and resolution); upload of existing grower-defined zones; providing a graph of plant nutrient availability and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields and/or zones that have been defined in the system; example data may include nitrogen application data that is the same for many fields and/or zones of the same grower, but such mass data entry applies to the entry of any type of field data into the mobile computer application 67200. For example, nitrogen instructions 67210 may be programmed to accept definitions of nitrogen application and practices programs and to accept user input specifying to apply those programs across multiple fields. "Nitrogen application programs," in this context, refers to stored, named sets of data that associates: a name, color code or other identifier, one or more dates of application, types of material or product for each of the dates and amounts, method of application or incorporation such as injected or broadcast, and/or amounts or rates of application for each of the dates, crop or hybrid that is the subject of the application, among others. "Nitrogen practices programs," in this context, refer to stored, named sets of data that associates: a practices name; a previous crop; a tillage system; a date of primarily tillage; one or more previous tillage systems that were used; one or more indicators of application type, such as manure, that were used. Nitrogen instructions 67210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field;

data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 67210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 67210 could be used for application of other nutrients (such as phosphorus and potassium), application of pesticide, and irrigation programs.

In one embodiment, weather instructions 67212 are programmed to provide field-specific recent weather data and forecasted weather information. This enables growers to save time and have an efficient integrated display with respect to daily operational decisions.

In one embodiment, field health instructions 67214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 67216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 67216 may be programmed to communicate via the network(s) 66109 to back-end analytics programs executed at agricultural intelligence computer system 66130 and/or external data server computer 66108 and configured to analyze metrics such as yield, yield differential, hybrid, population, SSURGO zone, soil test properties, or elevation, among others. Programmed reports and analysis may include yield variability analysis, treatment effect estimation, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 66115. For example, referring now to view (b) of FIG. 67(*a*) and FIG. 67(*b*), in one embodiment a cab computer application 67220 may comprise maps-cab instructions 67222, remote view instructions 67224, data collect and transfer instructions 67226, machine alerts instructions 67228, script transfer instructions 67230, and scouting-cab instructions 67232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 67222 may be programmed to provide map views of fields, farms or regions that are useful in directing machine operation. The remote view instructions 67224 may be programmed to turn on, manage, and provide views of machine activity in real-time or near real-time to other computing devices connected to the system 66130 via wireless networks, wired connectors or adapters, and the like. The data collect and transfer instructions 67226 may be programmed to turn on, manage, and provide transfer of data collected at sensors and controllers to the system 66130 via wireless networks, wired connectors or adapters, and the like. The machine alerts instructions 67228 may be programmed to detect issues with operations of the machine or tools that are associated with the cab and generate operator alerts. The script transfer instructions 67230 may be configured to transfer in scripts of instructions that are configured to direct machine operations or the collection of data. The scouting-cab instructions 67232 may be programmed to display location-based alerts and information received from the system 66130 based on the location of the field manager computing device 66104, agricultural apparatus 66111, or sensors 66112 in the field and ingest, manage, and provide transfer of location-based scouting observations to the system 66130 based on the location of the agricultural apparatus 66111 or sensors 66112 in the field.

2.3. Data Ingest to the Computer System

In an embodiment, external data server computer 66108 stores external data 66110, including soil data representing soil composition for the one or more fields and weather data representing temperature and precipitation on the one or more fields. The weather data may include past and present weather data as well as forecasts for future weather data. In an embodiment, external data server computer 66108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 66112 comprises one or more sensors that are programmed or configured to produce one or more observations. Remote sensor 66112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 66114 is programmed or configured to receive instructions from agricultural intelligence computer system 66130. Application controller 66114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 66130 may obtain or ingest data under user 66102 control, on a mass basis from a large number of growers who have contributed data to a shared database system. This form of obtaining data may be termed "manual data ingest" as one or more user-controlled computer operations are requested or triggered to obtain data for use by the system 66130. As an example, the CLIMATE FIELDVIEW application, commercially available from The Climate Corporation, San Francisco, Calif., may be operated to export data to system 66130 for storing in the repository 66160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 66115 or other devices within the system 66130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 66115 or other devices within the system 66130. Yield monitor systems may utilize one or more remote sensors 66112 to obtain grain moisture measurements in a combine or other harvester and transmit these measurements to the user via the cab computer 66115 or other devices within the system 66130.

In an embodiment, examples of sensors 66112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or Wi-Fi-based position or mapping apps that are programmed to determine location based upon nearby Wi-Fi hotspots, among others.

In an embodiment, examples of sensors 66112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 66114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 66112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 66114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 66112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 66114 that may be used with tillage equipment include downforce controllers or tool position controllers, such as controllers configured to control tool depth, gang angle, or lateral spacing.

In an embodiment, examples of sensors 66112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 66114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 66112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 66114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 66112 that may be used with grain carts include weight sensors, or sensors for auger position, operation, or speed. In an embodiment, examples of controllers 66114 that may be used with grain carts include controllers for auger position, operation, or speed.

In an embodiment, examples of sensors 66112 and controllers 66114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus; other electromagnetic radiation emitters and reflected electromagnetic radiation detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 66112 and controllers 66114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

In an embodiment, sensors 66112 and controllers 66114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4. Process Overview-Agronomic Model Training

In an embodiment, the agricultural intelligence computer system 66130 is programmed or configured to create an agronomic model. In this context, an agronomic model is a data structure in memory of the agricultural intelligence computer system 66130 that comprises field data 66106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, fertilizer recommendations, fungicide recommendations, pesticide recommendations, harvesting recommendations and other crop management recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 66130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 68:
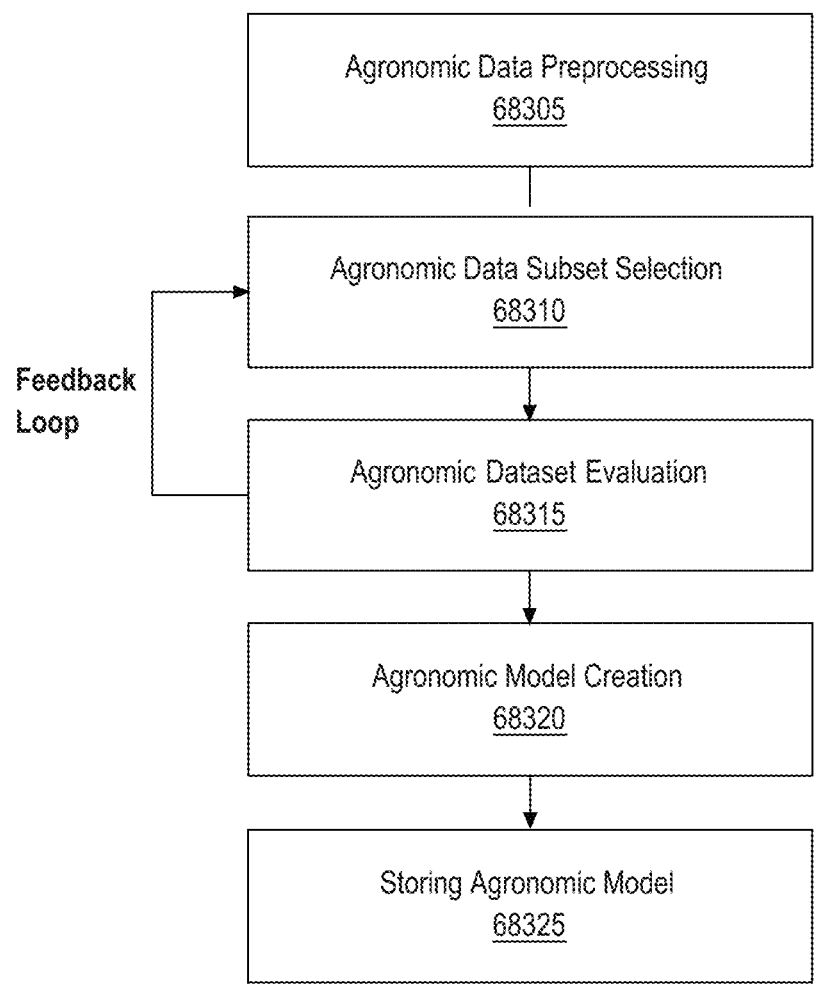
FIG. 68 illustrates a programmed process by which the agricultural intelligence computer system generates one or more preconfigured agronomic models using agronomic data provided by one or more data sources.

FIG. 68 illustrates a programmed process by which the agricultural intelligence computer system generates one or more preconfigured agronomic models using field data provided by one or more data sources. FIG. 68 may serve as an algorithm or instructions for programming the functional elements of the agricultural intelligence computer system 66130 to perform the operations that are now described.

At block 68305, the agricultural intelligence computer system 66130 is configured or programmed to implement agronomic data preprocessing of field data received from one or more data sources. The field data received from one or more data sources may be preprocessed for the purpose of removing noise, distorting effects, and confounding factors within the agronomic data including measured outliers that could adversely affect received field data values. Embodiments of agronomic data preprocessing may include, but are not limited to, removing data values commonly associated with outlier data values, specific measured data points that are known to unnecessarily skew other data values, data smoothing, aggregation, or sampling techniques used to remove or reduce additive or multiplicative effects from noise, and other filtering or data derivation techniques used to provide clear distinctions between positive and negative data inputs.

At block 68310, the agricultural intelligence computer system 66130 is configured or programmed to perform data subset selection using the preprocessed field data in order to identify datasets useful for initial agronomic model generation. The agricultural intelligence computer system 66130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 68315, the agricultural intelligence computer system 66130 is configured or programmed to implement field dataset evaluation. In an embodiment, a specific field dataset is evaluated by creating an agronomic model and using specific quality thresholds for the created agronomic model. Agronomic models may be compared and/or validated using one or more comparison techniques, such as, but not limited to, root mean square error with leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 68310).

At block 68320, the agricultural intelligence computer system 66130 is configured or programmed to implement agronomic model creation based upon the cross validated agronomic datasets. In an embodiment, agronomic model creation may implement multivariate regression techniques to create preconfigured agronomic data models.

At block 68325, the agricultural intelligence computer system 66130 is configured or programmed to store the preconfigured agronomic data models for future field data evaluation.

2.5. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 69 is a block diagram that illustrates a computer system 69400 upon which an embodiment of the invention may be implemented. Computer system 69400 includes a bus 69402 or other communication mechanism for communicating information, and a hardware processor 69404 coupled with bus 69402 for processing information. Hardware processor 69404 may be, for example, a general purpose microprocessor.

Computer system 69400 also includes a main memory 69406, such as a random access memory (RAM) or other dynamic storage device, coupled to bus 69402 for storing information and instructions to be executed by processor 69404. Main memory 69406 also may be used for storing temporary variables or other intermediate information during execution of instructions to be executed by processor 69404. Such instructions, when stored in non-transitory storage media accessible to processor 69404, render computer system 69400 into a special-purpose machine that is customized to perform the operations specified in the instructions.

Computer system 69400 further includes a read only memory (ROM) 408 or other static storage device coupled to bus 69402 for storing static information and instructions for processor 69404. A storage device 69410, such as a magnetic disk, optical disk, or solid-state drive is provided and coupled to bus 69402 for storing information and instructions.

Computer system 69400 may be coupled via bus 69402 to a display 69412, such as a cathode ray tube (CRT), for displaying information to a computer user. An input device 69414, including alphanumeric and other keys, is coupled to bus 69402 for communicating information and command selections to processor 69404. Another type of user input device is cursor control 69416, such as a mouse, a trackball, or cursor direction keys for communicating direction information and command selections to processor 69404 and for controlling cursor movement on display 69412. This input device typically has two degrees of freedom in two axes, a first axis (e.g., x) and a second axis (e.g., y), that allows the device to specify positions in a plane.

Computer system 69400 may implement the techniques described herein using customized hard-wired logic, one or more ASICs or FPGAs, firmware and/or program logic which in combination with the computer system causes or programs computer system 69400 to be a special-purpose machine. According to one embodiment, the techniques herein are performed by computer system 69400 in response to processor 69404 executing one or more sequences of one or more instructions contained in main memory 69406. Such instructions may be read into main memory 69406 from another storage medium, such as storage device 69410. Execution of the sequences of instructions contained in main memory 69406 causes processor 69404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 69410. Volatile media includes dynamic memory, such as main memory 69406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 69402. Transmission media can also take the form of acoustic or light waves, such as those generated during radio-wave and infrared data communications.

Various forms of media may be involved in carrying one or more sequences of one or more instructions to processor 69404 for execution. For example, the instructions may initially be carried on a magnetic disk or solid-state drive of a remote computer. The remote computer can load the instructions into its dynamic memory and send the instructions over a telephone line using a modem. A modem local to computer system 69400 can receive the data on the telephone line and use an infra-red transmitter to convert the data to an infra-red signal. An infra-red detector can receive the data carried in the infrared signal and appropriate circuitry can place the data on bus 69402. Bus 69402 carries the data to main memory 69406, from which processor 69404 retrieves and executes the instructions. The instructions received by main memory 69406 may optionally be stored on storage device 69410 either before or after execution by processor 69404.

Computer system 69400 also includes a communication interface 69418 coupled to bus 69402. Communication interface 69418 provides a two-way data communication coupling to a network link 69420 that is connected to a local network 69422. For example, communication interface 69418 may be an integrated services digital network (ISDN) card, cable modem, satellite modem, or a modem to provide a data communication connection to a corresponding type of telephone line. As another example, communication interface 69418 may be a local area network (LAN) card to provide a data communication connection to a compatible LAN. Wireless links may also be implemented. In any such implementation, communication interface 69418 sends and receives electrical, electromagnetic or optical signals that carry digital data streams representing various types of information.

Network link 69420 typically provides data communication through one or more networks to other data devices. For example, network link 69420 may provide a connection through local network 69422 to a host computer 69424 or to data equipment operated by an Internet Service Provider (ISP) 426. ISP 69426 in turn provides data communication services through the world wide packet data communication network now commonly referred to as the "Internet" 69428. Local network 69422 and Internet 69428 both use electrical, electromagnetic or optical signals that carry digital data streams. The signals through the various networks and the signals on network link 69420 and through communication interface 69418, which carry the digital data to and from computer system 69400, are example forms of transmission media.

Computer system 69400 can send messages and receive data, including program code, through the network(s), network link 69420 and communication interface 69418. In the Internet example, a server 430 might transmit a requested code for an application program through Internet 69428, ISP 69426, local network 69422 and communication interface 69418.

The received code may be executed by processor 69404 as it is received, and/or stored in storage device 69410, or other non-volatile storage for later execution.

ADDITIONAL EXAMPLES

Illustrative examples of the technologies disclosed herein are provided below. An embodiment of the technologies may include any at least one, and any combination of, the examples described below.

In an example 1, a computer system includes one or more processors in data communication with one or more sensors that are coupled to an agricultural machine configured to interact with soil; one or more non-transitory computer-readable storage media storing sequences of program instructions which, when executed by the one or more processors, cause the one or more processors to, by electronic communication with the one or more sensors, determine measurement data relating to one or more of a temperature characteristic of the soil or a moisture characteristic of the soil or a conductivity characteristic of the soil or a reflectivity characteristic of the soil, based on the measurement data, generate a signal to cause the agricultural machine to control a position of an implement coupled to the agricultural machine to adjust a depth of a trench formed in the soil by the implement during operation of the agricultural machine.

An example 2 includes the subject matter of example 1, and includes instructions which when executed by the one or more processors, cause the system to determine measurement data comprising one or more of soil moisture data or soil organic matter data or soil porosity data or soil texture data or soil type data; based on the measurement data, generate a signal to cause the agricultural machine to control a seed meter to change a population of seeds planted in the soil.

An example 3 includes the subject matter of example 1, and includes instructions which when executed by the one or more processors, cause the system to determine measurement data comprising one or more of soil moisture data or soil organic matter data or soil porosity data or soil texture data or soil type data; based on the measurement data, generate a signal to cause the agricultural machine to change a seed variety of seeds planted in the soil.

An example 4 includes the subject matter of example 1, and includes instructions which when executed by the one or more processors, cause the system to determine measurement data comprising one or more of soil moisture data or soil organic matter data or soil porosity data or soil texture data or soil type data; based on the measurement data, generate a signal to cause the agricultural machine to adjust a rate of application of one or more of a fertilizer or a fungicide or an insecticide by the agricultural machine.

An example 5 includes the subject matter of example 1, and includes instructions which when executed by the one or more processors, cause the system to determine measurement data comprising one or more of soil moisture data or soil organic matter data or soil porosity data or soil texture data or soil type data; based on the measurement data, generate a signal to cause the agricultural machine to adjust a force applied to the soil by the implement.

An example 6 includes the subject matter of example 1, and includes instructions which when executed by the one or more processors, cause the system to: determine measurement data comprising furrow residue data; based on the measurement data, generate a signal to cause the agricultural machine to adjust a force applied in relation to the soil by a row cleaner of the implement.

An example 7 includes the subject matter of example 1, and includes instructions which when executed by the one or more processors, cause the system to display, in one or more windows of a monitor coupled to the implement, a representation of the measurement data, wherein the one or more windows includes: a soil moisture window to display estimated soil moisture data; or a soil temperature window to display estimated soil temperature data; or a depth setting window to display a depth at which the one or more sensors are sensing the measurement data; or a reflectivity variation window to display reflectivity data comprising a statistical reflectivity variation in a signal generated by a reflectivity sensor of the one or more sensors; or a carbon content window to display estimated soil carbon content data; or an organic matter window to display estimated soil organic matter content data; or a soil components window to display estimated fractional presence data relating to one or more soil components.

An example 8 includes the subject matter of example 1, and includes instructions which when executed by the one or more processors, cause the system to display, in a monitor coupled to the implement, a predicted agronomic result based on reflectivity data comprising a statistical reflectivity variation in a signal generated by a reflectivity sensor of the one or more sensors.

An example 9 includes the subject matter of example 1, and includes instructions which when executed by the one or more processors, cause the system to display, in a monitor coupled to a plurality of row units of the implement, one or more of: an average value of the measurement data for all of the plurality of row units; a highest value of the measurement data for all of the plurality of row units; a lowest value of the measurement data for all of the plurality of row units; individual values of the measurement data for each of the row units in the plurality of row units.

An example 10 includes the subject matter of example 1, and includes instructions which when executed by the one or more processors, cause the system to: display, in one or more windows of a monitor coupled to the implement, a representation of data, wherein the data includes one or more of soil data, the measurement data, or estimated data, the data relates to one or more of soil carbon content or soil electrical conductivity or soil organic matter or soil components or soil moisture or soil temperature, and the one or more windows includes: a map window to display a subset of the data, wherein the subset of the data corresponds to a numerical range of reflectivity variation associated with a threshold level of predicted emergence failure.

An example 11 includes the subject matter of example 1, and includes instructions which when executed by the one or more processors, cause the system to: display, in one or more windows of a monitor coupled to the implement, a representation of planting data, wherein the planting data is measured by the one or more sensors, the one or more sensors include one or more of an optical seed sensor or an electromagnetic seed sensor or a reflectivity sensor, and the one or more windows includes: one or more planting data windows to display one or more good spacing data values, wherein the one or more good spacing data values are calculated by the one or more processors based on seed pulses obtained from the one or more sensors.

An example 12 includes the subject matter of example 1, and includes instructions which when executed by the one or more processors, cause a monitor to receive weather data and soil data from one or more servers over a network, transmit the measurement data to the one or more servers using the network, and receive agronomic recommendation data from a recommendation system on the one or more servers.

An example 13 includes the subject matter of example 1, and includes instructions which when executed by the one or more processors, cause a depth adjustment actuator of the agricultural machine to cooperate with a trench opening system of the agricultural machine to adjust the depth of the trench.

An example 14 includes the subject matter of example 13, and includes instructions which when executed by the one or more processors, cause the depth adjustment actuator to modify a height of a gauge wheel of the trench opening system relative to an opener disc of the trench opening system to adjust the depth of the trench.

An example 15 includes the subject matter of example 1, and includes instructions which when executed by the one or more processors, cause a seed meter coupled to a hopper of the agricultural machine to control a rate of deposit of seeds from the hopper into the soil.

An example 16 includes the subject matter of example 15, and includes instructions which when executed by the one or more processors, cause a monitor in data communication with the one or more sensors and one or more clutches of the agricultural machine to cause the one or more clutches to selectively couple the seed meter to an electric drive.

An example 17 includes the subject matter of example 1, and includes instructions which when executed by the one or more processors, cause a monitor to receive, from one or more temperature sensors mounted to the agricultural implement, a signal relating to a temperature of the soil and determine the measurement data based on the temperature signal.

An example 18 includes the subject matter of example 1, and includes instructions which when executed by the one or more processors, cause a monitor to receive, from one or more reflectivity sensors mounted to the agricultural machine, a reflectivity signal relating to a reflectivity of the soil and determine the measurement data based on the reflectivity signal.

An example 19 includes the subject matter of example 18, and includes instructions which when executed by the one or more processors, cause the system to identify a first portion of the reflectivity signal as a seed pulse; identify a second portion of the signal as a measurement of a soil characteristic.

An example 20 includes the subject matter of example 18, and includes instructions which when executed by the one or more processors, cause the system to identify a wavelength of the reflectivity signal that is associated with a characteristic of a seed; obtain reflectivity measurement data at the wavelength.

An example 21 includes the subject matter of example 18, and includes instructions which when executed by the one or more processors, cause the system to, using the reflectivity signal, determine a seed pulse; based on the seed pulse, cause adjusting a timing of a deposit of an input into the trench by the implement during operation of the agricultural machine.

An example 22 includes the subject matter of example 18, and includes instructions which when executed by the one or more processors, cause the system to: using the reflectivity signal, identify a presence of crop residue in the trench; based on the identified presence of crop residue, cause adjusting of one or more of a valve or an actuator of the implement during operation of the agricultural machine.

An example 23 includes the subject matter of example 22, and includes instructions which when executed by the one or more processors, cause the system to display on a monitor, based on the identified presence of crop residue, a map of spatial variation in crop residue.

An example 24 includes the subject matter of example 18, and includes instructions which when executed by the one or more processors, cause the system to, using the reflectivity signal, determine a seed pulse; based on the seed pulse, determine a geospatially-mapped orientation of a seed.

An example 25 includes the subject matter of example 18, and includes instructions which when executed by the one or more processors, cause the system to, using the reflectivity signal, determine seed-to-soil contact data; display a map of spatial variation in the seed-to-soil contact data on the monitor.

An example 26 includes the subject matter of example 18, and includes instructions which when executed by the one or more processors, cause a monitor to receive, from one or more electrical conductivity sensors, a signal relating to an electrical conductivity of the soil.

An example 27 includes the subject matter of example 1, and includes instructions which when executed by the one or more processors, cause the system to obtain seed pulse data from an optical seed sensor of the one or more sensors; modify the seed pulse data based on a signal generated by a reflectivity sensor of the one or more sensors.

An example 28 includes the subject matter of example 1, and includes instructions which when executed by the one or more processors, cause the system to, based on one or more signals relating to a measured reflectivity of the soil, the one or more signals received from a plurality of reflectivity sensors mounted to a seed firmer of the agricultural machine, determine the measurement data.

An example 29 includes the subject matter of example 1, and includes instructions which when executed by the one or more processors, cause the system to, based on one or more signals relating to a capacitance moisture of the soil, the one or more signals received from a capacitive moisture sensor mounted to a seed firmer of the agricultural machine, determine the measurement data.

An example 30 includes the subject matter of example 1, and includes instructions which when executed by the one or more processors, cause the system to, based on one or more signals relating to a soil moisture tension of the soil, the one or more signals received from an electronic tensiometer sensor mounted to a seed firmer of the agricultural machine, determine the measurement data.

An example 31 includes the subject matter of example 1, and includes instructions which when executed by the one or more processors cause using the measurement data obtained from the one or more sensors to compute a soil moisture tension of the soil.

An example 32 includes the subject matter of example 1, and includes instructions which when executed by the one or more processors, cause the system to, based on one or more signals relating to a temperature of the soil, the one or more signals received from a temperature sensor mounted to a seed firmer of the agricultural machine, determine the measurement data.

An example 33 includes the subject matter of example 1, and includes instructions which when executed by the one or more processors, cause the system to: obtain the measurement data by interfacing with a plurality of soil-engaging ears comprising a conductive material coupled to the implement.

An example includes the subject matter of example 1, and includes instructions which when executed by the one or more processors, cause the system to adjust, based on a measured temperature of the soil, one or more of soil reflectivity measurement data or soil electrical conductivity measurement data.

An example 35 includes the subject matter of example 1, and includes a monitor in data communication with the one or more sensors to obtain the measurement data, the one or more sensors being mounted to a seed firmer of the agricultural machine, the one or more sensors comprising a plurality of reflectivity sensors and a plurality of temperature sensors and a plurality of electrical conductivity sensors.

An example 36 includes the subject matter of example 1, and includes instructions which when executed by the one or more processors, cause the system to: based on reflectivity measurement data obtained from a reflectivity sensor of the one or more sensors, calculate a seed germination moisture value, cause adjusting the depth of the trench formed in the soil by the implement during operation of the agricultural machine based on the seed germination moisture value.

An example 37 includes the subject matter of example 1, and includes instructions which when executed by the one or more processors, cause the system to: calculate a uniformity of moisture value based on the measurement data obtained from the one or more sensors, cause adjusting the depth of the trench formed in the soil by the implement during operation of the agricultural machine based on the uniformity of moisture value.

An example 38 includes the subject matter of example 1, and includes instructions which when executed by the one or more processors, cause the system to: calculate an emergence environment score based on the measurement data obtained from the one or more sensors, cause adjusting the depth of the trench formed in the soil by the implement during operation of the agricultural machine based on the emergence environment score.

An example 39 includes the subject matter of example 1, and includes instructions which when executed by the one or more processors, cause the system to: calculate a moisture variability value based on the measurement data obtained from the one or more sensors, cause adjusting the depth of the trench formed in the soil by the implement during operation of the agricultural machine based on the moisture variability.

An example 40 includes the subject matter of example 1, and includes instructions which when executed by the one or more processors, cause the system to remove measurement of ambient light from a total light measurement measured from a reflectivity sensor of the one or more sensors, by: emitting light from an emitter of the reflectivity sensor; measuring the total light measurement; turning off the emitter; measuring ambient light; calculating reflected light by subtracting the ambient light measurement from the total light measurement.

An example 41 includes the subject matter of example 1, and includes instructions which when executed by the one or more processors, cause the system to analyze voids in soil by: causing moving a reflectivity sensor through soil; measuring reflectivity received at first and second detectors of the reflectivity sensor; obtaining speed of the reflectivity sensor through the soil; calculating at least one of void length, void depth, and number of voids per linear distance from a first detector reflectivity measurement and a second detector reflectivity measurement.

In an example 42, a computer-implemented method includes using one or more processors in data communication with one or more sensors that are coupled to an agricultural machine configured to interact with soil, by electronic communication with the one or more sensors, determining measurement data relating to one or more of a temperature characteristic of the soil or a moisture characteristic of the soil or a conductivity characteristic of the soil or a reflectivity characteristic of the soil; based on the measurement data, generating a signal to cause the agricultural machine to control a position of an implement coupled to the agricultural machine to adjust a depth of a trench formed in the soil by the implement during operation of the agricultural machine.

An example 43 includes the subject matter of example 42, and includes determining measurement data comprising one or more of soil moisture data or soil organic matter data or soil porosity data or soil texture data or soil type data; based on the measurement data, generating a signal to cause the agricultural machine to control a seed meter to change a population of seeds planted in the soil.

An example 44 An example 43 includes the subject matter of example 42, and includes determining measurement data comprising one or more of soil moisture data or soil organic matter data or soil porosity data or soil texture data or soil type data; based on the measurement data, generating a signal to cause the agricultural machine to change a seed variety of seeds planted in the soil.

An example 45 includes the subject matter of example 42, and includes determining measurement data comprising one or more of soil moisture data or soil organic matter data or soil porosity data or soil texture data or soil type data; based on the measurement data, generating a signal to cause the agricultural machine to adjust a rate of application of one or more of a fertilizer or a fungicide or an insecticide by the agricultural machine.

An example 46 includes the subject matter of example 42, and includes determining measurement data comprising one or more of soil moisture data or soil organic matter data or soil porosity data or soil texture data or soil type data; based on the measurement data, generating a signal to cause the agricultural machine to adjust a force applied to the soil by the implement.

An example 47 includes the subject matter of example 42, and includes determining measurement data comprising furrow residue data; based on the measurement data, generating a signal to cause the agricultural machine to adjust a force applied in relation to the soil by a row cleaner of the implement.

An example 48 includes the subject matter of example 42, and includes displaying, in one or more windows of a monitor coupled to the implement, a representation of the measurement data, the one or more windows including: a soil moisture window to display estimated soil moisture data; or a soil temperature window to display estimated soil temperature data; or a depth setting window to display a depth at which the one or more sensors are sensing the measurement data; or a reflectivity variation window to display reflectivity data comprising a statistical reflectivity variation in a signal generated by a reflectivity sensor of the one or more sensors; or a carbon content window to display estimated soil carbon content data; or an organic matter window to display estimated soil organic matter content data; or a soil components window to display estimated fractional presence data relating to one or more soil components.

An example 49 includes the subject matter of example 42, and includes displaying, in a monitor coupled to the implement, a predicted agronomic result based on reflectivity data comprising a statistical reflectivity variation in a signal generated by a reflectivity sensor of the one or more sensors.

An example 50 includes the subject matter of example 42, and includes displaying, in a monitor coupled to a plurality of row units of the implement, one or more of: an average value of the measurement data for all of the plurality of row units; a highest value of the measurement data for all of the plurality of row units; a lowest value of the measurement data for all of the plurality of row units; individual values of the measurement data for each of the row units in the plurality of row units.

An example 51 includes the subject matter of example 42, and includes displaying, in one or more windows of a monitor coupled to the implement, a representation of data, wherein the data includes one or more of soil data, the measurement data, or estimated data, the data relates to one or more of soil carbon content or soil electrical conductivity or soil organic matter or soil components or soil moisture or soil temperature, and the one or more windows includes: a map window to display a subset of the data, wherein the subset of the data corresponds to a numerical range of reflectivity variation associated with a threshold level of predicted emergence failure.

An example 52 includes the subject matter of example 42, and includes displaying, in one or more windows of a monitor coupled to the implement, a representation of planting data, wherein the planting data is measured by the one or more sensors, the one or more sensors include one or more of an optical seed sensor or an electromagnetic seed sensor or a reflectivity sensor, and the one or more windows includes: one or more planting data windows to display one or more good spacing data values, wherein the one or more good spacing data values are calculated by the one or more processors based on seed pulses obtained from the one or more sensors.

An example 53 includes the subject matter of example 42, and includes causing a monitor to receive weather data and soil data from one or more servers over a network, transmit the measurement data to the one or more servers using the network, and receive agronomic recommendation data from a recommendation system on the one or more servers.

An example 54 includes the subject matter of example 42, and includes causing a depth adjustment actuator of the agricultural machine to cooperate with a trench opening system of the agricultural machine to adjust the depth of the trench.

An example 55 includes the subject matter of example 54, and includes causing the depth adjustment actuator to modify a height of a gauge wheel of the trench opening system relative to an opener disc of the trench opening system to adjust the depth of the trench.

An example 56 includes the subject matter of example 42, and includes causing a seed meter coupled to a hopper of the agricultural machine to control a rate of deposit of seeds from the hopper into the soil.

An example 57 includes the subject matter of example 56, and includes causing a monitor in data communication with the one or more sensors and one or more clutches of the agricultural machine to cause the one or more clutches to selectively couple the seed meter to an electric drive.

An example 58 includes the subject matter of example 42, and includes causing a monitor to receive, from one or more temperature sensors mounted to the agricultural implement, a signal relating to a temperature of the soil; obtaining the measurement data from the signal.

An example 59 includes the subject matter of example 42, and includes causing a monitor to receive, from one or more reflectivity sensors mounted to the agricultural machine, a reflectivity signal relating to a reflectivity of the soil; obtaining the measurement data from the signal.

An example 60 includes the subject matter of example 59, and includes identifying a first portion of the reflectivity signal as a seed pulse; identifying a second portion of the signal as a measurement of a soil characteristic.

An example 61 includes the subject matter of example 59, and includes identifying a wavelength of the reflectivity signal that is associated with a characteristic of a seed; obtaining reflectivity measurement data at the wavelength.

An example 62 includes the subject matter of example 59, and includes using the reflectivity signal, determining a seed pulse; based on the seed pulse, causing adjusting a timing of a deposit of an input into the trench by the implement during operation of the agricultural machine.

An example 63 includes the subject matter of example 59, and includes using the reflectivity signal, identifying a presence of crop residue in the trench; based on the identified presence of crop residue, causing adjusting of one or more of a valve or an actuator of the implement during operation of the agricultural machine.

An example 64 includes the subject matter of example 63, and includes displaying on a monitor, based on the identified presence of crop residue, a map of spatial variation in crop residue.

An example 65 includes the subject matter of example 59, and includes, using the reflectivity signal, determining a seed pulse; based on the seed pulse, determining a geospatially-mapped orientation of a seed.

An example 66 includes the subject matter of example 59, and includes, using the reflectivity signal, determining seed-to-soil contact data; displaying a map of spatial variation in the seed-to-soil contact data on the monitor.

An example 67 includes the subject matter of example 42, and includes receiving, from one or more electrical conductivity sensors, a signal relating to an electrical conductivity of the soil; obtaining the measurement data from the signal.

An example 68 includes the subject matter of example 42, and includes obtaining seed pulse data from an optical seed sensor of the one or more sensors; modifying the seed pulse data based on a signal generated by a reflectivity sensor of the one or more sensors.

An example 69 includes the subject matter of example 42, and includes, based on one or more signals from a plurality of reflectivity sensors mounted to a seed firmer of the agricultural machine, measuring a reflectivity of the soil.

An example 70 includes the subject matter of example 42, and includes, based on one or more signals from a capacitive moisture sensor mounted to a seed firmer of the agricultural machine, measuring a capacitance moisture of the soil.

An example 71 includes the subject matter of example 42, and includes, based on one or more signals from an electronic tensiometer sensor mounted to a seed firmer of the agricultural machine, measuring a soil moisture tension of the soil.

An example 72 includes the subject matter of example 42, and includes using the measurement data obtained from the one or more sensors to determine a soil moisture tension of the soil.

An example 73 includes the subject matter of example 42, and includes, based on one or more signals from a temperature sensor mounted to a seed firmer of the agricultural machine, measuring a temperature of the soil.

An example 74 includes the subject matter of example 42, and includes obtaining the measurement data by interfacing with a plurality of soil-engaging ears comprising a conductive material coupled to the implement.

An example 75 includes the subject matter of example 42, and includes, based on a measured temperature of the soil, adjusting one or more of soil reflectivity measurement data or soil electrical conductivity measurement data.

An example 76. includes the subject matter of example 42, and includes obtaining the measurement data from one or more sensors mounted to a seed firmer of the agricultural machine, the one or more sensors comprising a plurality of reflectivity sensors and a plurality of temperature sensors and a plurality of electrical conductivity sensors.

An example 77 includes the subject matter of example 42, and includes, based on reflectivity measurement data obtained from a reflectivity sensor of the one or more sensors, calculating a seed germination moisture value; causing adjusting the depth of the trench formed in the soil by the implement during operation of the agricultural machine based on the seed germination moisture value.

An example 78 includes the subject matter of example 42, and includes calculating a uniformity of moisture value based on the measurement data obtained from the one or more sensors; causing adjusting the depth of the trench formed in the soil by the implement during operation of the agricultural machine based on the uniformity of moisture value.

An example includes the subject matter of example 42, and includes calculating an emergence environment score based on the measurement data obtained from the one or more sensors; causing adjusting the depth of the trench formed in the soil by the implement during operation of the agricultural machine based on the emergence environment score.

An example 80 includes the subject matter of example 42, and includes calculating a moisture variability value based on the measurement data obtained from the one or more sensors; causing adjusting the depth of the trench formed in the soil by the implement during operation of the agricultural machine based on the moisture variability.

An example 81 includes the subject matter of example 42, and includes removing measurement of ambient light from a total light measurement measured from a reflectivity sensor of the one or more sensors, by: emitting light from an emitter of the reflectivity sensor; measuring the total light measurement; turning off the emitter; measuring ambient light; calculating reflected light by subtracting the ambient light measurement from the total light measurement.

An example 82 includes the subject matter of example 42, and includes analyzing voids in the soil by: causing moving a reflectivity sensor through the soil; measuring reflectivity received at first and second detectors of the reflectivity sensor; obtaining speed of the reflectivity sensor through the soil; calculating at least one of void length, void depth, and number of voids per linear distance from a first detector reflectivity measurement and a second detector reflectivity measurement.

In an example 83, a soil testing implement includes a base; a resilient portion connected to the base and adapted for connection to an agricultural implement; a protrusion on the base; and a sensor disposed in the base and disposed to sense soil through the protrusion.

In an example 84, a soil testing implement includes a base; a resilient portion connected to the base and adapted for connection to an agricultural implement; a reflectivity sensor disposed in the base and disposed to sense soil through an opening in the base; and a prism disposed between the reflectivity sensor and the opening in the base.

An example 85 includes the soil testing implement of example 84, wherein the prism has sides that are angled to correspond to a critical angle of material of the prism.

In an example 86, a soil testing implement includes a base; a resilient portion connected to the base and adapted for connection to an agricultural implement; and a reflectivity sensor disposed in the base and disposed to sense soil through an opening in the base, wherein the reflectivity sensor includes at least one emitter and a first detector and a second detector, wherein the at least one emitter and the first detector are in line and directed in a same direction, the second detector is offset from the at least one emitter and the first detector, the second detector is directed towards the at least one emitter and the first detector and disposed at an angle from a perpendicular to the direction of the at least one emitter and the first detector.

In an example 87, a method of removing measurement of ambient light from a total light measurement measured from a reflectivity sensor, wherein the reflectivity sensor includes an emitter and a detector, where the method includes emitting light from the emitter; measuring the total light measurement; turning off the emitter; measuring ambient light; calculating reflected light by subtracting the ambient light measurement from the total light measurement.

In an example 88, a method of analyzing voids in soil includes moving a reflectivity sensor through soil, wherein the reflectivity sensor includes at least one emitter and a first detector and a second detector, wherein the at least one emitter and the first detector are in line and directed in a same direction, the second detector is offset from the at least one emitter and the first detector, the second detector is directed towards the at least one emitter and the first detector and disposed at an angle from a perpendicular to the direction of the at least one emitter and the first detector; measuring reflectivity received at the first detector and the second detector; obtaining speed of the reflectivity sensor through soil; calculating at least one of void length, void depth, and number of voids per linear distance from the first detector reflectivity measurement and the second detector reflectivity measurement.

In an example 89, a temperature sensor includes a body; a window disposed through the body that allows at least 50% of infrared radiation to pass through the window; a thermopile disposed in the body to have a field of view through the window. An example 90 includes the temperature sensor of example 89, wherein the field of view is 70° to 180°.

General Considerations

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Any definitions set forth herein for terms contained in the claims may govern the meaning of such terms as used in the claims. No limitation, element, property, feature, advantage or attribute that is not expressly recited in a claim should limit the scope of the claim in any way. The specification and drawings are to be regarded in an illustrative rather than a restrictive sense.

As used herein the terms "include" and "comprise" (and variations of those terms, such as "including," "includes," "comprising," "comprises," "comprised" and the like) are intended to be inclusive and are not intended to exclude further features, components, integers or steps.

References in this document to "an embodiment," etc., indicate that the embodiment described or illustrated may include a particular feature, structure, or characteristic, but every embodiment may not necessarily include the particular feature, structure, or characteristic. Such phrases are not necessarily referring to the same embodiment. Further, when a particular feature, structure, or characteristic is described or illustrated in connection with an embodiment, it is believed to be within the knowledge of one skilled in the art to effect such feature, structure, or characteristic in connection with other embodiments whether or not explicitly indicated.

Various features of the disclosure have been described using process steps. The functionality/processing of a given process step could potentially be performed in different ways and by different systems or system modules. Furthermore, a given process step could be divided into multiple steps and/or multiple steps could be combined into a single step. Furthermore, the order of the steps can be changed without departing from the scope of the present disclosure.

It will be understood that the embodiments disclosed and defined in this specification extend to alternative combinations of the individual features and components mentioned or evident from the text or drawings. These different combinations constitute various alternative aspects of the embodiments.

What is claimed is:

1. A computer system comprising:
one or more processors in data communication with a wireless receiver in communication with one or more wireless transmitters each comprising a first coupler and a second coupler coupled to one or more sensors; the first coupler coupled to a body of an agricultural machine configured to interact with soil and the second coupler coupled to a removable portion of the agricultural machine; the first and second couplers arranged to engage electrically as the removable portion is mounted to the body of the agricultural machine;
one or more non-transitory computer-readable storage media coupled to the one or more processors and storing sequences of program instructions which, when executed by the one or more processors, cause the one or more processors to:
by data communication between the wireless receiver and the one or more wireless transmitters coupled to the one or more sensors, determine measurement data relating to one or more of a temperature characteristic of the soil or a moisture characteristic of the soil or a conductivity characteristic of the soil or a reflectivity characteristic of the soil;
based on the measurement data, generate and transmit a signal to the agricultural machine to cause the agricultural machine to control a position of an implement coupled to the agricultural machine to adjust a depth of a trench formed in the soil by the implement during operation of the agricultural machine.

2. The system of claim 1, the storage media further comprising instructions which when executed by the one or more processors, cause the system to determine measurement data comprising one or more of soil moisture data or soil organic matter data or soil porosity data or soil texture data or soil type data; based on the measurement data, generate a signal to cause the agricultural machine to control a seed meter to change a population of seeds planted in the soil.

3. The system of claim 1, the storage media further comprising instructions which when executed by the one or more processors, cause the system to determine measurement data comprising one or more of soil moisture data or soil organic matter data or soil porosity data or soil texture data or soil type data; based on the measurement data, generate a signal to cause the agricultural machine to change a seed variety of seeds planted in the soil.

4. The system of claim 1, the storage media further comprising instructions which when executed by the one or more processors, cause the system to determine measurement data comprising one or more of soil moisture data or soil organic matter data or soil porosity data or soil texture data or soil type data; based on the measurement data, generate a signal to cause the agricultural machine to adjust a rate of application of one or more of a fertilizer or a fungicide or an insecticide by the agricultural machine.

5. The system of claim 1, the storage media further comprising instructions which when executed by the one or more processors, cause the system to determine measurement data comprising one or more of soil moisture data or soil organic matter data or soil porosity data or soil texture data or soil type data; based on the measurement data, generate a signal to cause the agricultural machine to adjust a force applied to the soil by the implement.

6. The system of claim 1, the storage media further comprising instructions which when executed by the one or more processors, cause the system to: determine measurement data comprising furrow residue data; based on the measurement data, generate a signal to cause the agricultural machine to adjust a force applied in relation to the soil by a row cleaner of the implement.

7. The system of claim 1, the storage media further comprising instructions which when executed by the one or more processors, cause the system to display, in one or more windows of a monitor coupled to the implement, a representation of the measurement data, wherein the one or more windows comprises:
 a soil moisture window to display estimated soil moisture data; or
 a soil temperature window to display estimated soil temperature data; or
 a depth setting window to display a depth at which the one or more sensors are sensing the measurement data; or
 a reflectivity variation window to display reflectivity data comprising a statistical reflectivity variation in a signal generated by a reflectivity sensor of the one or more sensors; or
 a carbon content window to display estimated soil carbon content data; or
 an organic matter window to display estimated soil organic matter content data; or
 a soil components window to display estimated fractional presence data relating to one or more soil components.

8. The system of claim 1, the storage media further comprising instructions which when executed by the one or more processors, cause the system to display, in a monitor coupled to the implement, a predicted agronomic result based on reflectivity data comprising a statistical reflectivity variation in a signal generated by a reflectivity sensor of the one or more sensors.

9. The system of claim 1, the storage media further comprising instructions which when executed by the one or more processors, cause the system to display, in a monitor coupled to a plurality of row units of the implement, one or more of:
 an average value of the measurement data for all of the plurality of row units;
 a highest value of the measurement data for all of the plurality of row units;
 a lowest value of the measurement data for all of the plurality of row units;
 individual values of the measurement data for each of the row units in the plurality of row units.

10. The system of claim 1, the storage media further comprising instructions which when executed by the one or more processors, cause the system to: display, in one or more windows of a monitor coupled to the implement, a representation of data, wherein the data comprises one or more of soil data, the measurement data, or estimated data, the data relates to one or more of soil carbon content or soil electrical conductivity or soil organic matter or soil components or soil moisture or soil temperature, and the one or more windows comprises:
 a map window to display a subset of the data, wherein the subset of the data corresponds to a numerical range of reflectivity variation associated with a threshold level of predicted emergence failure.

11. The system of claim 1, the storage media further comprising instructions which when executed by the one or more processors, cause the system to:
 display, in one or more windows of a monitor coupled to the implement, a representation of planting data, wherein the planting data is measured by the one or more sensors, the one or more sensors comprise one or more of an optical seed sensor or an electromagnetic seed sensor or a reflectivity sensor, and the one or more windows comprises:
 one or more planting data windows to display one or more good spacing data values, wherein the one or more good spacing data values are calculated by the one or more processors based on seed pulses obtained from the one or more sensors.

12. The system of claim 1, the storage media further comprising instructions which when executed by the one or more processors, cause a monitor to receive weather data and soil data from one or more servers over a network, transmit the measurement data to the one or more servers using the network, and receive agronomic recommendation data from a recommendation system on the one or more servers.

13. The system of claim 1, the storage media further comprising instructions which when executed by the one or more processors, cause a depth adjustment actuator of the agricultural machine to cooperate with a trench opening system of the agricultural machine to adjust the depth of the trench.

14. The system of claim 13, the storage media further comprising instructions which when executed by the one or more processors, cause the depth adjustment actuator to modify a height of a gauge wheel of the trench opening system relative to an opener disc of the trench opening system to adjust the depth of the trench.

15. The system of claim 1, the storage media further comprising instructions which when executed by the one or more processors, cause a seed meter coupled to a hopper of the agricultural machine to control a rate of deposit of seeds from the hopper into the soil.

16. The system of claim 15, the storage media further comprising instructions which when executed by the one or more processors, cause a monitor in data communication with the one or more sensors and one or more clutches of the agricultural machine to cause the one or more clutches to selectively couple the seed meter to an electric drive.

17. The system of claim 1, the storage media further comprising instructions which when executed by the one or more processors, cause a monitor to receive, from one or more temperature sensors mounted to the agricultural implement, a signal relating to a temperature of the soil and determine the measurement data based on the temperature signal.

18. The system of claim 1, the storage media further comprising instructions which when executed by the one or more processors, cause a monitor to receive, from one or more reflectivity sensors mounted to the agricultural machine, a reflectivity signal relating to a reflectivity of the soil and determine the measurement data based on the reflectivity signal.

19. The system of claim 18, the storage media further comprising instructions which when executed by the one or more processors, cause the system to identify a first portion of the reflectivity signal as a seed pulse; identify a second portion of the signal as a measurement of a soil characteristic.

20. The system of claim 18, the storage media further comprising instructions which when executed by the one or more processors, cause the system to identify a wavelength of the reflectivity signal that is associated with a characteristic of a seed; obtain reflectivity measurement data at the wavelength.

21. The system of claim 18, the storage media further comprising instructions which when executed by the one or more processors, cause the system to, using the reflectivity signal, determine a seed pulse; based on the seed pulse, cause adjusting a timing of a deposit of an input into the trench by the implement during operation of the agricultural machine.

22. The system of claim 18, the storage media further comprising instructions which when executed by the one or more processors, cause the system to: using the reflectivity signal, identify a presence of crop residue in the trench; based on the identified presence of crop residue, cause adjusting of one or more of a valve or an actuator of the implement during operation of the agricultural machine.

23. The system of claim 22, the storage media further comprising instructions which when executed by the one or more processors, cause the system to display on a monitor, based on the identified presence of crop residue, a map of spatial variation in crop residue.

24. The system of claim 18, the storage media further comprising instructions which when executed by the one or more processors, cause the system to, using the reflectivity signal, determine a seed pulse; based on the seed pulse, determine a geospatially-mapped orientation of a seed.

25. The system of claim 18, the storage media further comprising instructions which when executed by the one or more processors, cause the system to, using the reflectivity signal, determine seed-to-soil contact data; display a map of spatial variation in the seed-to-soil contact data on the monitor.

26. The system of claim 18, the storage media further comprising instructions which when executed by the one or more processors, cause a monitor to receive, from one or more electrical conductivity sensors, a signal relating to an electrical conductivity of the soil.

27. The system of claim 1, the storage media further comprising instructions which when executed by the one or more processors, cause the system to obtain seed pulse data from an optical seed sensor of the one or more sensors; modify the seed pulse data based on a signal generated by a reflectivity sensor of the one or more sensors.

28. The system of claim 1, the storage media further comprising instructions which when executed by the one or more processors, cause the system to, based on one or more signals relating to a measured reflectivity of the soil, the one or more signals received from a plurality of reflectivity sensors mounted to a seed firmer of the agricultural machine, determine the measurement data.

29. The system of claim 1, the storage media further comprising instructions which when executed by the one or more processors, cause the system to, based on one or more signals relating to a capacitance moisture of the soil, the one or more signals received from a capacitive moisture sensor mounted to a seed firmer of the agricultural machine, determine the measurement data.

30. The system of claim 1, the storage media further comprising instructions which when executed by the one or more processors, cause the system to, based on one or more signals relating to a soil moisture tension of the soil, the one or more signals received from an electronic tensiometer sensor mounted to a seed firmer of the agricultural machine, determine the measurement data.

31. The system of claim 1, the storage media further comprising instructions which when executed by the one or more processors cause using the measurement data obtained from the one or more sensors to compute a soil moisture tension of the soil.

32. The system of claim 1, the storage media further comprising instructions which when executed by the one or more processors, cause the system to, based on one or more signals relating to a temperature of the soil, the one or more signals received from a temperature sensor mounted to a seed firmer of the agricultural machine, determine the measurement data.

33. The system of claim 1, the storage media further comprising instructions which when executed by the one or more processors, cause the system to:
  obtain the measurement data by interfacing with a plurality of soil-engaging ears comprising a conductive material coupled to the implement.

34. The system of claim 1, the storage media further comprising instructions which when executed by the one or more processors, cause the system to adjust, based on a measured temperature of the soil, one or more of soil reflectivity measurement data or soil electrical conductivity measurement data.

35. The system of claim 1, further comprising a monitor in data communication with the one or more sensors to obtain the measurement data, the one or more sensors being mounted to a seed firmer of the agricultural machine, the one or more sensors comprising a plurality of reflectivity sensors and a plurality of temperature sensors and a plurality of electrical conductivity sensors.

36. The system of claim 1, the storage media further comprising instructions which when executed by the one or more processors, cause the system to:
  based on reflectivity measurement data obtained from a reflectivity sensor of the one or more sensors, calculate a seed germination moisture value;
  cause adjusting the depth of the trench formed in the soil by the implement during operation of the agricultural machine based on the seed germination moisture value.

37. The system of claim 1, the storage media further comprising instructions which when executed by the one or more processors, cause the system to:
  calculate a uniformity of moisture value based on the measurement data obtained from the one or more sensors;
  cause adjusting the depth of the trench formed in the soil by the implement during operation of the agricultural machine based on the uniformity of moisture value.

38. The system of claim 1, the storage media further comprising instructions which when executed by the one or more processors, cause the system to:
  calculate an emergence environment score based on the measurement data obtained from the one or more sensors;
  cause adjusting the depth of the trench formed in the soil by the implement during operation of the agricultural machine based on the emergence environment score.

39. The system of claim 1, the storage media further comprising instructions which when executed by the one or more processors, cause the system to:
calculate a moisture variability value based on the measurement data obtained from the one or more sensors;
cause adjusting the depth of the trench formed in the soil by the implement during operation of the agricultural machine based on the moisture variability.

40. The system of claim 1, the storage media further comprising instructions which when executed by the one or more processors, cause the system to remove measurement of ambient light from a total light measurement measured from a reflectivity sensor of the one or more sensors, by:
emitting light from an emitter of the reflectivity sensor;
measuring the total light measurement;
turning off the emitter;
measuring ambient light;
calculating reflected light by subtracting the ambient light measurement from the total light measurement.

41. The system of claim 1, the storage media further comprising instructions which when executed by the one or more processors, cause the system to analyze voids in soil by:
causing moving a reflectivity sensor through soil;
measuring reflectivity received at first and second detectors of the reflectivity sensor;
obtaining speed of the reflectivity sensor through the soil;
calculating at least one of void length, void depth, and number of voids per linear distance from a first detector reflectivity measurement and a second detector reflectivity measurement.

42. A computer-implemented method comprising:
using one or more processors in data communication with a wireless receiver in communication with one or more wireless transmitters each comprising a first coupler and a second coupler coupled to one or more sensors; the first coupler coupled to a body of an agricultural machine configured to interact with soil and the second coupler coupled to a removable portion of the agricultural machine; the first and second couplers arranged to engage electrically as the removable portion is mounted to the body of the agricultural machine, by data communication between the wireless receiver and the one or more wireless transmitters coupled to the one or more sensors, determining measurement data relating to one or more of a temperature characteristic of the soil or a moisture characteristic of the soil or a conductivity characteristic of the soil or a reflectivity characteristic of the soil;
based on the measurement data, generating and transmitting a signal to the agricultural machine to cause the agricultural machine to control a position of an implement coupled to the agricultural machine to adjust a depth of a trench formed in the soil by the implement during operation of the agricultural machine.

43. The method of claim 42, further comprising determining measurement data comprising one or more of soil moisture data or soil organic matter data or soil porosity data or soil texture data or soil type data; based on the measurement data, generating a signal to cause the agricultural machine to control a seed meter to change a population of seeds planted in the soil.

44. The method of claim 42, further comprising determining measurement data comprising one or more of soil moisture data or soil organic matter data or soil porosity data or soil texture data or soil type data; based on the measurement data, generating a signal to cause the agricultural machine to change a seed variety of seeds planted in the soil.

45. The method of claim 42, further comprising determining measurement data comprising one or more of soil moisture data or soil organic matter data or soil porosity data or soil texture data or soil type data; based on the measurement data, generating a signal to cause the agricultural machine to adjust a rate of application of one or more of a fertilizer or a fungicide or an insecticide by the agricultural machine.

46. The method of claim 42, further comprising determining measurement data comprising one or more of soil moisture data or soil organic matter data or soil porosity data or soil texture data or soil type data; based on the measurement data, generating a signal to cause the agricultural machine to adjust a force applied to the soil by the implement.

47. The method of claim 42, further comprising determining measurement data comprising furrow residue data; based on the measurement data, generating a signal to cause the agricultural machine to adjust a force applied in relation to the soil by a row cleaner of the implement.

48. The method of claim 42, further comprising:
displaying, in one or more windows of a monitor coupled to the implement, a representation of the measurement data, the one or more windows comprising:
a soil moisture window to display estimated soil moisture data; or
a soil temperature window to display estimated soil temperature data; or
a depth setting window to display a depth at which the one or more sensors are sensing the measurement data; or
a reflectivity variation window to display reflectivity data comprising a statistical reflectivity variation in a signal generated by a reflectivity sensor of the one or more sensors; or
a carbon content window to display estimated soil carbon content data; or
an organic matter window to display estimated soil organic matter content data; or
a soil components window to display estimated fractional presence data relating to one or more soil components.

49. The method of claim 42, further comprising displaying, in a monitor coupled to the implement, a predicted agronomic result based on reflectivity data comprising a statistical reflectivity variation in a signal generated by a reflectivity sensor of the one or more sensors.

50. The method of claim 42, further comprising:
displaying, in a monitor coupled to a plurality of row units of the implement, one or more of:
an average value of the measurement data for all of the plurality of row units;
a highest value of the measurement data for all of the plurality of row units;
a lowest value of the measurement data for all of the plurality of row units;
individual values of the measurement data for each of the row units in the plurality of row units.

51. The method of claim 42, further comprising:
displaying, in one or more windows of a monitor coupled to the implement, a representation of data, wherein the data comprises one or more of soil data, the measurement data, or estimated data, the data relates to one or more of soil carbon content or soil electrical conductivity or soil organic matter or soil components or soil moisture or soil temperature, and the one or more windows comprises:

a map window to display a subset of the data, wherein the subset of the data corresponds to a numerical range of reflectivity variation associated with a threshold level of predicted emergence failure.

52. The method of claim 42, further comprising:
displaying, in one or more windows of a monitor coupled to the implement, a representation of planting data, wherein the planting data is measured by the one or more sensors, the one or more sensors comprise one or more of an optical seed sensor or an electromagnetic seed sensor or a reflectivity sensor, and the one or more windows comprises:
one or more planting data windows to display one or more good spacing data values, wherein the one or more good spacing data values are calculated by the one or more processors based on seed pulses obtained from the one or more sensors.

53. The method of claim 42, further comprising causing a monitor to receive weather data and soil data from one or more servers over a network, transmit the measurement data to the one or more servers using the network, and receive agronomic recommendation data from a recommendation system on the one or more servers.

54. The method of claim 42, further comprising causing a depth adjustment actuator of the agricultural machine to cooperate with a trench opening system of the agricultural machine to adjust the depth of the trench.

55. The method of claim 54, further comprising causing the depth adjustment actuator to modify a height of a gauge wheel of the trench opening system relative to an opener disc of the trench opening system to adjust the depth of the trench.

56. The method of claim 42, further comprising causing a seed meter coupled to a hopper of the agricultural machine to control a rate of deposit of seeds from the hopper into the soil.

57. The method of claim 56, further comprising causing a monitor in data communication with the one or more sensors and one or more clutches of the agricultural machine to cause the one or more clutches to selectively couple the seed meter to an electric drive.

58. The method of claim 42, further comprising causing a monitor to receive, from one or more temperature sensors mounted to the agricultural implement, a signal relating to a temperature of the soil; obtaining the measurement data from the signal.

59. The method of claim 42, further comprising causing a monitor to receive, from one or more reflectivity sensors mounted to the agricultural machine, a reflectivity signal relating to a reflectivity of the soil; obtaining the measurement data from the signal.

60. The method of claim 59, further comprising identifying a first portion of the reflectivity signal as a seed pulse; identifying a second portion of the signal as a measurement of a soil characteristic.

61. The method of claim 59, further comprising identifying a wavelength of the reflectivity signal that is associated with a characteristic of a seed; obtaining reflectivity measurement data at the wavelength.

62. The method of claim 59, further comprising using the reflectivity signal, determining a seed pulse; based on the seed pulse, causing adjusting a timing of a deposit of an input into the trench by the implement during operation of the agricultural machine.

63. The method of claim 59, further comprising using the reflectivity signal, identifying a presence of crop residue in the trench; based on the identified presence of crop residue, causing adjusting of one or more of a valve or an actuator of the implement during operation of the agricultural machine.

64. The method of claim 63, further comprising displaying on a monitor, based on the identified presence of crop residue, a map of spatial variation in crop residue.

65. The method of claim 59, further comprising, using the reflectivity signal, determining a seed pulse; based on the seed pulse, determining a geospatially-mapped orientation of a seed.

66. The method of claim 59, further comprising, using the reflectivity signal, determining seed-to-soil contact data; displaying a map of spatial variation in the seed-to-soil contact data on the monitor.

67. The method of claim 42, further comprising receiving, from one or more electrical conductivity sensors, a signal relating to an electrical conductivity of the soil; obtaining the measurement data from the signal.

68. The method of claim 42, further comprising obtaining seed pulse data from an optical seed sensor of the one or more sensors; modifying the seed pulse data based on a signal generated by a reflectivity sensor of the one or more sensors.

69. The method of claim 42, further comprising, based on one or more signals from a plurality of reflectivity sensors mounted to a seed firmer of the agricultural machine, measuring a reflectivity of the soil.

70. The method of claim 42, further comprising, based on one or more signals from a capacitive moisture sensor mounted to a seed firmer of the agricultural machine, measuring a capacitance moisture of the soil.

71. The method of claim 42, further comprising, based on one or more signals from an electronic tensiometer sensor mounted to a seed firmer of the agricultural machine, measuring a soil moisture tension of the soil.

72. The method of claim 42, further comprising using the measurement data obtained from the one or more sensors to determine a soil moisture tension of the soil.

73. The method of claim 42, further comprising based on one or more signals from a temperature sensor mounted to a seed firmer of the agricultural machine, measuring a temperature of the soil.

74. The method of claim 42, further comprising obtaining the measurement data by interfacing with a plurality of soil-engaging ears comprising a conductive material coupled to the implement.

75. The method of claim 42, further comprising, based on a measured temperature of the soil, adjusting one or more of soil reflectivity measurement data or soil electrical conductivity measurement data.

76. The method of claim 42, further comprising obtaining the measurement data from one or more sensors mounted to a seed firmer of the agricultural machine, the one or more sensors comprising a plurality of reflectivity sensors and a plurality of temperature sensors and a plurality of electrical conductivity sensors.

77. The method of claim 42, further comprising based on reflectivity measurement data obtained from a reflectivity sensor of the one or more sensors, calculating a seed germination moisture value; causing adjusting the depth of the trench formed in the soil by the implement during operation of the agricultural machine based on the seed germination moisture value.

78. The method of claim 42, further comprising calculating a uniformity of moisture value based on the measurement data obtained from the one or more sensors; causing adjusting the depth of the trench formed in the soil by the implement during operation of the agricultural machine based on the uniformity of moisture value.

79. The method of claim 42, further comprising calculating an emergence environment score based on the measurement data obtained from the one or more sensors; causing adjusting the depth of the trench formed in the soil by the implement during operation of the agricultural machine based on the emergence environment score.

80. The method of claim 42, further comprising calculating a moisture variability value based on the measurement data obtained from the one or more sensors; causing adjusting the depth of the trench formed in the soil by the implement during operation of the agricultural machine based on the moisture variability.

81. The method of claim 42, further comprising removing measurement of ambient light from a total light measurement measured from a reflectivity sensor of the one or more sensors, by:

emitting light from an emitter of the reflectivity sensor;
measuring the total light measurement;
turning off the emitter;
measuring ambient light;
calculating reflected light by subtracting the ambient light measurement from the total light measurement.

82. The method of claim 42, further comprising analyzing voids in the soil by:

causing moving a reflectivity sensor through the soil;
measuring reflectivity received at first and second detectors of the reflectivity sensor;
obtaining speed of the reflectivity sensor through the soil;
calculating at least one of void length, void depth, and number of voids per linear distance from a first detector reflectivity measurement and a second detector reflectivity measurement.

\* \* \* \* \*